US009107595B1

(12) United States Patent
Smyth

(10) Patent No.: US 9,107,595 B1
(45) Date of Patent: Aug. 18, 2015

(54) NODE EXCITATION DRIVING FUNCTION MEASURES FOR CEREBRAL CORTEX NETWORK ANALYSIS OF ELECTROENCEPHALOGRAMS

(71) Applicant: U.S. Army Research Laboratory, Adelphi, MD (US)

(72) Inventor: Christopher C. Smyth, Fallston, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 14/499,562

(22) Filed: Sep. 29, 2014

(51) Int. Cl.
*A61B 5/04* (2006.01)
*A61B 5/0476* (2006.01)

(52) U.S. Cl.
CPC ........... *A61B 5/04012* (2013.01); *A61B 5/0476* (2013.01)

(58) Field of Classification Search
None
See application file for complete search history.

(56) References Cited

U.S. PATENT DOCUMENTS

| 8,708,884 | B1 | 4/2014 | Smyth | |
|---|---|---|---|---|
| 2010/0042011 | A1* | 2/2010 | Doidge et al. | 600/544 |
| 2012/0296569 | A1* | 11/2012 | Shahaf et al. | 702/19 |
| 2014/0094710 | A1* | 4/2014 | Sarma et al. | 600/544 |
| 2014/0163328 | A1* | 6/2014 | Geva et al. | 600/300 |

OTHER PUBLICATIONS

Hairston WD, Letowski TR, and McDowell K, "Low-level auditory processing as a predictive tool for within- and cross-model performance," presented at the 27th Army Science Conference, Orlando, FL (2010).
M. Napflin, M. Wildi, and J. Sarnthein, "Test-retest reliability of resting EEG spectra validates a statistical signature of persons", Clinical Neurophysiology, 118, 2519-2524 (2007).
U.S. Appl. No. 14/499,625, titled "Method and Apparatus for Estimating Cerebral Cortical Source Activations From Electroencephalograms," filed Sep. 29, 2014.
U.S. Appl. No. 13/792,585, titled "Apparatus and Method for Estimating and Using a Predicted Vehicle Speed in an Indirect Vision Driving Task," filed Mar. 11, 2013.
U.S. Appl. No. 13/721,161, titled "Method and Apparatus for Facilitating Attention to a Task," filed Dec. 20, 2012.

* cited by examiner

*Primary Examiner* — Etsub Berhanu
(74) *Attorney, Agent, or Firm* — Eric Brett Compton

(57) ABSTRACT

Methods and apparatuses for estimating brain activity of a human subject from the measurement of electroencephalograms (EEG) are disclosed. In one method, cortical neural sources in the cerebral cortex of the brain of the subject are specified. Next, using a model of the human brain which treats the cortical neural sources as nodes in a cortical source network, cortical source activations are estimated from the measured electroencephalograms for each of the cortical neural sources in the network for the subject. Source network modulation control signals are then determined for the subject from the cortical source activations which are assumed to correspond to control modulators in the human brain. And a network activity classification is computed from determined modulation control signals for the subject. The innovative technology may be included in an automated aiding system in the electronic aiding of tasks performed by human operators.

19 Claims, 44 Drawing Sheets

Table 1. Source node degree by event class

| event | Source node | | | | | | | | | |
|---|---|---|---|---|---|---|---|---|---|---|
| | N1 | N2 | N3 | N4 | N5 | N6 | N7 | N8 | N9 | N10 |
| base | 9 | 9 | 8 | 0 | 6 | 6 | 9 | 8 | 6 | 0 |
| stimulus | 8 | 5 | 2 | 8 | 8 | 6 | 3 | 9 | 8 | 8 |
| response | 5 | 0 | 4 | 5 | 0 | 4 | 6 | 4 | 6 | 3 |
| average | 7.3 | 4.7 | 4.7 | 4.3 | 4.7 | 5.3 | 6.0 | 7.0 | 6.7 | 3.7 |

Table 2. Clustering coefficient for source node by event class

| event | Source node | | | | | | | | | |
|---|---|---|---|---|---|---|---|---|---|---|
| | N1 | N2 | N3 | N4 | N5 | N6 | N7 | N8 | N9 | N10 |
| base | .23 | .23 | .25 | 0 | .35 | .34 | .22 | .26 | .35 | 0 |
| stimulus | .24 | .42 | 1.67 | .24 | .24 | .34 | .84 | .21 | .25 | .24 |
| response | .44 | 0 | .59 | .42 | 0 | .59 | .33 | .56 | .34 | .87 |
| average | .30 | .22 | .84 | .22 | .20 | .42 | .46 | .34 | .31 | .37 |

Table 3. Path length of source node by event class

| event | Source node | | | | | | | | | |
|---|---|---|---|---|---|---|---|---|---|---|
| | N1 | N2 | N3 | N4 | N5 | N6 | N7 | N8 | N9 | N10 |
| base | 1.09 | 1.11 | 1.02 | 0 | 0.77 | 0.79 | 1.12 | 0.99 | 0.77 | 0 |
| stimulus | 1.04 | 0.66 | 0.27 | 1.06 | 1.04 | 0.78 | 0.40 | 1.20 | 1.04 | 1.05 |
| response | 0.64 | 0 | 0.50 | 0.66 | 0 | 0.50 | 0.80 | 0.53 | 0.79 | 0.38 |
| average | 0.92 | 0.59 | 0.60 | 0.75 | 0.60 | 0.69 | 0.77 | 0.91 | 0.87 | 0.48 |

Table 4. Efficiency of source node by event class ($\times 10^{-2}$)

| event | Source node | | | | | | | | | |
|---|---|---|---|---|---|---|---|---|---|---|
| | N1 | N2 | N3 | N4 | N5 | N6 | N7 | N8 | N9 | N10 |
| base | .11 | .11 | .12 | 0 | .16 | .16 | .11 | .12 | .16 | 0 |
| stimulus | .12 | .19 | .46 | .12 | .12 | .16 | .31 | .10 | .12 | .12 |
| response | .19 | 0 | .25 | .19 | 0 | .24 | .15 | .23 | .16 | .32 |
| average | .14 | .10 | .28 | .10 | .09 | .18 | .19 | .15 | .14 | .15 |

Table 5. Network metrics

| Event | Degree | clustering | diameter* | efficiency |
|---|---|---|---|---|
| Base | 6.1 | 0.22 | 0.77 | 0.11 |
| Stimulus | 6.5 | 0.47 | 0.85 | 0.18 |
| Response | 3.7 | 0.41 | 0.48 | 0.17 |
| Average | 5.4 | 0.37 | 0.70 | 0.15 |

*Note: scale-free network diameter (N = 10) ~ 0.83

Table 6. Event Network Type

Base – default network (scale-free): spread out with high degree and high diameter, little focus with low clustering and low efficiency.

Stimulus – focused task network (scale-free): spread out with high degree and high diameter, strong focus with high clustering and high efficiency.

Response – activated task network (small-world): concentrated with low degree and small diameter, strong focus with high clustering and high efficiency.

Table 7. Nodes activated by event class

| Node | base | stimulus | response |
|---|---|---|---|
| N1 | X | X | |
| N2 | X | X | X |
| N3 | X | X | X |
| N4 | | X | X |
| N5 | X | X | |
| N6 | X | X | X |
| N7 | X | X | |
| N8 | X | X | |
| N9 | X | X | |
| N10 | | X | X |

FIG. 33

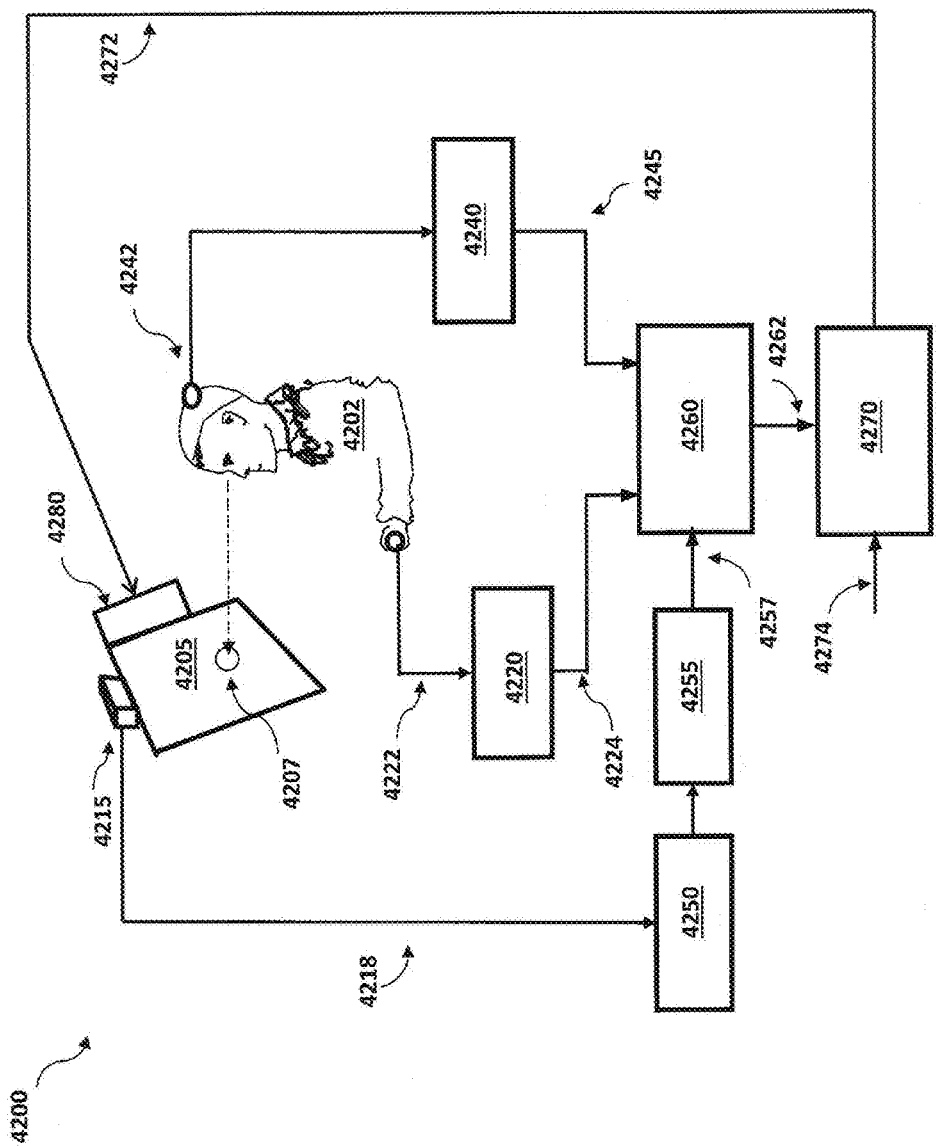

NODE EXCITATION DRIVING FUNCTION MEASURES FOR CEREBRAL CORTEX NETWORK ANALYSIS OF ELECTROENCEPHALOGRAMS

GOVERNMENT INTEREST

Governmental Interest—The invention described herein may be manufactured, used and licensed by or for the U.S. Government.

RELATED APPLICATION(S)

This patent application is related to U.S. patent application Ser. No. 14/499,625 filed Sep. 29, 2014, titled "METHOD AND APPARATUS FOR ESTIMATING CEREBRAL CORTICAL SOURCE ACTIVATIONS FROM ELECTROENCEPHALOGRAMS," herein incorporated by reference in its entirety.

FIELD OF INVENTION

Embodiments of the present invention generally relate to determining brain activity from scalp site recorded electroencephalograms.

BACKGROUND OF THE INVENTION

Brain activity is commonly determined from electroencephalograms (EEG) measurements from multiple electrodes positioned on scalp sites over the subject's head, with signals from the electrodes fed to an EEG data collection system. Following artifact rejection (typically performed), signal analysis of electroencephalograms (EEG) measurements using short-term Fourier analysis or wavelet analysis produces a time-frequency spectral data analysis for the sites. The spectral results may be decomposed into spectrum band power; spectrum coherence computed from the power spectral matrix; and causality for the coherence between the sites as a network such as Granger causality.

Further refinement in decompositions where there is spectrum coherence (as a measure of mutual synchronicity among sites), may be decomposed into different measures of the Granger causality for the direction of information flow among sites. These measures include the directed coherence (DC), which is defined as the ratio of the spectral transfer function between two sites, and the square root of the auto power of one of the sites; and still further, the directed transfer function (DTF).

In further developments, graph theory measures are applied for analysis of the sites as nodes of a network, by using small world network metrics computed from the cross-correlation matrices for the sites, such as node degree (average number of connections nodes), clustering coefficient (ratio of existing connections to all possible), diameter (shortest path between nodes), and efficiency (measure of number of parallel connections among nodes), among others. In experimental studies, statistical analysis may be applied to these measures by treatments for study results.

While these conventional methods are of interest to the research community, they are commonly of low statistical power as shown by sometimes conflicts in replication of study results. This is because the statistics used in these studies analyzes the power spectrums for the sites and the coherences between the sites (or derivations thereof), as separate statistical measures. This conventional methodology can result in a large number of measures; for instance, there are at least 2030 separate measures for a study with a 64-electrode scalp site EEG data collection system (an analysis of signals from N scalp sites conducted separately would involve N-power spectrums and $N*(N-1)/2$ coherence spectrums). Furthermore, the analyses are commonly conducted separately by frequency bands of which there are at least four considered in the EEG spectrum: delta, alpha, beta, and gamma, although the study may be limited to a single band. This large number of measures severally reduces the overall statistical power of any analysis and increases the family-wise Type I error (that is, error in accepting the analysis as significant). Of further concern is that these measures are all from same data source and being highly correlated are redundantly a single measure; it is suspect to include all as separate dependent measures in conventional statistical methods (such as multiple analysis of variance), thereby increasing the probability that results are incorrectly significant by chance alone.

Therefore, if measurement of electroencephalograms (EEG) with a scalp site electrode EEG data collection system is to be useful in real-life applications (such as in moving vehicles with operator control), there is a need in the art for a method and apparatus for generating a global measure for electroencephalograms (EEG) analysis. Further, there is an advantage in the extension of such a global measure to cerebral sources of the scalp site electroencephalograms (EEG), with the sources located by cortical structure that form cerebral networks relatable to cognitive functions.

BRIEF SUMMARY OF THE INVENTION

Embodiments of the present invention provide methods and apparatuses for estimating brain activity of a human subject from the measurement of electroencephalograms (EEG) using scalp site electrodes attached to the subject's scalp and an EEG data collection system. In an exemplary embodiment, a method comprises: specifying a plurality of cortical neural sources in the cerebral cortex of the brain of the subject; using a model of the human brain which treats the cortical neural sources as nodes in a cortical source network, estimating cortical source activations from the measured electroencephalograms for each of the cortical neural sources in the network for the subject; determining source network modulation control signals for the subject from the cortical source activations which are assumed to correspond to control modulators in the human brain; and computing a network activity classification from determined modulation control signals for the subject.

Estimating the cortical source activations may include applying a node-excitation driving function, where each node is assumed to constitute an activation function formed from weighted inputs, a node-excitation driving function, and an emitter function formed from weighted outputs. The node-excitation driving function can be computed from a multivariate spectral analysis of the network node excitations, where the spectral analysis follows from autoregressive coefficients and the noise covariance resulting in node power spectrums and inter-node transfer functions. For example, the node-excitation driving function may be computed as the ratio of the node partial spectral power and the node activation function, and the node activation function is computed as the sum of the spectral power inputs weighted by the corresponding normalized transfer functions. The modulation control signals of the network control modulation nodes are determined from the network node-excitation driving functions. The network activity classification can be made as to the level of activity from the modulation control signals of the network control modulation nodes, as derived from the network source node-excitation driving functions for the cortical source activations.

The network activity classification can also be made as to task nature from the topological organization as derived from the network source node excitation driving functions for the source activations. For instance, the networks are cortical attention networks include task default, task focus, task involvement, or any combination thereof. The network activity classification is made to task functional activity by mapping the network cortical sources to the cortical structure of the brain as cortical functional network nodes related to cognitive functions, including at least to the structural level of the Brodmann Area regions of the cortex with associated cognitive functions. And the network activity classification might be made to task functional activity level from the cortical structures of the cortical functional network as derived from the network source node excitation driving functions for the corresponding source activations.

In a further embodiment, an apparatus having a plurality of electronics modules to execute the aforementioned method is provided. Also, the apparatus may be incorporated as a component of an automated task aider used to estimate the task attention of the subject.

These and other embodiments are explained below in further detail.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments. These embodiments are intended to be included within the following description and protected by the accompanying claims.

FIG. 33 includes tables of network metrics for cerebral source node excitation driving functions;

FIG. 42 is schematic of automatic aiding configuration for operator in autonomous system according to an embodiment.

DETAILED DESCRIPTION OF THE INVENTION

An innovative methodology for estimating brain activity of a human subject from the measurement of electroencephalograms (EEG) with a scalp site electrode EEG data collection system where multiple electrodes are positioned on scalp sites on the head of the subject is disclosed. The methodology uses a novel model of the human brain which treats a network of cerebral cortical sources in the brain as nodes and that assumes that node-excitation driving functions for the nodes can be determined from EEG measurements. The node-excitation driving functions are computed from independent component analysis and parameterized by multivariate spectrum analysis of the time-series network that is formed by the nodes of the cortical network. The spectrum measures of the cortical network are reduced to a global measure of the network-node effects by combining the node power and the coherences between the nodes (as a measure of the degree that the node oscillations maintain a fixed relation to each other), into a single node excitation function for each node.

Depending upon the value of the network modulation, the excitation functions of the nodes may be used as network metrics to determine the state of the cognitive processing by the network, where the cortical sources are assumed to be cortical structures relatable to cognitive functions. Further, source network modulation control signals are determined from the cortical source activations which are assumed to correspond to control modulators in the brain. And a network activity classification is established from determined modulation control signals.

A key advantage of this invention over the prior art is that a global measure is generated for the node network along with a single effect measure for each node, thereby increasing the statistical power of the application, and that the global measure is relatable to cognitive functions through the node effect measures. On that basis, one exemplary application is as a component of an automated aiding system in the electronic aiding of tasks performed by human operators by providing an estimate of brain functions from electroencephalogram measurements.

Figure 1:
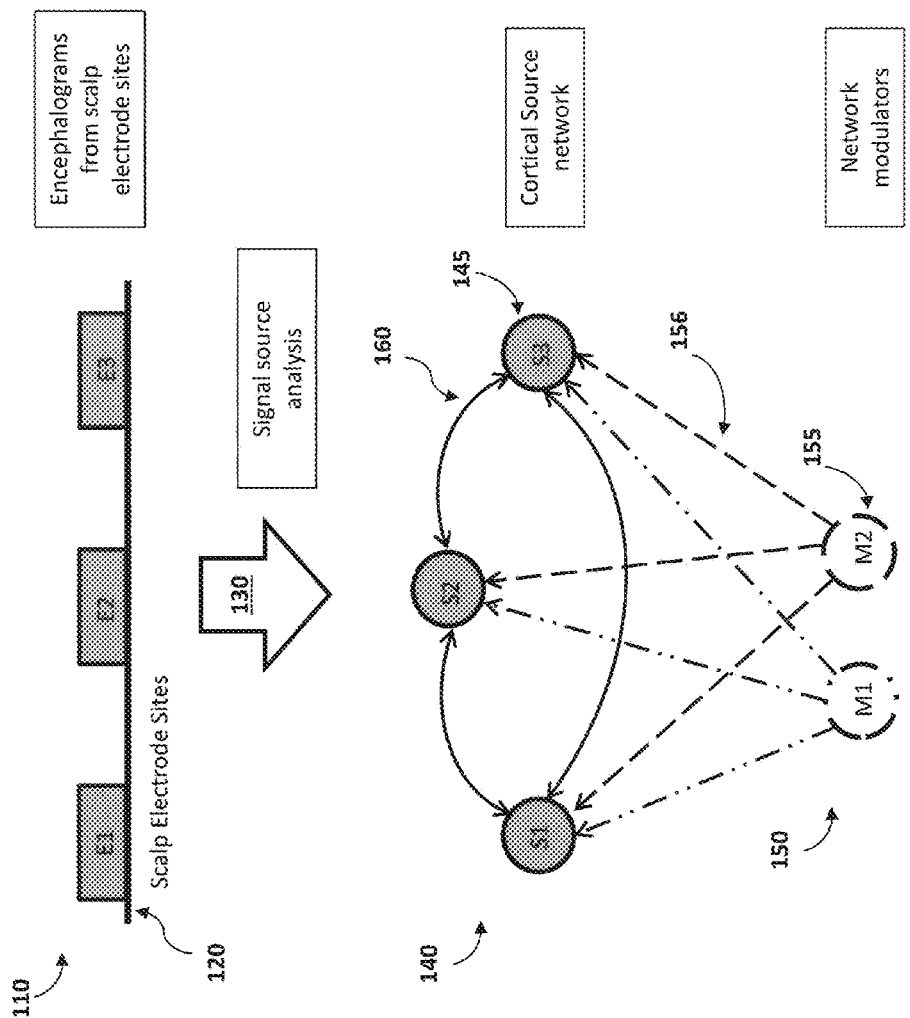
FIG. 1 is a schematic of electroencephalogram reduction to cortical source network which is used in a methodology for estimating brain activity of a human subject according to an embodiment.

FIG. 1 depicts an exemplary schematic of electroencephalogram reduction to a cortical source network which is used in a methodology for estimating brain activity of a human subject according to an embodiment. One key premise of the innovative methodology is that specific activation of cerebral cortex networks in the human brain can be properly estimated using novel modeling of the node excitation driving functions. The node excitation driving function combines the node power and coherences into a single measure for a plurality of cortical sources of the network that can be derived from electroencephalograms (EEG) measurements. In turn, modulation sources for the networks are derived from the driving functions to classify brain network activity.

Referring to FIG. 1, a plurality of scalp site electrodes 110 (labeled E1, E2, E3 . . . in the figure) are attached to the subject's scalp 120 for recording electrical signals collected by the electrodes 110. In actuality, ten (10) twenty (20), or even more electrodes are typically attached to the scalp 120. Conducting gel may be further applied at the electrode sites to help to conduct electrical signals from the scalp 120 to the electrodes 110. The electrodes 110 are placed in a generally distributed manner at spaced locations across the surface of the scalp 120. The electrodes 110 may be sewn or otherwise provided in a fabric cap (not shown) which the subject wears. Alternatively, the electrodes 110 may be removably attached to the scalp 120 with a glue or adhesive which can be washed away with a suitable solvent, such as acetone.

In one embodiment, the electroencephalograms are collected from scalp surface electrode sites according to the International 10-20 electrode system standard or extensions thereof which are commonly used for locating electrode placement on the scalp in preparation for EEG recordings. The EEG electrodes 110 measure electrical signals produced by the brain neurons near the scalp which originate in the cerebral cortex of the brain. The cerebral cortex is the outermost layered structure of neural tissue of the brain. The cerebral cortex plays an important role in many cognitive functions, including memory, attention, perception, awareness, thought, language, and consciousness.

Electrical signals detected by the scalp site electrodes 110 are feed to a computing device for signal source analysis 130. The analysis 130 models a cortical network 140 to multiple network modulators 150 in the subject's brain. The cortical network 140 is composed a plurality of interconnected cortical sources 145 (labeled S1, S2, S3 . . . in the figure). The cortical sources 145 represent discrete groups of neurons in the cortex of the subject's brain which have nearly identical receptive fields and function, and that grouped together are assumed to be located in Brodmann Areas in the brain.

As known, Brodmann Areas are regions of the cerebral cortex having the same cytoarchitectural organization of neurons as originally defined and numbered by German neurologist Dr, Korbinian Brodmann in 1909. There are some 52 Brodmann areas which have been defined in human and non-human primates brains associated with various cognitive functions, although not all are present or used in human brains. So-called "Brodmann atlases" or "Brodmann maps" are available which depict the various Brodmann areas in the brain and indicate their functions.

Brodmann Areas have been mapped to specific locations in the human brain. One way to do this is using Talairach space, a known 3-dimensional coordinate system of the human brain, which is used to map the location of brain structures independent from individual differences in the size and overall shape of the brain, with Brodmann areas as labels for both lateral and median surface brain regions (as derived by Jean Talairach and Gabor Szikla in 1967). Talairach space represents a standardized atlas or grid for mapping the human brain, which defines standard anatomical landmarks that could be identified on different individuals. An individual's brain image obtained through Magnetic Resonance Imaging (MRI), positron emission tomography (PET) and other brain imaging methods can be mapped to this standard Talairach space using conventional software applications. For example, atlases, such as the Talairach Daemon and CARET (Computerized Anatomical Reconstruction Toolkit) applications can approximate between three-dimensional locations in the brain and Brodmann Areas. Another way is through Montreal Neurological Institute (MNI) standard brain coordinate system, which is based on studies of Magnetic Resonance Imaging (MRI) data for a large number of persons. This latter technique is supposedly more representative of the population. There are various known functions for converting MNI standard brain coordinate system to Talairach space.

In the present methodology, not all Brodmann areas need to be used as cortical sources 145. One may choose to select a subset of one or more Brodmann areas which correspond to one or more cognitive functions of interest. The cortical sources 145 which are assumed to correspond to Brodmann area locations in the subject's brain can be mapped to a standard cortical space coordinate system, like Talairach space or MNI standard brain coordinate system. In further embodiments, the cortical sources 145 may be derived in a functional MRI brain study for the individual subject to identify regions linked to critical cognitive functions, such as speaking, moving, sensing, or planning, among others. In turn, the individual results may be again mapped to a standard cortical space for location as Brodmann Areas.

Connectivity of the cortical sources 145 is identified as signals 160. Because of this interconnectivity, the scalp site electrodes 110 are believed to measure electrical signals which actually represent the combination of multiple signals originating from various cortical sources 145 in the brain.

Accordingly to the model, each of the cortical sources 145 of the network 140 can be considered a node and that a driving function exists for that node which can characterize the effect of the interconnectivity 160 among the various modulating sources 155 in the network 150 as further explained herein.

The network of modulators 150 is composed of independent modulating sources 155 (labeled M1, M2, . . . in the figure) within the brain. Signals 156 from the modulating sources 155 affect the cortical sources 145. At this time, there is no way of specifically knowing the exact source network modulators in the human brain, only of determining the level of the control signals based on the novel independent component methodology applied to the cortical source driving functions. With a greater understanding of the interworking of the human mind, in the future, perhaps the specific source network modulators can be more accurately determined. Nonetheless, the innovative methodology provides a much greater understanding of the influence of the cognitive modulators on EEG measurements for an individual.

Figure 2:
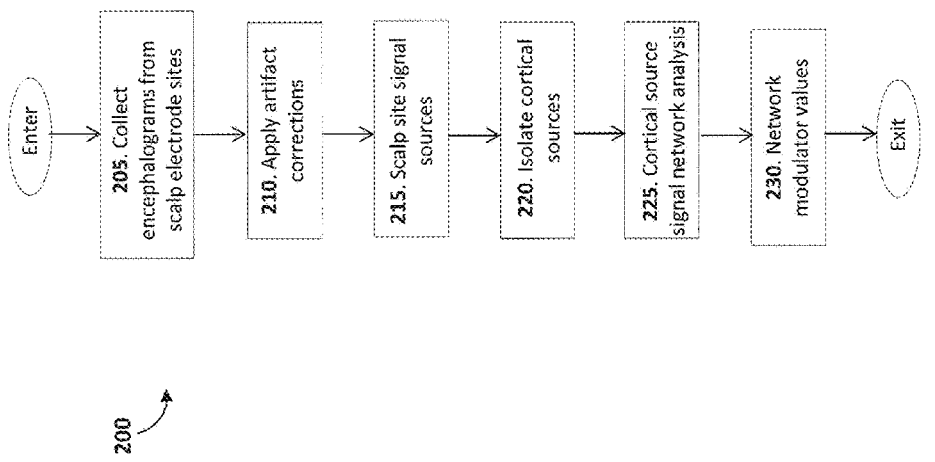
FIG. 2 is a flow chart of process for reducing encephalogram to cortical source network.

FIG. 2 is a flow chart of the innovative methodology 200 for determining specific brain activity of a subject from the measurement of electroencephalograms (EEG) according to an embodiment. The methodology 200 comprises the following processes: (1) the encephalograms are collected as voltages samples over a time window period from the electrodes attached to scalp skin sites in step 205; (2) the scalp signals are (optionally) corrected for the additions of artifact signals in step 210 from extra-cerebral sources such as eye-movements, muscle movements, or the environment; (3) the analysis of the scalp signals for the sources of the scalp voltages in step 215 by blind-source separation of temporal-wise independent sources based in some applications on kurtosis of the source signals; (4) the isolation of the cerebral sources in step 220 from the source set from those of the artifacts by location of the sources by scalp site triangulation of the source signals, and by source signal characteristics of waveforms, amplitude probability density functions and spectral density functions; (5) the analysis in step 225 by multivariate spectrum analysis of the cortical sources as nodes of a cortical network and the determination of node-excitation driving functions from the spectral parameters for the sources; and (6) the determination of network modulation values step 230 from the node-excitation driving functions. Each of these steps is explained in further detail below.

Figure 3:
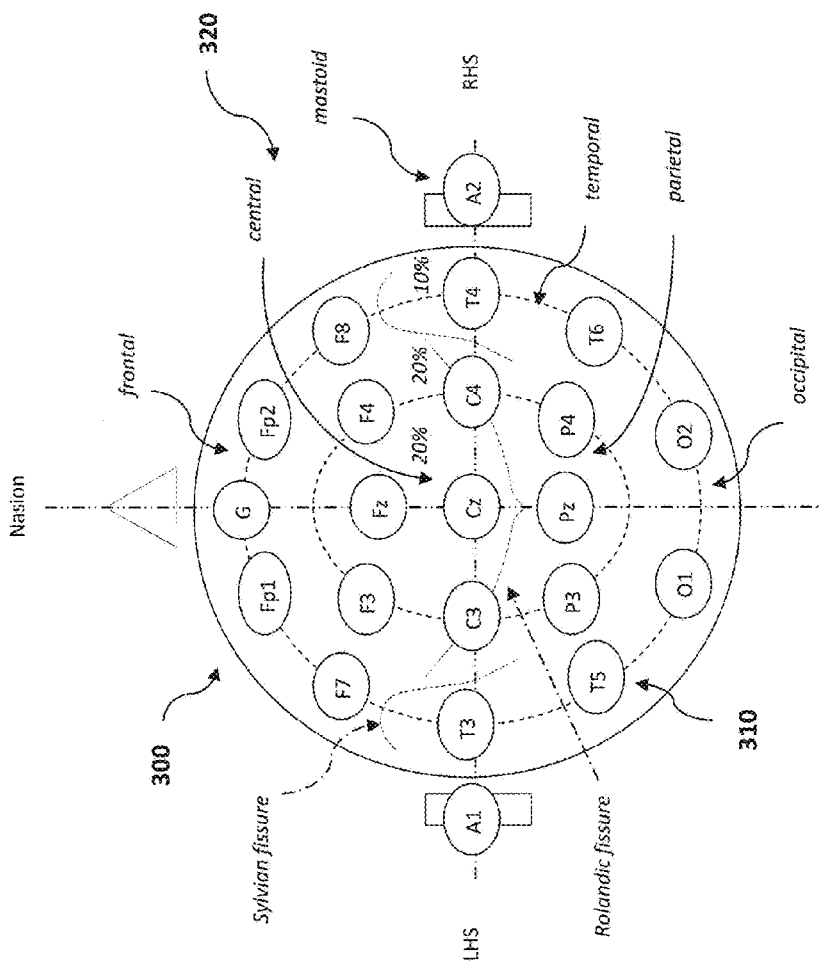
FIG. 3 is a schematic of International 10-20 electrode system scalp sites.

FIG. 3 is a schematic of a single plane projection of the human scalp showing nineteen (19) electrode sites of the International 10-20 electrode system 300 which may be used in embodiments of the present invention. The International 10-20 system is an internationally-recognized standard to describe and apply the location of scalp electrodes for EEG testing.

The various lobes and major fissures of the underlying brain are also illustrated in the figure for reference. The human brain is separated into different region (or lobes) which include the frontal, temporal, central, parietal, and occipital lobes. The Rolandic fissure is the central sulcus, or fold, in the brain; it separates the parietal lobe from the frontal lobe. The Sylvian fissure is the most prominent lateral sulcus in the brain; it divides both the frontal lobe and parietal lobe above from the temporal lobe below. It is present in both hemispheres of the brain but is typically longer in the left hemisphere in most people.

Two anatomical landmarks are used for positioning the EEG electrodes on the scalp. These include the Nasion at the front of the skull and the Inion at the back. The Nasion is the distinctly depressed area between the eyes, just above the bridge of the nose, and the Inion is the lowest point of the skull from the back of the head and is normally indicated by a prominent bump. The projections of the Nasion at the front of the skull and the Inion at the back are illustrated for reference purposes in the figure.

In this electrode system, the electrode sites are positioned with respect to the sagittal plane (i.e., the vertical plane that dividing the body into right and left halves) at 20% intervals along the scalp mid-line Nasion to Inion distance, with the frontal site a distance of 10% from the Nasion; and located in the coronal plane at 20% intervals along the scalp between points just anterior to the tragus of each ear, with the most lateral site a distance of 10% from the tragus. The most forward and lateral sites define a horizontal plane for reference in electrode placement.

The sites are labeled 310, by letters, correspond to the underlying cortical lobe structure 320, such as: frontal (F), temporal (T), central (C), parietal (P), and occipital (O); and, by number, corresponding to distance from the horizontal plane, with the even numbers on the right side of the head (RHS), and the odd numbers on the left side (LHS). It actuality, there exists no central lobe, but the letter C is used according to the standard. The identifier "z" (zero) refers to the midline axis of the head. The sites Fp1, Fp2 identify frontal polar sites. The sites A1 and A2 represent the earlobes and are for mastoid references used in unipolar electrode montages. A site labeled 'G' may be used for the amplifier ground in the EEG collection system.

EEG recording caps (not shown) of elastic lightweight fabric that snugly fit over the subject's head are commercially available with electrodes and shielded recording wires for electrode placement in both standard montages and higher density electrode configurations, with scalp site preparation and conducting gel inserted at the electrode sites after fitting. The electrodes may be combined in different montages for recording purposes depending upon the purpose of the EEG study. In bipolar recordings, the electrodes are linked in pairs to the two inputs of differential amplifiers and the recordings are the voltage differences between the pairs. In unipolar (referential) recordings, the electrodes are linked to one input of the associated differential amplifiers and the other input of all amplifiers are linked to a separate reference electrode, either one of the mastoid sites (or the ear lobes) or the average of the two, or a separate site on the scalp or in some cases, the face or body; the recordings are of the voltage differences between the exploratory scalp electrodes and that of the reference. In a further development, the recordings may be added or subtracted in different combinations for a change in reference voltage and bipolar or unipolar configurations depending upon the focus of the study.

In a further embodiment, the recorded EEG is reduced to a set of cerebral sources generating the scalp voltage recordings as a set of mixed source signals.

Figure 4:
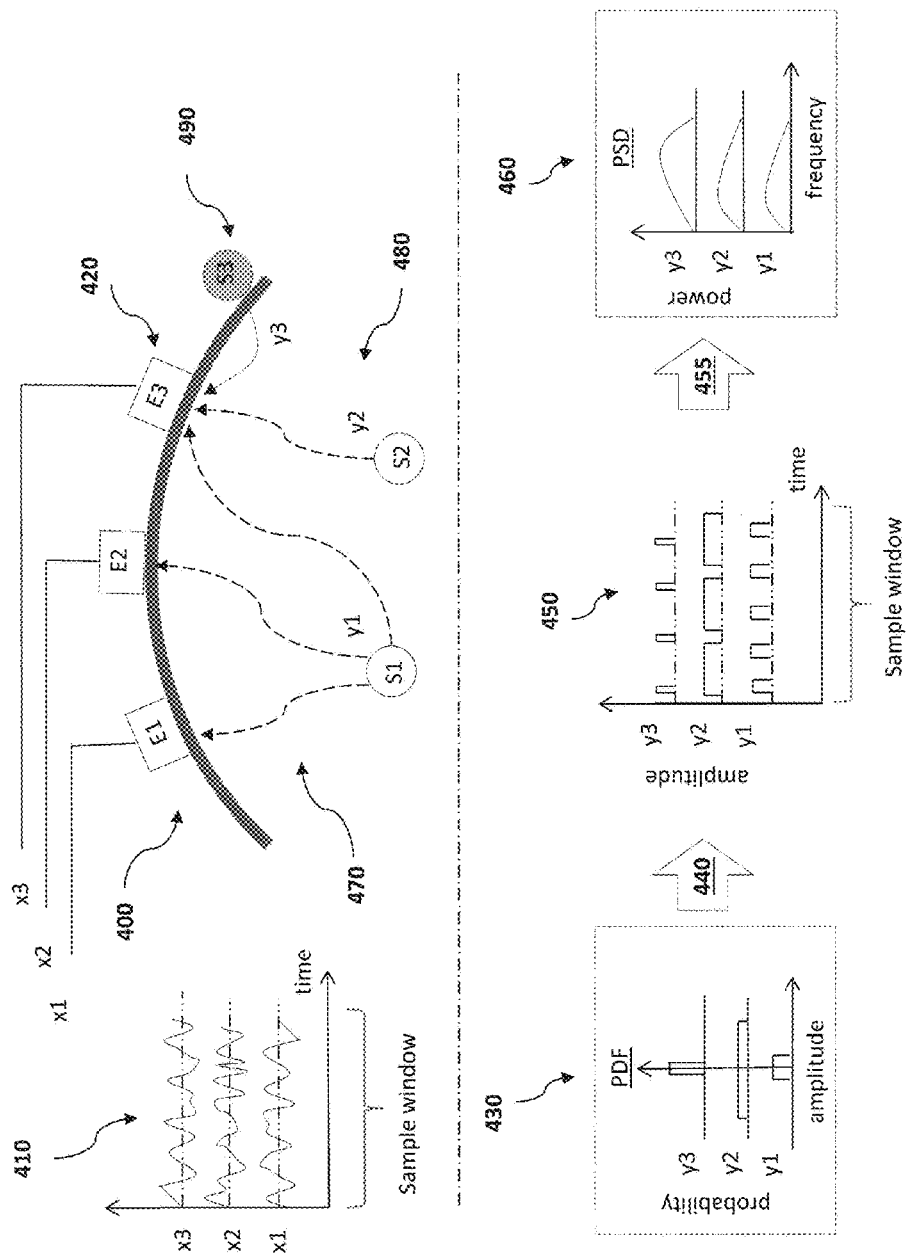
FIG. 4 is a schematic showing method for isolating encephalogram sources.

FIG. 4 is a schematic showing the steps in the initial processing EEG signals. In some embodiments, the voltage signals 400 from the scalp surface electrodes (labeled E1, E2, E3 . . . in the figure) may be pre-processed by band-pass filtering to remove signal baseline including electrode drift and high frequency extraneous artifacts. For example, the signals may be notched filtered as well to remove 60 Hertz power line noise.

The scalp signal windowed time samples 410 can be corrected for the additions of artifact signals from extra-cerebral sources, such as eye-movements, muscle movements, or the environment based on signal waveform extremes of excessive amplitude and trend among others, and on excessive low frequency power contents from eye movements or high frequency from muscle.

For most applications, this preprocessing removes obvious artifacts; however, a residual usually remains in the signals. The plot of samples 410 in the upper left of the figure, shows three signals (x1, x2, x3) measured by the electrodes (E1, E2, E3), respectively, over time.

The processed signals are next analyzed to determine a set of both cerebral (S1, S2) and possible extra-cerebral sources such as eye-movements, muscle movements, or the environment (S3) for the scalp voltages, where the outputs of such added together generate the voltage 420 at a scalp site (N3). In some embodiments, this determination can be done by blind-source separation following principal component analysis of the signals. For example, a method for deriving a set of temporal independent sources equal in number to the scalp sites, where the sources are separable by their time-wise signal amplitude probability moments; commonly, in the practice this is separation by the probability density function (PDF) of the source signal amplitude ($4^{th}$ moment) kurtosis 430 for function peakness from that for a Gaussian distribution. The separation method produces 440 a set of temporally separated sources (independent components), with time-wise signals in plot 450 over the sample window (by un-mixing of the scalp signals), that can used to separate the cerebral sources (S1, S2 . . . ) from any extra-cerebral sources (S3) by signal kurtosis and spectrum, and by source location. In this application, the power spectral density (PSD) may be computed 455 from the source time-wise signals and the resulting spectrum distributions shown in plot 460 used to prune the artifact sources from the cerebral sources. To this purpose, the kurtosis for an EEG process is commonly Gaussian and the spectrum density that of Brownian noise ($1/frequency^2$); peaks may be superimposed for localized theta, alpha or beta band level processing depending upon the source location.

For example, the spectrum density for an ocular source is commonly peaked about 2 Hz, while that for a muscle source is commonly peaked above 30 Hz. Further pruning can be performed by considering source location relative to the skull, in which the source is located by triangulation 470 of the potential from the source(s) received at the scalp sites. In some embodiments, a 3-shell spherical head model or even a 4-shell spherical head model for the scalp, skull, cerebrospinal fluid, and homogeneous cortex is of the art used to compute the source potential for a forward problem solution at the scalp sites for a dipole field source. In this process, cerebral potential sources locate within the cortex (480), while the ocular potential sources locate about the ocular orbit regions in the front of the skull, and the muscle potential sources outside the skull (490); here, with cortical source activation signals y1 and y2, and extra-cerebral source activation signal y3. The resulting set of cerebral sources may be further reduced to a working set by clustering adjacent sources together as a separate source based on proximity of spectrums and locations in a source feature space The electroencephalogram (EEG) may generally be represented as a white noise driven autoregressive process, in which the process output is the weighted sum of prior outputs and a white noise input.

Figure 5:
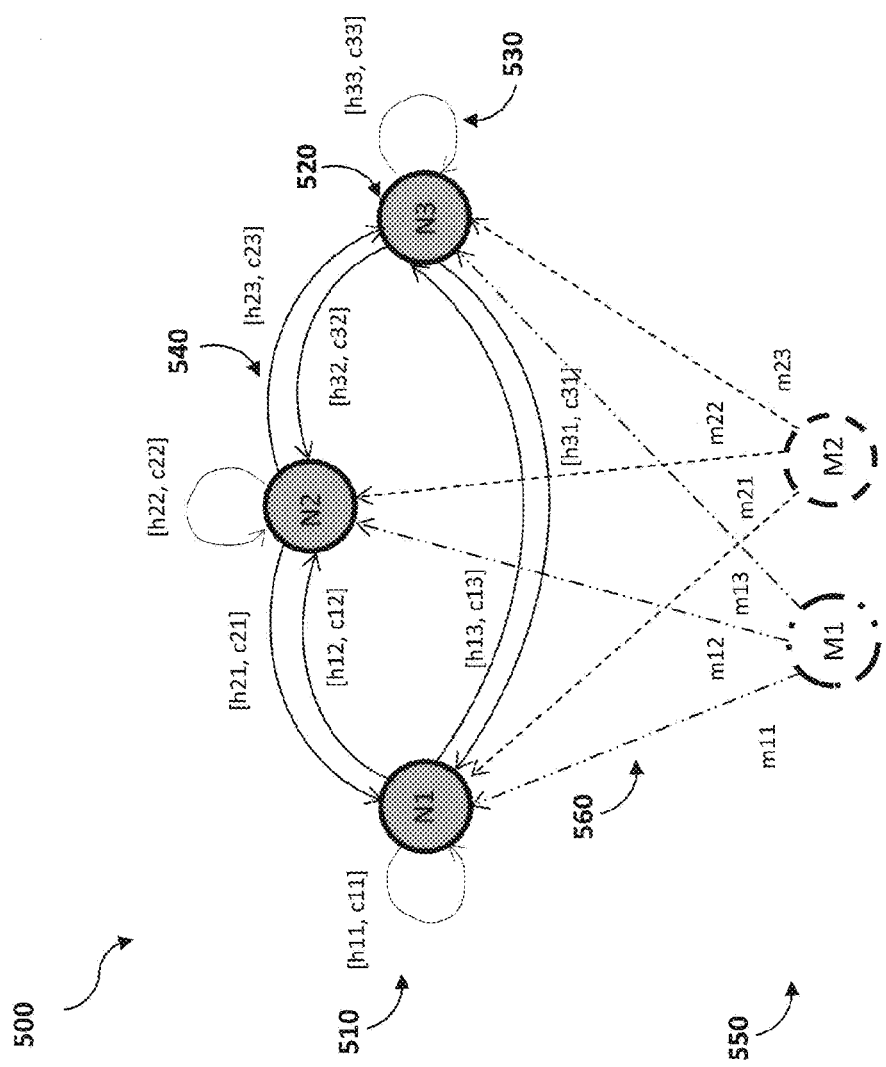
FIG. 5 is a schematic of cortical sources as a multivariate network showing interactions among sources.

FIG. 5 is a schematic of a model of networked cortical source nodes according to an embodiment as a time-series network. The model includes a set of cortical sources 500 arranged as a multivariate autoregressive network 510 showing the various interactions among the sources being characterized as network nodes (N1, N2, N3 . . . ), with modulators 550 controlling the network as a white noise driver.

The inputs to the nodes are the power of a noise covariance (c) as weighted by a transfer function (h) for the node connection as determined by an autoregressive analysis. For example, the node 520 (N3) is shown with a recursive feedback loop 530 as input of that node's output and with inputs from the outputs from the other nodes 540. Here, for the recursive loop for the node 520 (N3), the transfer function is denoted as h33 and the noise covariance as c33. The transfer function and covariance from node N2 which are input to node 520 (N3) are h23, c23, respectively. Similarly, the transfer function and covariance from node N1 which are input to node 520 (N3) are h13, c13, respectively.

Each node is assumed to receive modulator signals (m) from each and every modulator. For instance, it is assumed that node 520 (N3) receives modulator signals m13, m23 from modulators M1 and M2, respectively. In the model illustrated in this schematic, the modulators (M1, M2 . . . ) control the network by the frequency and power of the noise source signals 560 (m). The other nodes (N1, N2, etc.) in the network 510 can be similarly characterized as this node in this manner.

Figure 6:
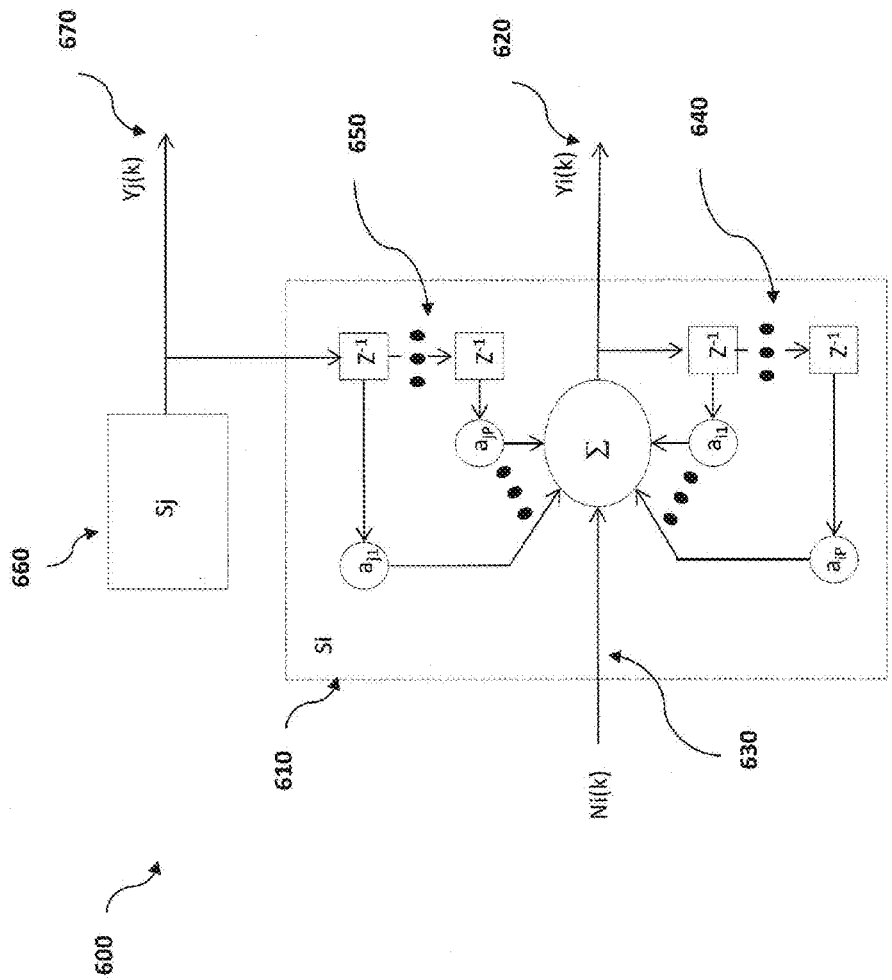
FIG. 6 is a schematic of a multivariate autoregressive process.

FIG. 6 is a schematic of one multivariate autoregressive process 600 model of the networked cortical source nodes according to an embodiment.

The autoregressive process model 600 represents the time-varying processes of a given cerebral cortex node 610 some of which specifies the output variable depends on its own previous values. Here, it is assumed that the output 620 (Yi) of the given node 610 (Si) is the sum of the random noise input 630 (Ni), the weighted consecutive prior outputs of the node output 640 (p) in a recursive feedback loop, and the weighted consecutive prior outputs 650 of a plurality of other nodes 660 (Sj), each with its own output 670 (Yk). The weights are autoregressive coefficients for the process and the number of prior outputs is determined by the order of the process. The multivariate autoregressive process may be applied to the signals for each node in the network with the results of a set of autoregressive coefficients and noise covariance for the interconnections among the nodes including the auto-recursive feedback loop. The spectral quantities for a multivariate spectral analysis are derived in the frequency domain from the estimated model coefficients and the covariance of the noise. The spectral power and directed causality measures of the multivariate signals are readily computed from the spectral transfer function and covariance. Here, in this representation of the feedback process, the time delay by element $Z^{-1}$ of the kth output sample Y is weighted by the a-th factor before summation, with the summation to the Pth order of the process.

Figure 7:
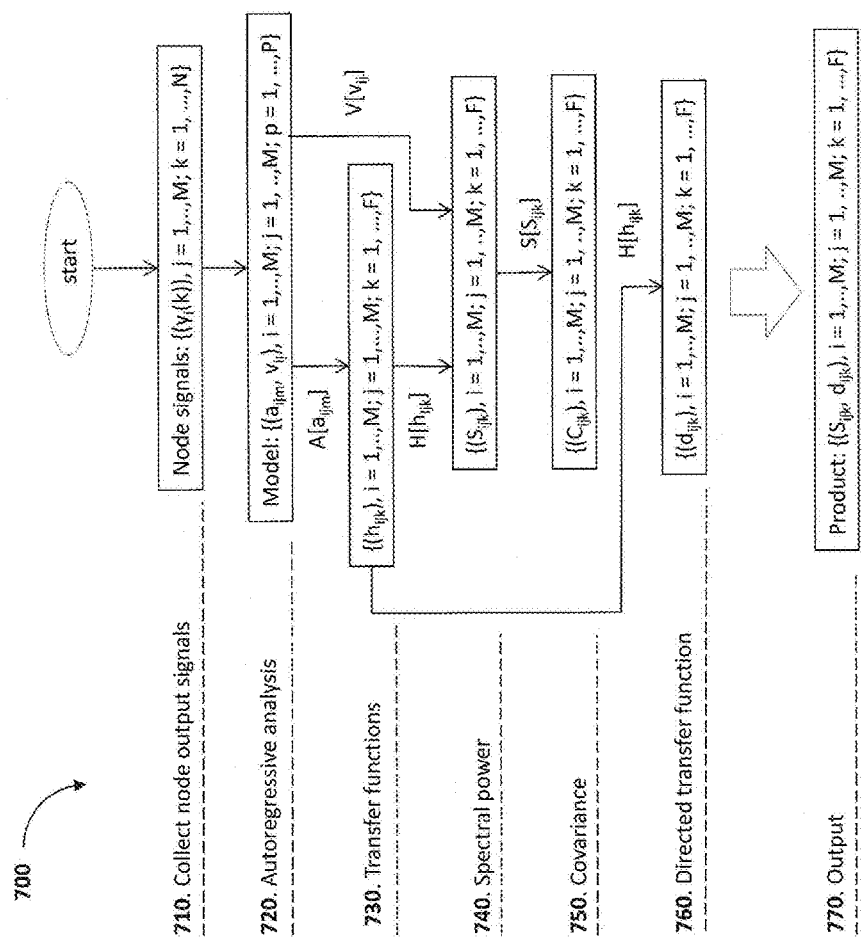
FIG. 7 is a flow chart of multivariate spectral analysis.

FIG. 7 is a flow chart showing the various steps in the multivariate spectral process 700 according to an embodiment. In brief, the process 700 comprises collecting the node output signals (y) in an electronic memory in a computing device (such as a data base) in step 710, performing the autoregressive analysis on the data in the data base in step 720 to determine the autoregressive coefficients (a) and the noise covariance (v), computing the node connectivity transfer functions (h) for the noise covariance in step 730, computing the connectivity spectral power (S) in step 740, and computing the connectivity directed transfer functions (d) in step 750. In step 760, the output of the spectral power (S) and directed transfer functions (d) are used for computing the node excitation functions described in detail shortly. Here, the transfer function (H), spectral power (S) covariance (C), and directed transfer functions (d) are functions of the nodes (M)

and the frequency (F). The output of process 700 is shown in block 770. The steps of the multivariate spectral process are in greater detail as follows:

Step 710: Node output collection—The time-wise outputs (Y) over the sample window of the selected temporal independent cortical sources are collected and stored in an electronic memory or database.

Step 720: Autoregressive process—The process is modeled here as a weighted sum of consecutive prior outputs plus a random noise, where the order determines the number of terms in the sum. The process may be extended to a multivariate process by including weighted outputs from the other nodes in the model, i.e., $E_i=\Sigma(A_j*Y_{i-j})$, where the sum is from j=0 to P, with P the order of the process model, and $Y_i$ is the vector of the K-variable process at the $i^{th}$ time, $A_j$ constitutes the K-by-K matrices of model coefficients with $A_0$ is the identity matrix, and $E_i$ is the vector of multivariate zero mean uncorrelated white noise process. The autoregressive parameter weights (A) and the noise covariance (V) may be estimated for the multivariate dataset (Y), for example, with the Levinson-Robinson-Wiggins (LWR) algorithm implemented using the Vieira-Morf Method. The optimal process order (P) can be estimated from the multivariate Akaike information criteria (AIC), a function of the noise covariance (V), the process order (P), the number of nodes (K), and the data size (N), AIC=−log(det(V))+2*P*$K^2$/N, with the optimal order value minimizing the criteria.

Step 730: Spectral transfer function—The process may be represented as a filter driven by white noise in which the filter output is modeled as a weighted sum of consecutively delayed prior outputs, where the filter order determines the number of terms in the sum. The transfer function spectral magnitude and phase are readily solved from the estimated model autoregressive coefficients as a function of frequency, i.e., $H(f)=1/(\Sigma(A_j*(cos(2\pi f\Delta)-sin(2\pi f\Delta)*i))$, where the sum is j=0 to P, the process order, and here $\Delta$ is the time sampling interval and $i=\sqrt{-1}$, complex unity; the matrix element $H_{ij}(f)$ describes the connection between the ith and jth nodes, with magnitude $|H_{ij}(f)|=abs(H_{ij}(f))$ and phase, $ph_{ij}(f)=angle(H_{ij}(f))$.

Step 740: Spectral power—The spectral power (S) is estimated from the spectral matrix of the time series data as calculated by the matrix product of the transfer function matrix (H(f)), covariance matrix (V), and transposed conjugate of the function matrix ('), S(f)=H(f)*V*H(f)'. The elements of the matrix are functions of frequency (f) and may be separated into amplitude and phase spectrums. The auto power (Pa) of a node (i) equals the corresponding diagonal element of the spectra matrix, $Pa_i(f)=S_{ii}(f)$, and is a real value magnitude without phase; while the cross power (Pc) between two nodes ($i^{th}$ and $j^{th}$) equals the off-diagonal element specified by the row and column for the nodes, $Pc_{ij}(f)=S_{ij}(f)$, a complex value having both magnitude and phase. The partial power (Pp) for a node accounts for the contribution of the other nodes to that node and is the power remaining following normalization as computed by the determinant of the spectral matrix divided by the matrix minor (determinant of the sub-matrix) for the node, $Pp_i(f)=det(S(f))/M_{ii}(f)$.

Step 750: Covariance or Directed causality—The causality functions measures the direction of influence between nodes. The Granger causality measure is based on the assertion that if a series contains information in past terms that helps in the prediction of another series, then the first series is said to cause the second series; an assumption is made that both are not caused by a third. A multivariate version of the Granger causality is the Directed Transfer Function (DTF) which expresses the ratio of influence of one node on another to the joint influences of all other nodes to that node; the normalized DTF is given by the ratio of the square of the transfer function magnitude for the two nodes divided by the sum of the squares of transfer function magnitude for that node with all other nodes, that is: $D=\{d_{ij}(f)\}$, where $d_{ij}(f)=|H_{ij}(f)|^2/(\Sigma|H_{im}(f)|^2)$, a sum from m=1 to K, with K being the number of nodes; a function of frequency with a value between zero and one.

Step 760: Generating Output—The spectral power matrix (S) and normalized directed transfer functions (D) are used to compute the excitation driving functions for the node sources.

An important aspect of the methodology is the concept of a node excitation driving function which follows from considering the network source nodes as neural network processors each with an activation function formed from weighted inputs, and a node excitation driving function that generates the partial power for the node from the activation function. The node inputs are the cross-power and auto power spectrums and the weights are the normalized transfer functions derived from the multivariate autoregressive analysis of the network.

Figure 8:
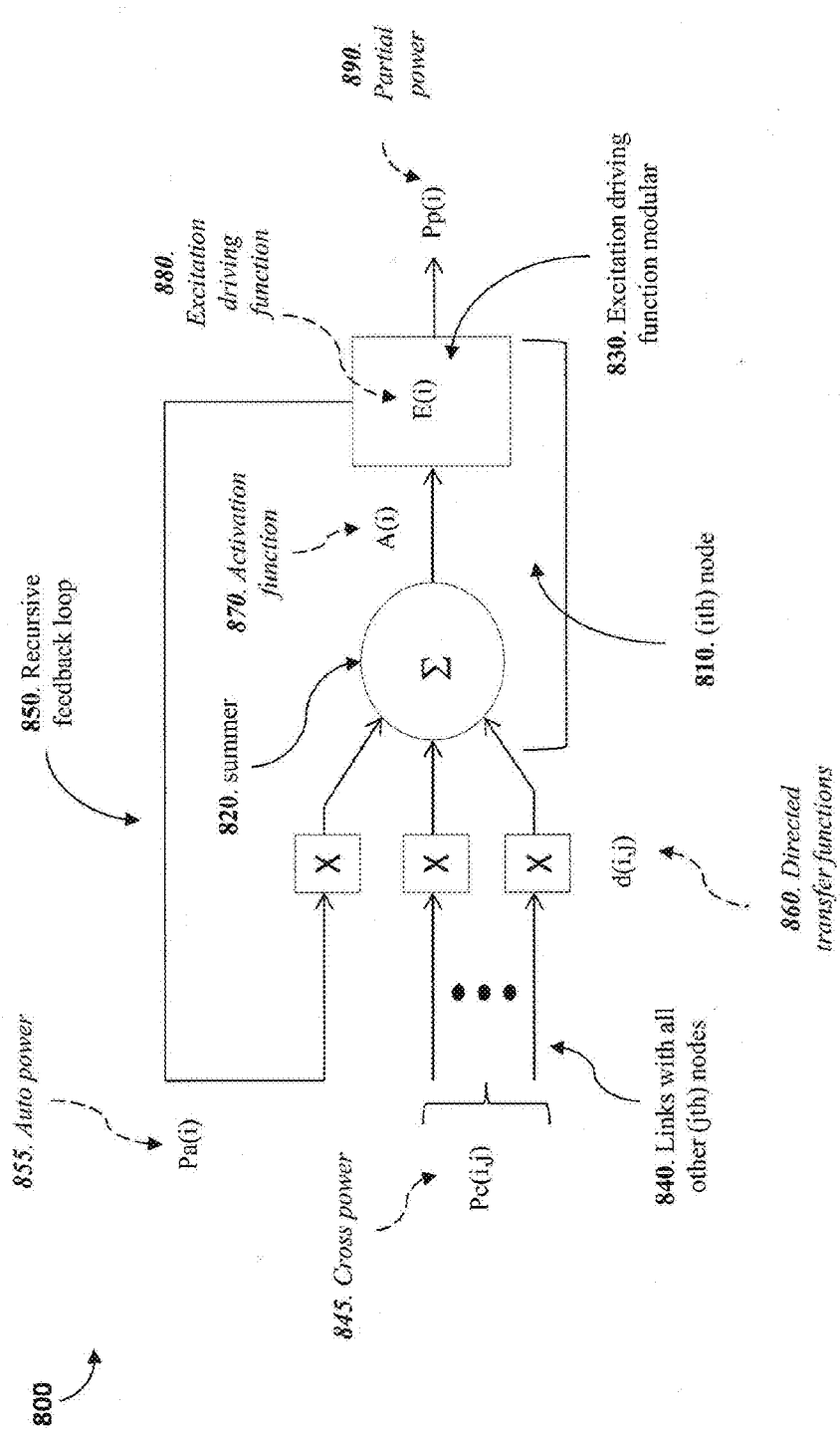
FIG. 8 is a flow schematic of node excitation driving function with relations to spectral parameters.

FIG. 8 is a schematic showing the relation 800 of the node excitation driving function to the elements of the spectral power matrix and normalized directed transfer functions that are associated with one node. The schematic shows the node 810 (ith node) of the network consisting of a summer 820 in series with an excitation driving modular 830, where the inputs to the summer 820 are the cross power outputs 845 (Sc(i,j)) from the other nodes 840 (jth node) in the network and a recursive feedback 850 from the node itself of the node auto power 855 (Sa(i)), where the powers are elements of the spectral power matrix for that node. The inputs to the summer 820 are weighted by normalized directed transfer functions 860 (d(i,j)) for the connecting links with the node including the feedback loop. The summer 820 outputs a node activation function 870 (A(i)) as the sum of the weighted inputs to the excitation driving modular that with the excitation driving function 880 (E(i)) generates the partial power 890 (Pp(i)) for the node from the activation function.

Figure 9:
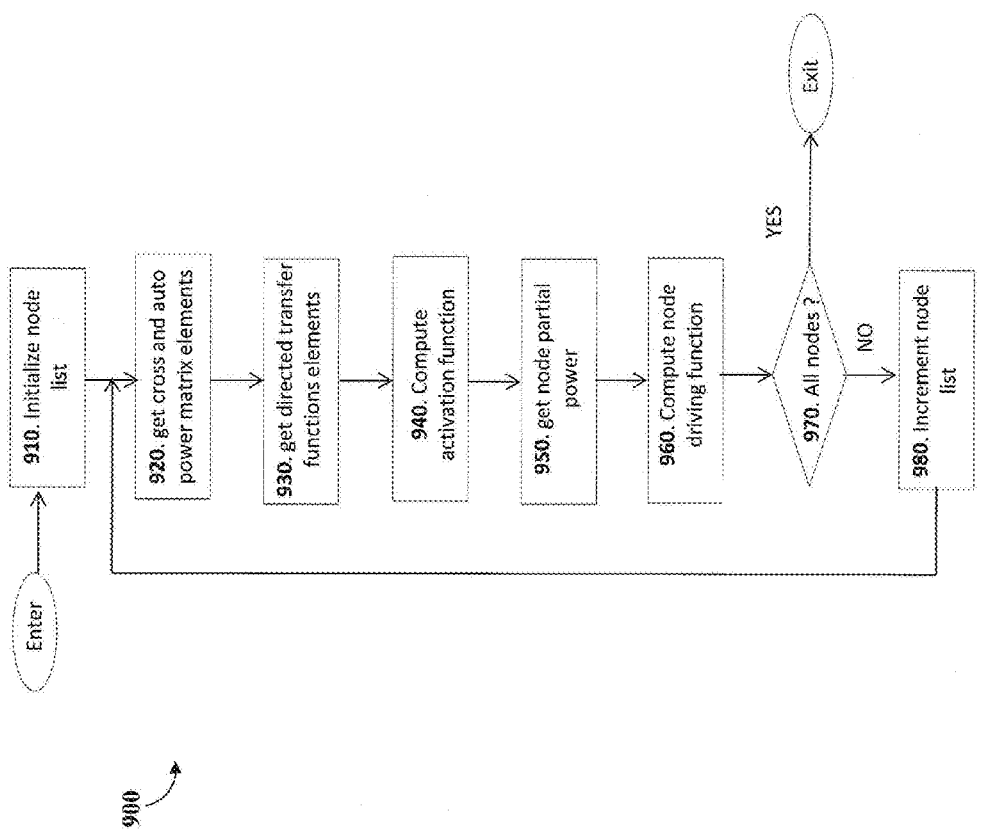
FIG. 9 is a flow chart of process for computing node excitation driving functions from spectral parameters.

FIG. 9 is a flow chart showing the steps 900 for computing the excitation driving functions for the network nodes from the power spectrum matrix and normalized transfer functions derived from the multivariate autoregressive analysis of the network. Following initialization of the network node list in step 910, the cross power and auto power elements of the spectrum matrix in step 920 for that node along with the corresponding normalized direct transfer functions in step 930 are used to compute the node activation function in step 940, and in turn the node excitation driving function is computed in step 960 from the node partial power in step 950, a process that is repeated in steps 980 for all nodes as need in step 970, where the computations are as follows:

Activation function—The weighted sum of all inputs to the node including the recursive loop where the inputs are the input spectrum ($S_{ij}(f)$), and the weights are the normalized directed transfer functions ($d_{ij}(f)$): $A_i=\Sigma d_{ij}(f)*S_{ij}(f)$, j=1:K, that is, all cross-spectrum of the inputs and the auto spectrum for the ith node.

Node excitation driving function—The partial power divided by the activation function: $D_i=Pp_i/A_i$; that is, the ratio of the partial power of the node normalized by the activating input. With this definition, the driving function is a transfer ratio of input to output spectrums that in turn, is a function of frequency.

In a further embodiment, the set of node driving functions may be used as a database for analysis of the source network activities at different levels such as the network performance state, the task nature of the network from the topological organization, and the cognitive functioning of the network.

Figure 10:
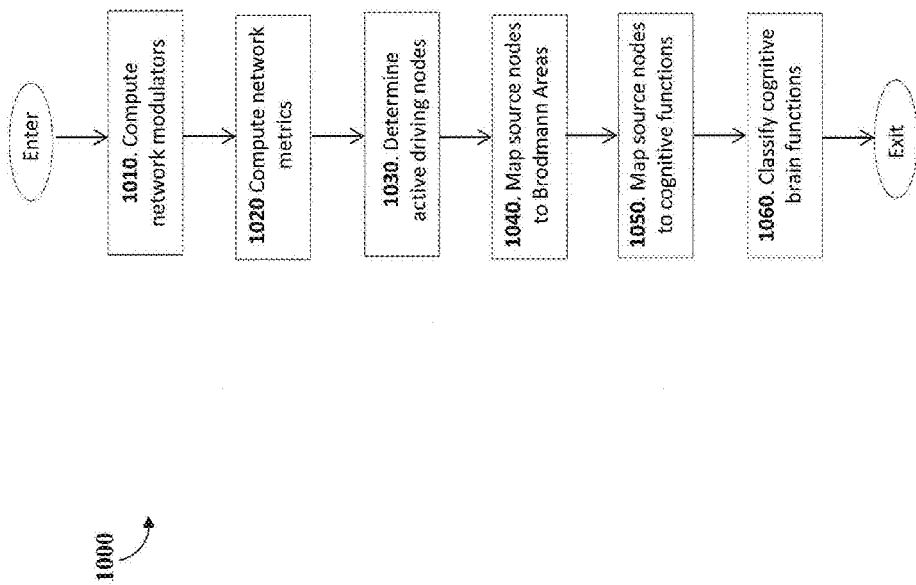
FIG. 10 is a flow chart of source network analysis using node excitation driving functions.

FIG. 10 is a flow chart of an analysis of the source network 1000 using the node excitation driving function database. The performance state of the network is set by control signals from modulator sources, and in step 1010, the modulator sources may be derived by applying blind-source separation to the database, following Principal Component Analysis to reduce the number of sources; the results are control signal power spectrums that may be analyzed for effects as a function of frequency. Other measures for the state of the network may be derived directly from the node driving function data base for comparison as a state classifier (C). Among possibilities are: (1) A grand network driving function classifier formed from the sum of the node driving functions: $C(f)=\Sigma E_i(f)$, $i=1:K$, summed across all nodes in the network, (2) a grand network driving function classifier formed from the logarithm of the product of the node driving functions: $C(f)=\Sigma \log(E_i(f))$, $i=1:K$, summed across all nodes in the network; or (3) A grand network driving function consecutive difference formed from the absolute sum of the difference between node driving functions summed over nodes and frequency: $C=\Sigma\Sigma|\Delta E_i(f)|$, $i=1:K$, $f=1:nf$.

In step 1020, the topological organization of the network functionality may be determined from the cross-correlation matrix of the node driving functions. Research has shown that cortical networks may be described as small world networks, mathematical graphs in which most nodes are not neighbors of one another, but can be reached from every other by a small number of steps; the typical distance (the number of steps) between two nodes in such scale-free networks is proportionally to the logarithm of the number of network nodes. These graphs may be classified by two independent structural features: the clustering coefficient and the average node-to-node distance (average shortest path length). Apparently, cortical networks tend to have a small average shortest path length and a large clustering coefficient since they consists of groups of shortest paths nodes centered on hub nodes with a high degree (i.e., number) of connections. Another measure is the efficiency of the network in the parallel transfer of information. These topological measures may correspond with the task nature of the network. For example, a default network would have less clustering and efficiency and be more spread out in a form of 'scale free' network; a task focused network would be spread out but with high degree and high diameter, as well as high clustering and high efficiency; and a task response network would be a 'small-world' network that has less degree and diameter, and greater clustering and efficiency. This determination may be used to cluster localized sources into a single grand source of functionality.

In the remaining steps, the cognitive processing of the network is determined, first by finding the functional activity level of the network nodes, and from that the cognitive functions as determined from the mapping of the source nodes to the brain structure, in particular, to the cortical Brodmann Areas with known brain functions. In step 1030, the active source nodes of the network are determined from the statistics of the node driving function database; in particular, from the average and variance as a function of spectrum frequency, where the more active nodes will have spectrum peaks toward the upper bounds of the confidence intervals for the dataset.

In step 1040, the nodes are mapped to cortical Brodmann Areas in Talairach head space by their locations in the 4-shell spherical head model. Brodmann Areas are regions of the cerebral cortex having the same cytoarchitectural organization of neurons (as defined and numbered by Brodmann in 1909). Again, Talairach space is a 3-dimensional coordinate system of the human brain, which map the location of brain structures using Brodmann areas as labels for both lateral and median surface brain regions as derived by Talairach and Szikla in 1967. In this process, the spherical head model may be mapped to a standard cortical space reconstructed from Montreal Neurological Institute (MNI) MRI data, and in turn to the Talairach space for location as Brodmann Areas.

Figure 11:
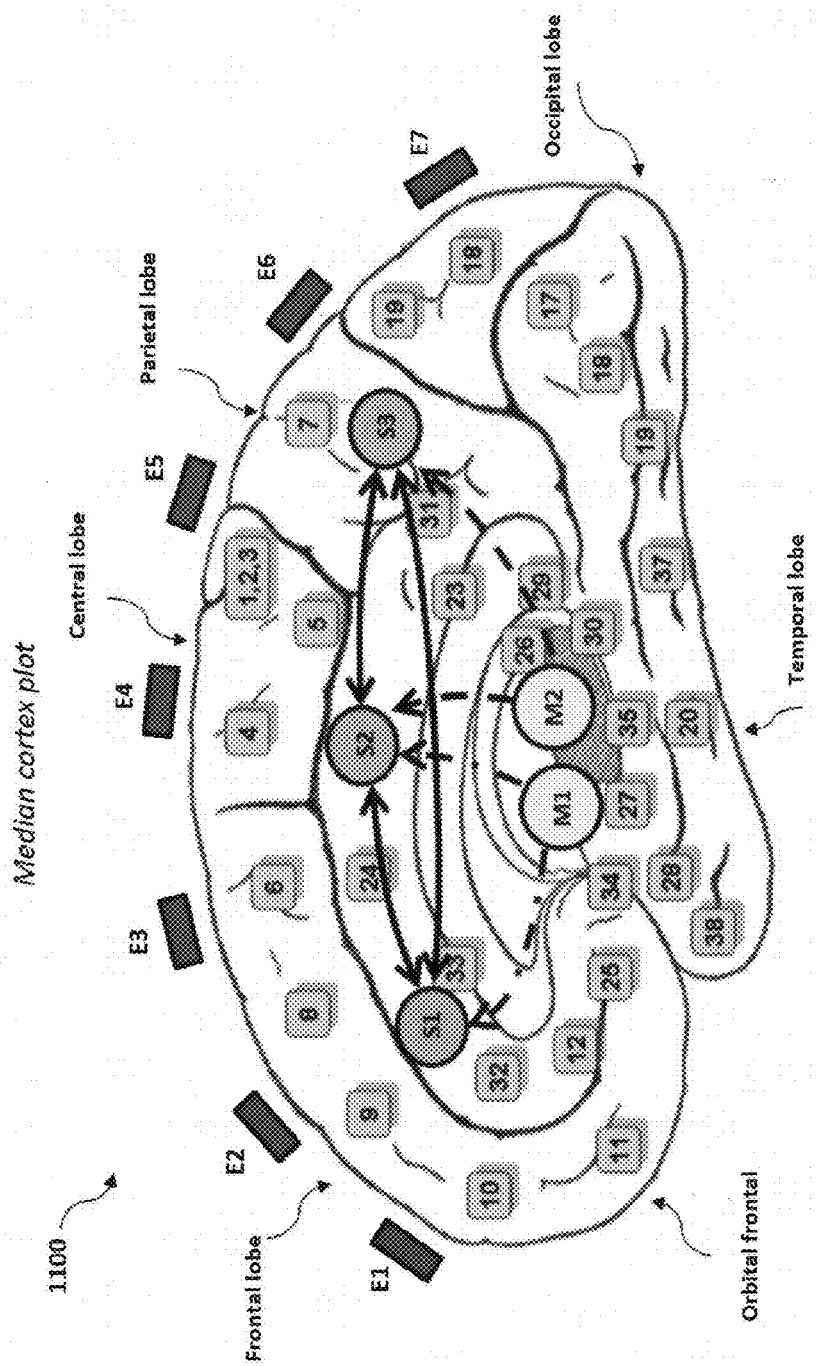
FIG. 11 is a schematic showing representative electrode sites and corresponding cortical source network with network modulators superimposed on a median view of the human cortex with numbered Brodmann Areas.

FIG. 11 is a schematic showing representative electrode scalp sites (E1-E7) and a corresponding cortical source network (S1, S2, S3) with network modulators (M1, M2), superimposed on a median view of the cortex, with numbered Brodmann Areas (BA1, BA2, BA3, etc. indicated as boxes labeled 1, 2, 3 . . . in this figure). Brodmann Areas represent known regions in the cerebral cortex in the brain believed to be responsible for discrete cortical functions.

For reference, the cortical lobes are also indicated: frontal, central, parietal, occipital, and temporal, along with the orbital frontal. In this schematic, the sources (S1, S2, S3, etc.) are mapped to the median surface; however, mapping may occur to the lateral surface as well depending upon the source locations. In the schematic figure, cerebral source S1 is mapped to BA31, S2 to BA24, and S3 to BA7, and in the mapping take on the properties of the area. Here, in the figure, the modulators M1 and M2 are shown located to the limbic region, in particular, the thalamus as sources gating the control signals. But, the locations of other modulators will likely be different.

In step 1050 (of FIG. 10), the cerebral source nodes are mapped to cortical brain functions that are known for the corresponding Brodmann Areas. There is evidence that the occipital, somatosensory, and temporal cortical lobes are organized as processors for primary sensory areas (vision: BA17; somatosensory: BA1, 2, 3; temporal: BA41 for auditory, BA43 for gustatory), and secondary sensory areas (vision: BA18; somatosensory: BA5; temporal: BA42 for auditory), association areas (vision: BA19; somatosensory: BA7; temporal: BA22), along with multiple association areas in the parietal and temporal (BA20, 21, 15), which in turn lead to the frontal lobe for evaluation (BA9, 10, 11, 12), with pre-motor frontal eye-fields for directed vision (BA8), and secondary motor (BA6) and primary motor (BA4) for action. Specialized temporal and frontal areas process language understanding (BA39, 40) and generation (BA44, 45). These functions may be specialized further by cortical hemisphere. In addition, the anterior cingulate is believed involved in error detection (BA24, 32) and the posterior cingulate in emotion (BA23, 31). Further involved are the limbic system regions of entorhinal cortex (BA34), perirhinal cortex (BA35), and the ectorhinal area (BA36) of the perirhinal cortex, among others for spatial memory and orientation. Of course, this is not a complete rendition of all brain areas and associated functions. Although these are coarse representations of functions considering the size of the Brodmann Areas probably each containing millions of neurons, the mapping provides a basis for considering the general nature of cortical processing.

In step 1060, the cortical brain functions of the source node network are mapped to a cognitive processing network for classification of attention to a task. In this process, the modulator sources are a measure of the strength of attention, while the network topology corresponds to the cognitive involvement. As has been mentioned above, a default network corresponding to self-referral has less clustering and efficiency and is more spread out in a form of 'scale free' network; a task focused network would be spread out but with high degree and high diameter, as well as high clustering and high efficiency; and a task response network would perhaps be a 'small-world' network that has less degree and diameter, and greater clustering and efficiency. Further, the active sources driving the network determine the state of task attention from the corresponding Brodmann Areas as to sensory processing (and as visual or auditory), association, evaluation and motor involvement.

Example Demonstration of the Innovative Methodology

The aforementioned methodology was applied to the scalp electroencephalogram data collected from fourteen subjects in a temporal discrimination experiment conducted at the U.S. Army Research Laboratory. The initial data was reported by Hairston W D, Letowski T R, McDowell K [2010] in a report titled "Low-level auditory processing as a predictive tool for within- and cross-model performance," presented at the 27$^{th}$ Army Science Conference, Orlando, Fla., in which the subjects judged which of two consecutive stimuli were longer in duration. In one trial, the stimuli were auditory while in another they were visual; a neutral baseline trial without a stimulus was used as control. One of the stimuli of the consecutive pair was randomly set at 250 ms while the other was 400 ms in duration; they were separated by a 250 ms interval, resulting in a 900 ms time period for the test stimulus on-set to the response stimulus off-set. The subjects had two seconds to respond by button push as to which was longer.

Figure 12:
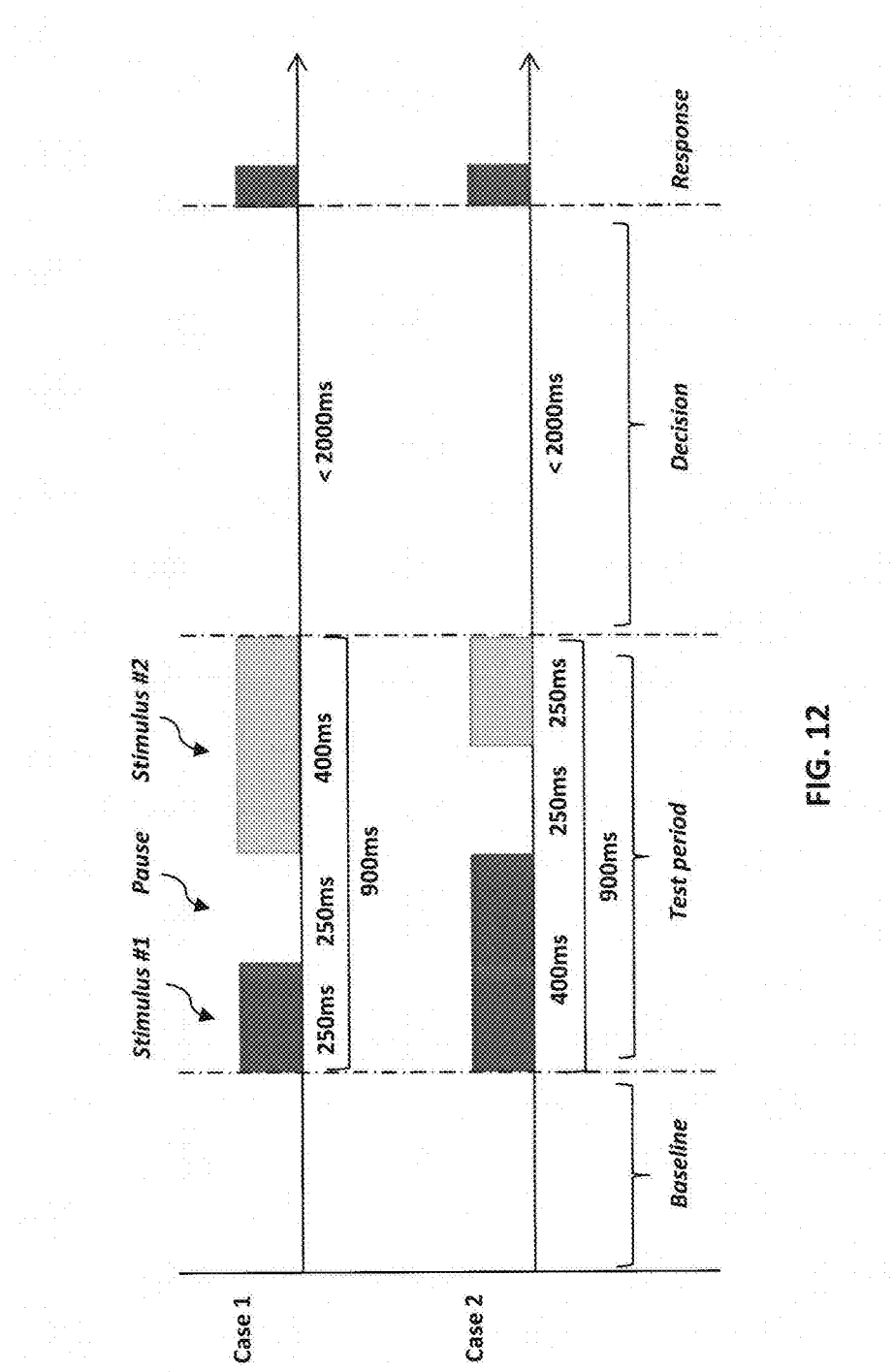
FIG. 12 is a schematic of experimental study task timeline.

FIG. 12 is a schematic showing these events for a judgment task comprising a preceding baseline, the test time period of the test stimulus, a pause, and the response stimulus, and a decision period followed by manual response. The inter-stimulus interval (ISI) was varied randomly from 3 to 12 seconds. During the trials, the subjects were subjected to a 'standard' 100 ms, 220 Hz pure tone presented every 450 ms (3% were an 'oddball' 247 Hz tone presented randomly); subjects were told to ignore the background tones. The judgment tasks were repeated in two trial sets for each type of stimulus, including the neutral. The scalp electroencephalogram data was collected using a 64-channel Biosemi active electrode bio-potential system, sampled at 8.192 kHz (for a separate auditory response analysis), and analog filtered at 0.1-4 kHz with external reference set to bilateral earlobes. The scalp electrodes were in an extended International 10-20 Electrode system configuration; additional channels collected vertical and lateral electro-ocular potentials (EOG) for both eyes, as well as event markers for the stimuli onsets from the experimental computer. In preparation for analysis of the judgment tasks, the data was digitally low-pass filtered with a cut-off frequency of 256 Hz and down sampled to 512 Hz.

Data Reduction and Analysis Methodology

Figure 13:
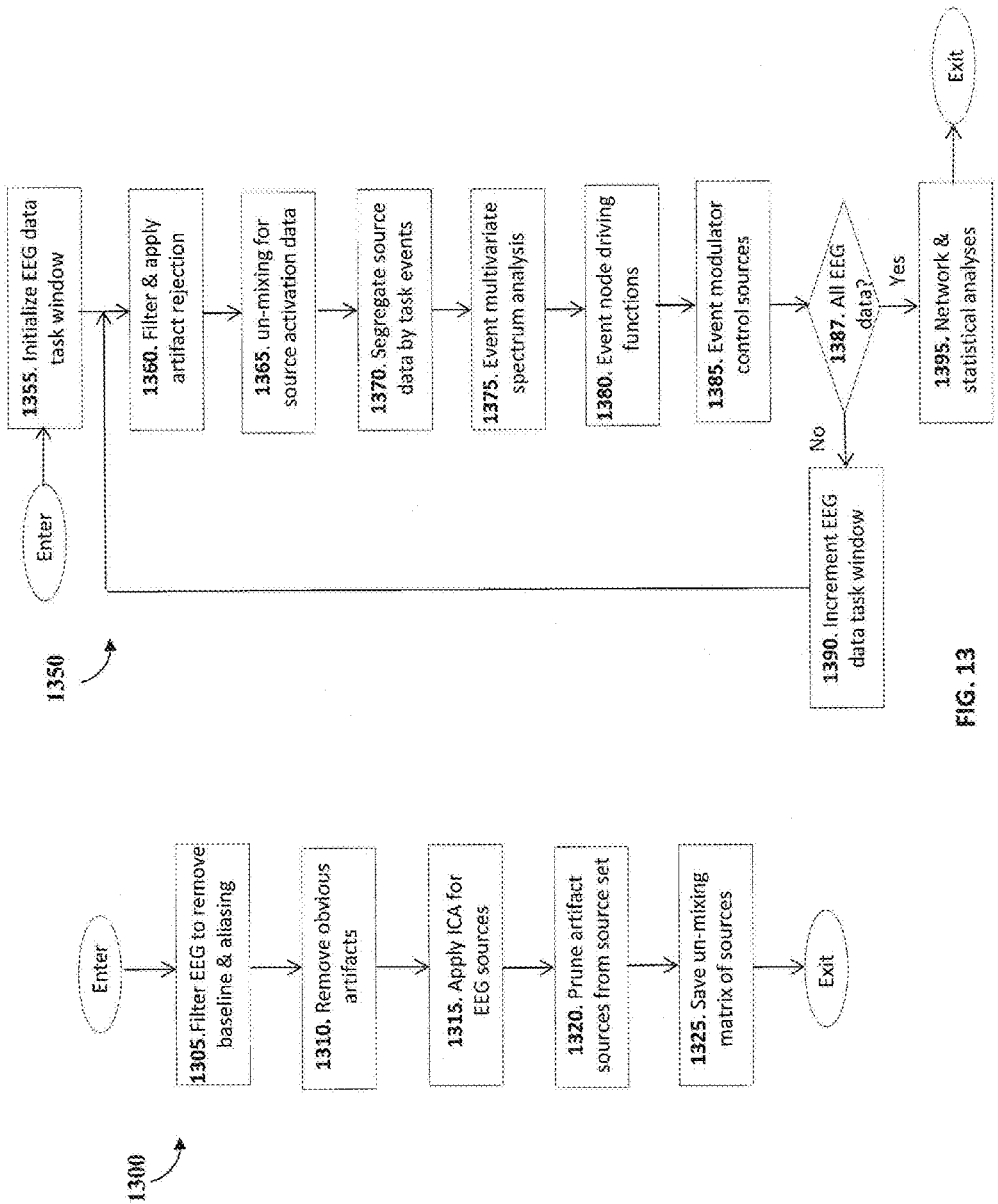
FIG. 13 is a flow chart of data processing for study.

For analysis by the innovative methodology, the scalp electroencephalogram dataset was processed to compute independent cerebral sources, from which the node excitation driving functions and corresponding modulators were computed for network and statistical analysis. As shown in the flow chart of FIG. 13, the process was performed in two stages, with the first a pre-processing stage 1300 to compute the cerebral sources for the EEG data base by first filtering to remove baseline and preclude aliasing (for second stage down-sampling) in step 1305, removal of obviously extreme artifacts from the EEG in step 1310, application of independent component analysis for the scalp voltage sources based on kurtosis of the amplitude probability density functions in step 1315, the pruning of sources of remaining artifacts from the source set in step 1320, and the saving of the resulting un-mixing matrix for the cerebral sources in step 1325.

In the second processing stage 1350, the node driving functions and resulting modulators were computed for the sources from the EEG database for the test time period windows. In this stage, the task windows were determined in step 1355 from the event marker channel, and the isolated EEG segments were filtered and obvious artifacts removed in step 1360 as in the pre-processing stage, the source activation signals were computed from the resulting EEG segments using the un-mixing matrixes of the pre-processing stage for the sources in step 1365, the activation signals were grouped by the task events in step 1370, the multivariate spectrum analysis was computed for the event activation segments following down-sampling in step 1375, the node driving functions were accordingly computed for the sources from the spectrum measures in step 1380, and in turn the modulators for the source network in step 1385. This was repeated in step 1390 for all EEG test period windows in step 1387, and the resulting functions parameterized for network and statistical analysis in step 1395. Of further interest for analysis are the differences between the driving functions by events and those between the modulator signals by events as well. These steps are described in detail in the following.

Pre-Processing Stage 1300—

The data set was processed by an automated computer program incorporating script files calling EEGLAB Matlab open source routines available for electrophysiological signal processing, as follows:

The data was high-pass filtered using the 'eegfilt.m' routine to remove baseline drift (1 Hz cutoff), and low-pass filtered with a cut-off frequency of 64 Hz (needed to preclude aliasing in down-sampling to a 128 Hz sampling rate in the second stage to facilitate the application of the autoregressive analysis).

The data was epoched into consecutive 0.5 sec intervals ('epoch.m') and the baseline removed ('rmbase.m').

Artifacts were rejected by epochs using amplitude threshold limits (eegthresh.m'), trend limit (rejtrend.m'), improbable joint-probability (jointprob.m'), and improbable probability density distribution by kurtosis (rejkurt.m'), with the trials selected for rejection by the different methods 'OR'ed together and removed from the database.

An independent component analysis for independent sources was performed on the remaining epochs using the EEGLAB 'runica.m' iterative routine based on the kurtosis probability density distribution, thereby resulted in a component source set and an associated component weights matrix ('EEG.icaweights') and sphere whitening matrix ('EEG.icasphere').

The independent components sources were located as dipoles in the standard MRI Spherical head model (standard_BESA/standard-10-5-cap385.elp), using the EEGLAB DIPFIT2 routines.

Extraneous component sources were pruned by location, spectra, and variance using laboratory written Matlab routines on the following basis:

a. Location—Source spherical head locations on the skull (electrode site) or outside the head (EMG source), below the cranial (subcortical sources, EMG source), or in the frontal eye-region (ocular muscle source);

b. Spectra—Source spectra not fitting the expected spectra for an EEG source as being convex decreasing with frequency (approximating 1/frequency$^2$), and with excessive power in the low frequencies below 2 Hz (eye-movements) or in the high frequencies above 30 Hz (muscular movements) compared to the middle frequencies 5 Hz to 30 Hz, especially if peaks in the theta, alpha, or beta range are missing; and c. Variance—Sources with minimal variance (power) are dropped from the source set; in this study, the source set was limited to the top ten acceptable sources as measured by power variance; where the pruning process results in a rejection file ('rejectfile') being set for the sources that are pruned by these methods.

An un-mixing matrix was computed for generating the cerebral source component waveforms from the scalp recordings, where the un-mixing matrix is the matrix product of the component weights matrix ('EEG.icaweights') and sphere whitening matrix ('EEG.icasphere') for the data set.

Second Processing Stage 1350—

The data set was processed by an automated computer program with laboratory written Matlab routines using the original data set, as follows:

The data was high-pass filtered (here using the 'eegfilt.m' routine) to remove baseline drift (1 Hz cutoff), and low-pass filtered with a cut-off frequency of 64 Hz to preclude aliasing in the later operation of down-sampling to a 128 Hz sampling rate.

The data was segmented by task time window event markers into a pre-test window baseline, the test stimuli segment, and the response segment for each of the tasks in the data.

The event segments were processed for obvious artifacts as in the first-stage using amplitude threshold limits, trend limits, improbable joint-probability, and improbable probability density distribution by kurtosis; segments with artifacts were removed from further study.

Source activation signals were computed for the event segments using the source set and corresponding un-mixing matrixes from the first stage.

The segment source activation signals were down-sampled to a 128 Hz sampling rate, the base and trend removed, and amplitude normalized by the standard deviation of the resulting segments in preparation for spectrum analysis.

Autoregressive coefficients and noise variance were computed for the source set from the segment activation signals by multivariate autoregressive analysis.

The segment spectrum matrix was computed for the source set from the transfer functions (derived from the autoregressive coefficients) and noise covariance resulting for the segment activation signals.

The source node driving functions were computed from the cross and partial power spectrums, and the directed transfer functions for the sources.

A set of parameters for the node driving functions was computed from the coefficients of a polynomial curve used for smoothing the function waveform (using 'polyfit.m').

A function difference measure was computed as the absolute difference in consecutive event polynomial curve smoothed functions summed over the spectrum frequency.

The source network modulators were derived from the node driving functions by independent component analysis following principal component analysis of the function data; the modulator activations were computed by applying the modulator un-mixing matrix to the driving function spectrums.

A set of parameters for the modulator activations was computed from the coefficients of a polynomial curve smoothing the activation waveform.

A modulator difference measure was computed as the absolute difference in consecutive event polynomial curve smoothed activations summed over the spectrum frequency.

Statistical Analysis—

The source nodes were matched across experiment participants to form equivalent variable sets for statistical analysis from the ranking order of the independent component signal power variance.

The polynomial fit coefficients used for smoothing the modulators were analyzed in a linear model multivariate statistical test on the experiment fixed factors of condition (visual, auditory, neutral), trial (first, second), and event (baseline, stimulus, response), with subject dummy variables included for repeated measures. A similar test was done for the node driving functions coefficients.

These test were repeated for the task events as a fixed factor, where the baseline event was used for the neutral condition since no stimulus was presented in this condition as a control; thereby accounting for the condition by event interaction inherent in the original experimental design.

The difference measures for the modulators and for the node driving functions were statistically analyzed separately for the effects of the experimental fixed factors of condition, trial, and event, and of the task event as a fixed factor.

The Holm-Bonferroni simultaneous test procedure was used to control for the family-wise Type-I error by partitioning the overall alpha level of 0.05 among the family of separate tests.

Cerebral Network Analysis—

The network parameters for the cerebral sources as a node network were computed from the node driving functions, as follows:

Smoothed node driving functions were computed for the task events using the polynomial fit coefficients;

The spectral cross-correlations were computed for the smoothed functions by spectrum lag (one-sided), using the non-normalized sliding inner-product in the spectrum plane;

Cross-correlation matrixes were computed from the average correlations for each node combination;

Threshold values were computed for the cross-correlation matrixes using the grand mean value and standard deviation for the matrix (threshold=mean+1.96*std), and thresholded matrixes were segmented as 'background noise' elements for those values below the threshold and 'object' elements for those values above the threshold; and The thresholded correlation matrixes were used to compute the properties of the nodes as a network, comprising the node degree, clustering coefficient, shortest interconnection length, and efficiency.

Spectrum Measures

Figure 14:
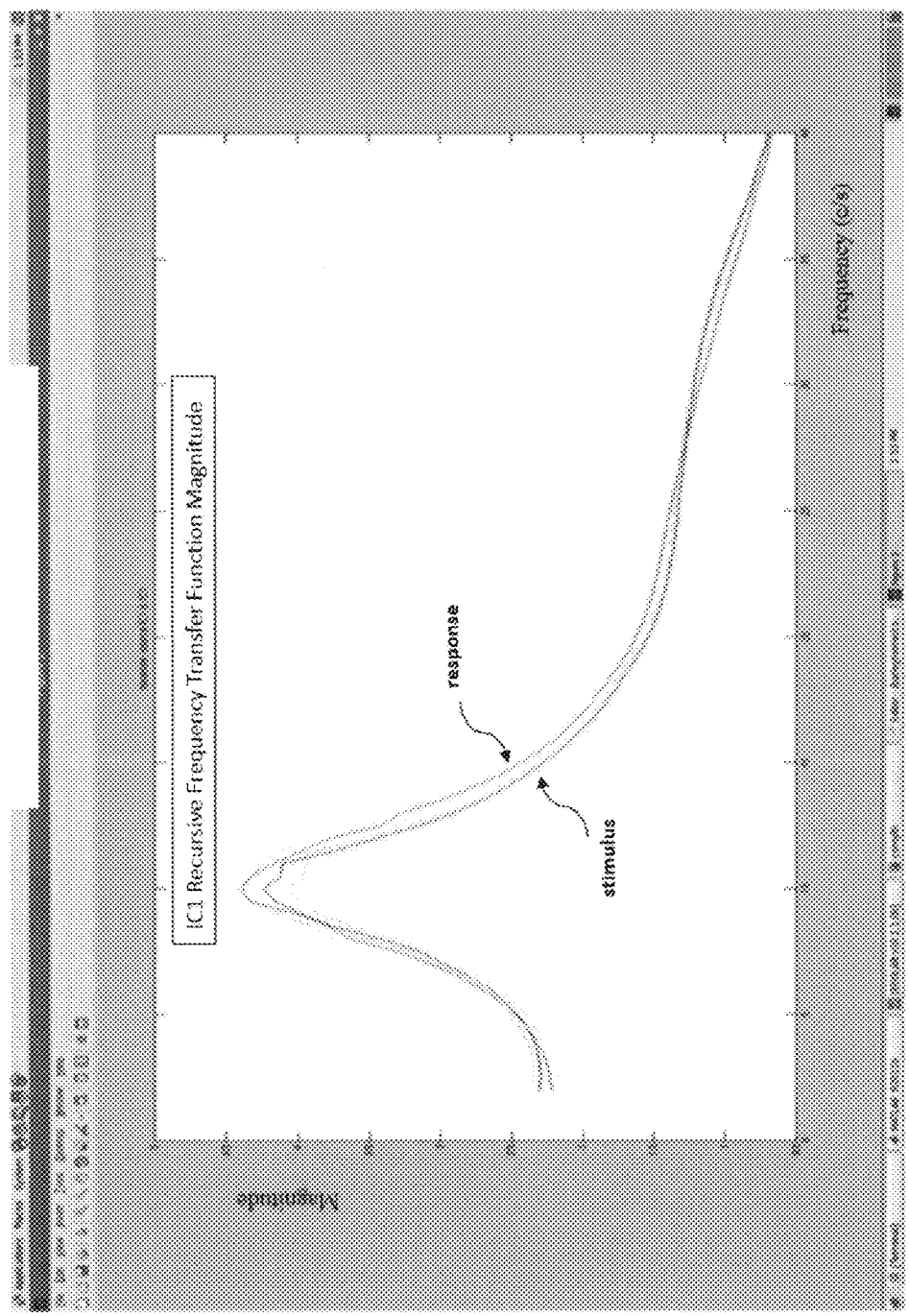
FIG. 14 shows a source recursive frequency transfer function magnitude.
Figure 15:
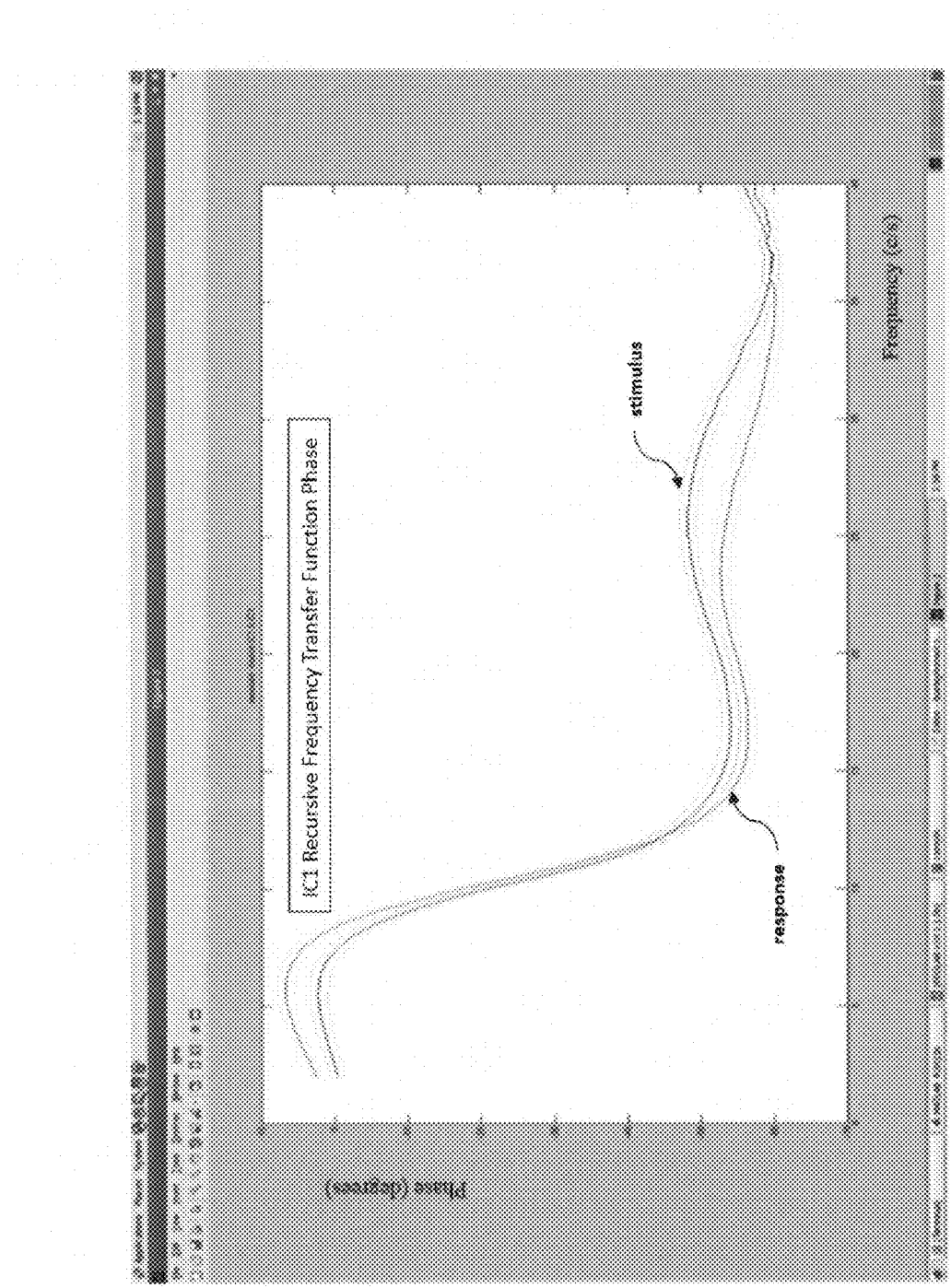
FIG. 15 shows a source recursive frequency transfer function phase.
Figure 16:
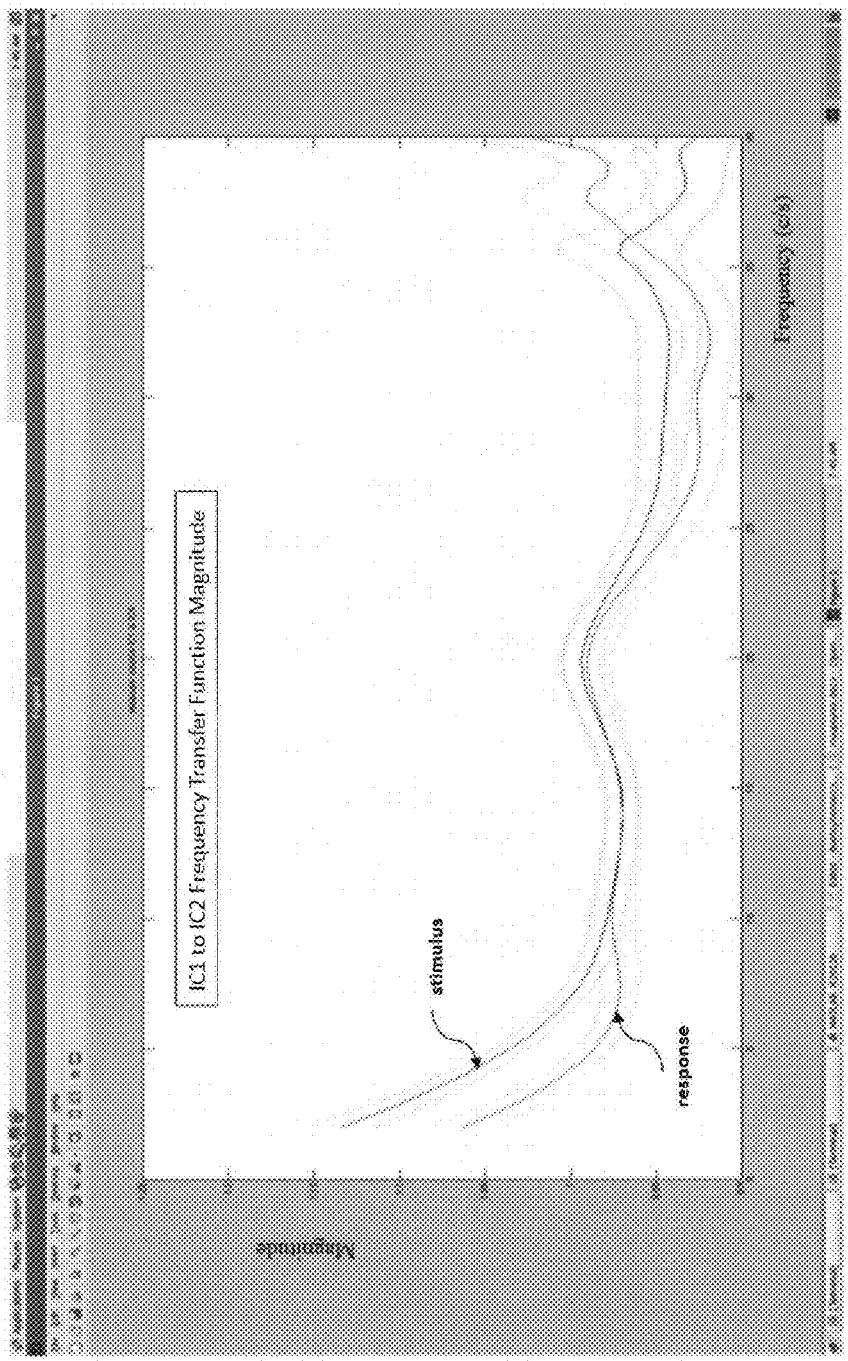
FIG. 16 shows a source to second source connectivity frequency transfer function magnitude.
Figure 17:
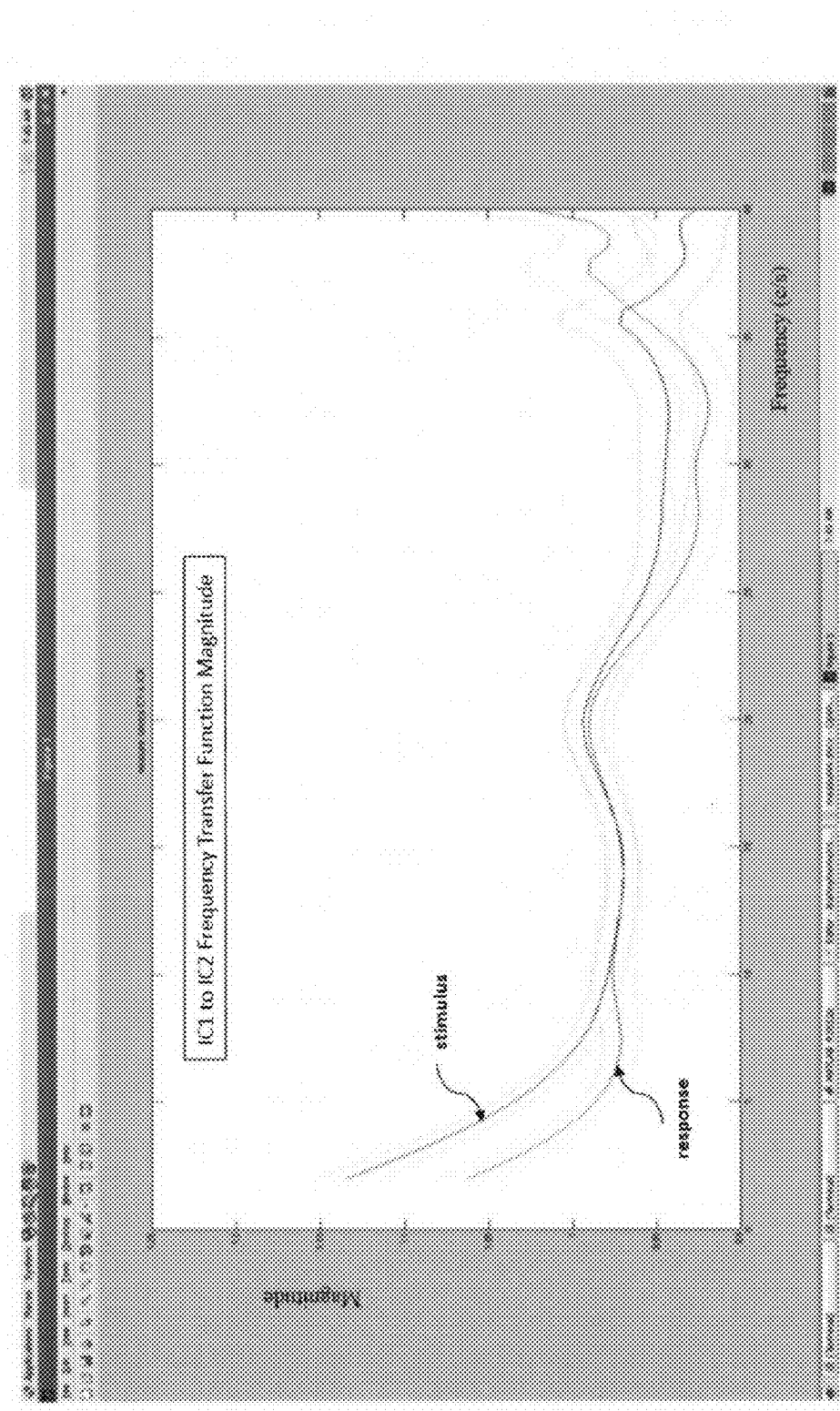
FIG. 17 shows a source to second source connectivity frequency transfer function phase.

For reference, examples of spectrum measures resulting from the multivariate spectrum analysis of the source activations are provided in the following spectrum plots for two cerebral sources (selected by activation strength), of one subject in the visual trials. All plots are for the stimulus and response events plotted from 0 to 40 Hz, unless indicated elsewise. Considering the transfer functions computed from the autoregressive coefficients, the transfer function magnitude and phase frequency plots for the recursive loop of the first source (IC1: strongest source) are shown in FIG. 14 and FIG. 15, respectively. Further, the transfer function magnitude and phase frequency plots for the connectivity from the first source (IC1) to a second source (IC4) are shown in FIG. 16 and FIG. 17, respectively. The figures show practically the same spectrum for the first source in the stimulus and response events, with the recursive loop transfer function strongly peaked (maxima) at about 10 Hz and negative phase, while the connectivity transfer function is practically flat with unity magnitude and zero phase. For this source, the recursive loop is amplifying at about 10 Hz feeding the noise power back to the source, while the connectivity acts as a 'short', passing noise power without effect.

Figure 18:
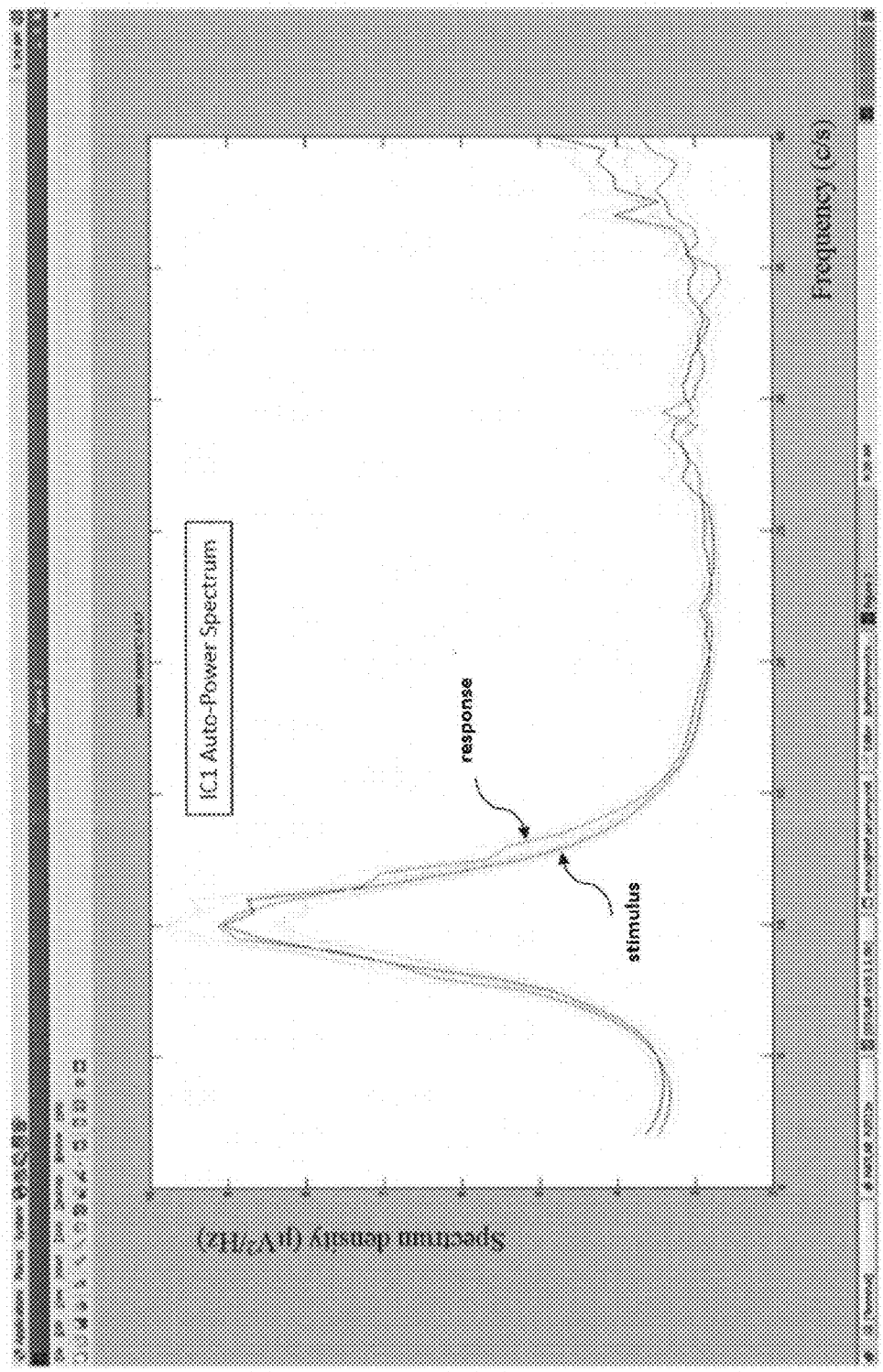
FIG. 18 shows a source auto-power frequency spectrum.
Figure 19:
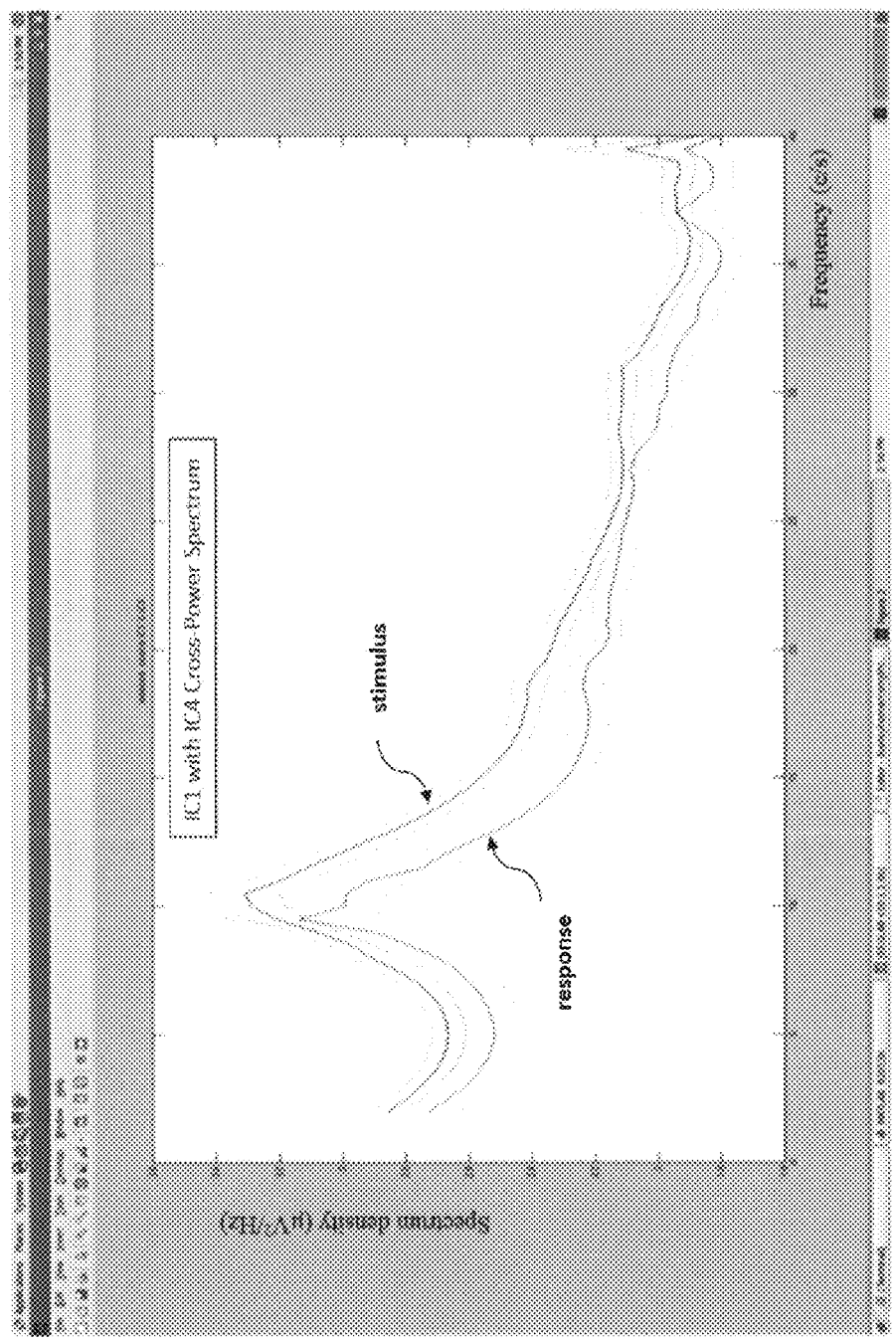
FIG. 19 shows a source to second source connectivity cross-power frequency spectrum.

Considering the power spectrums computed from the transfer functions and the noise covariance, the auto-power frequency spectrum for the first source is plotted in FIG. 18, while the cross-power spectrum for the connectivity from the first source to the second source is plotted in FIG. 19. The auto-powers for the first source are practically the same for the stimulus and response events, both peaking in power spectrum density at about 10 Hz. The cross-powers for the source connectivity are similar, both peaking about 10 Hz, but the power spectrum density is much more for the stimulus event than for the response event.

Figure 20:
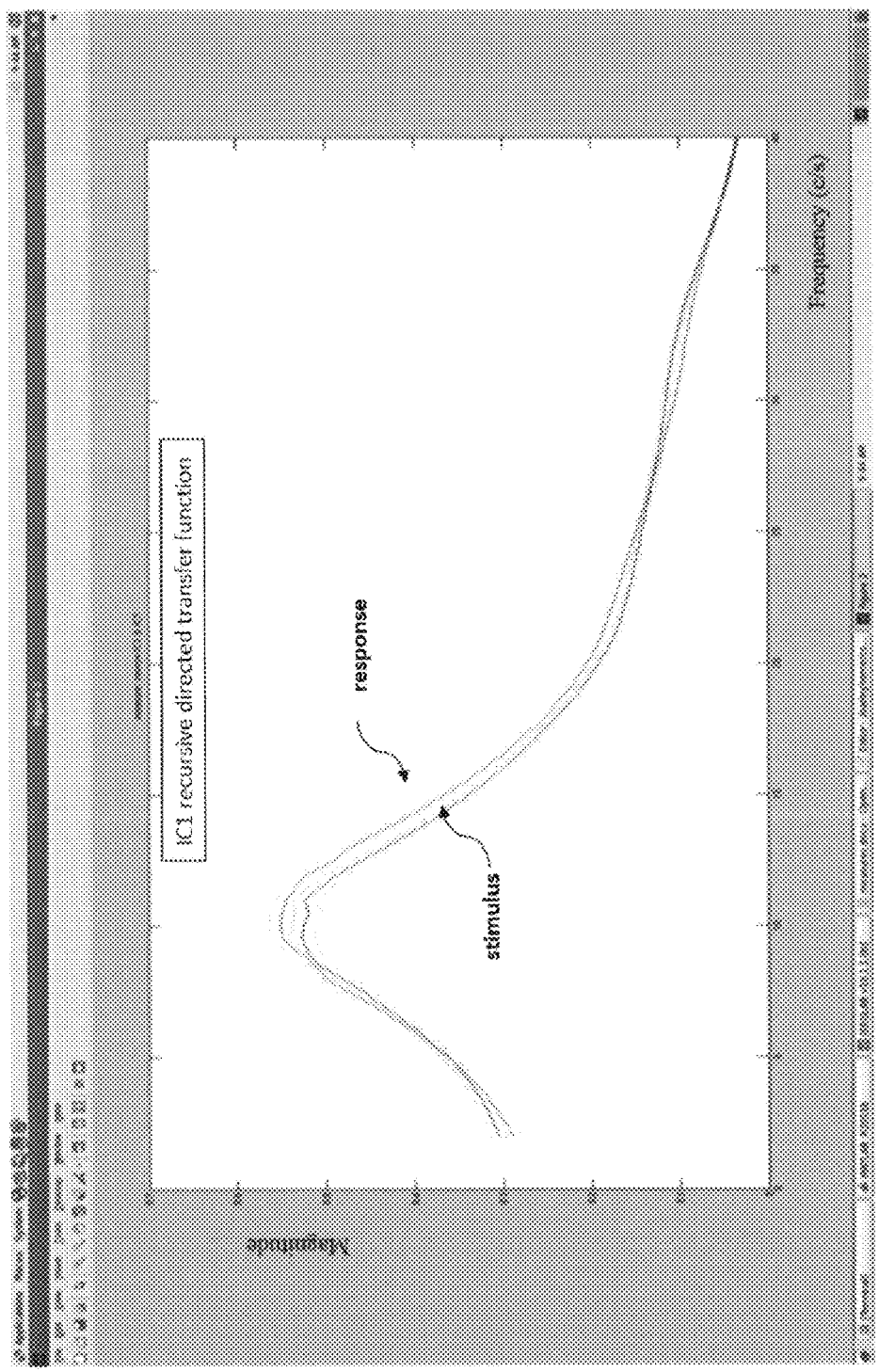
FIG. 20 shows a source recursive normalized directed transfer function.
Figure 21:
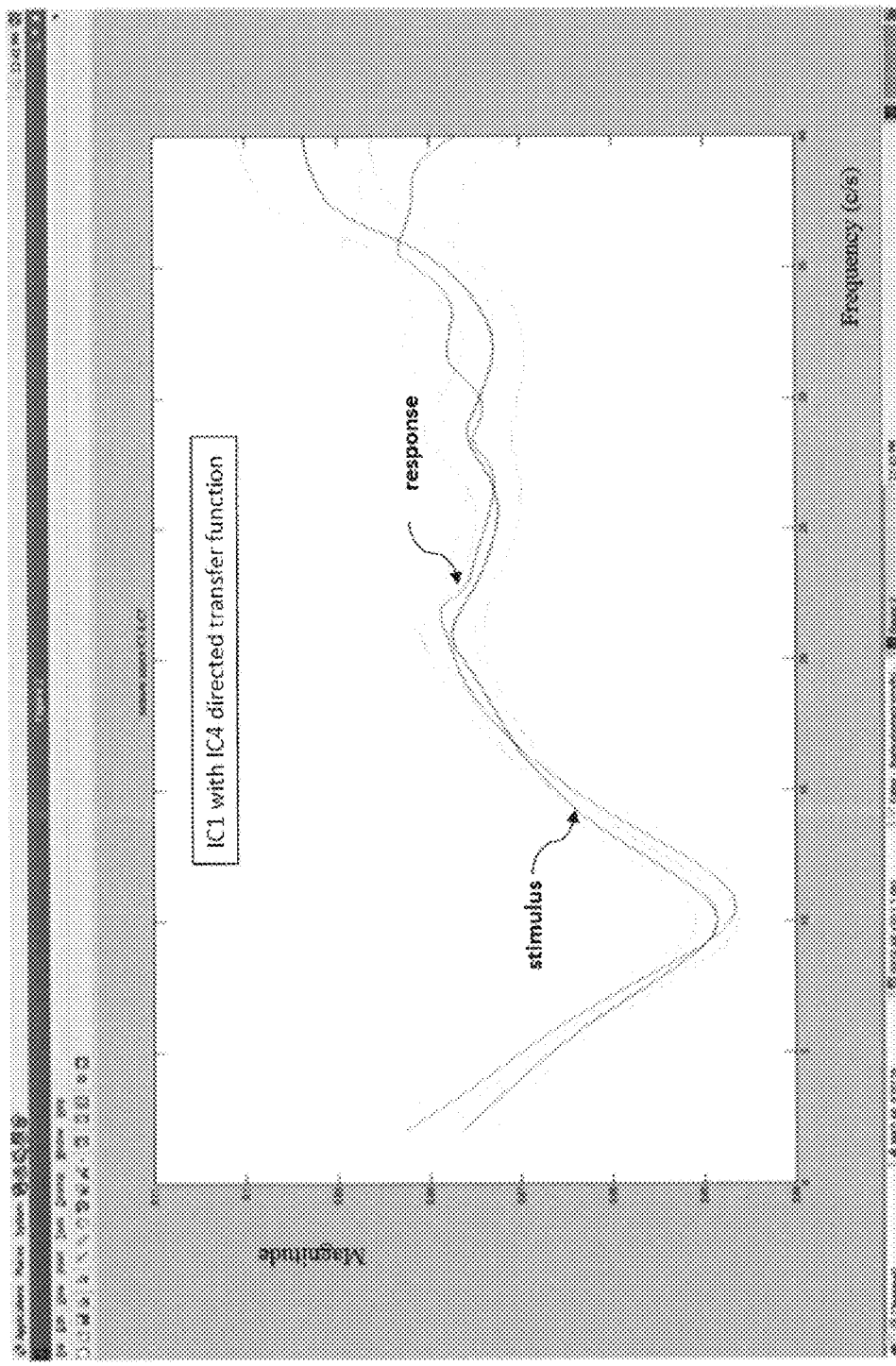
FIG. 21 shows a source to second source connectivity normalized directed transfer function.

Next considering the normalized directed transfer functions, the function for the recursive loop of the first source is plotted in FIG. 20, while that for connectivity from the first source to the second source is plotted in FIG. 21. The directed transfer functions for the recursive loop are practically the same for both the stimulus and response events with a peak at about 10 Hz; the directed transfer functions for the source connectivity are also practically the same, except here the functions have a valley (minima) at about 10 Hz. The plots are nearly mirror images with the transfer functions for the recursive loop amplifying at about 10 Hz, while those for the source connection suppressing power at that frequency.

Figure 22:
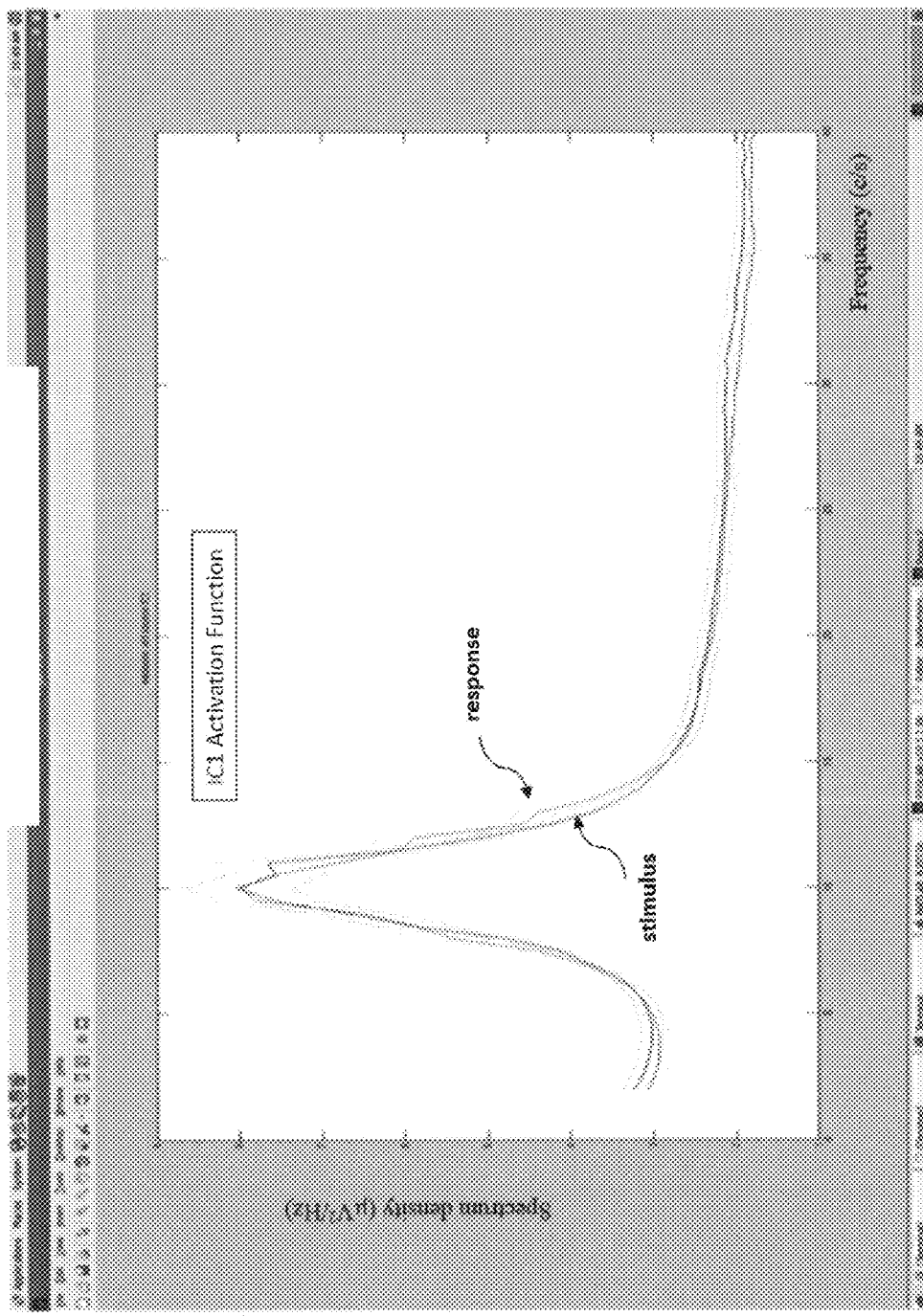
FIG. 22 shows a source activation function.
Figure 23:
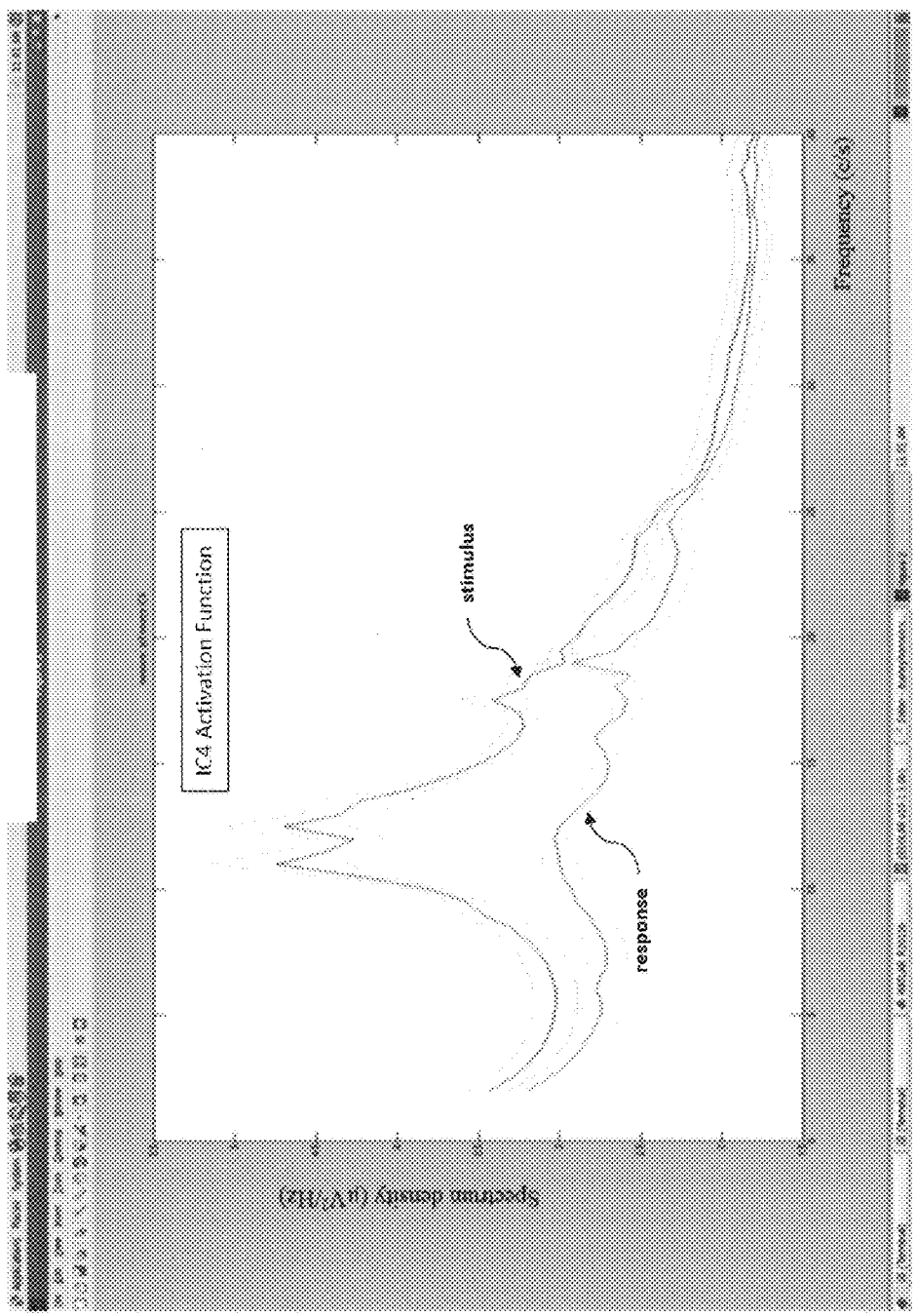
FIG. 23 shows a second source activation function.

Considering the source activation function, the function for the first source is plotted in FIG. 22, while that for the second source is plotted in FIG. 23. The activation functions for the first source are practically the same for both the stimulus and response events, peaking at about 10 Hz; while the activation functions for the second source are dissimilar, with that for the stimulus event peaked at about 10 Hz and that for the response flat.

Figure 24:
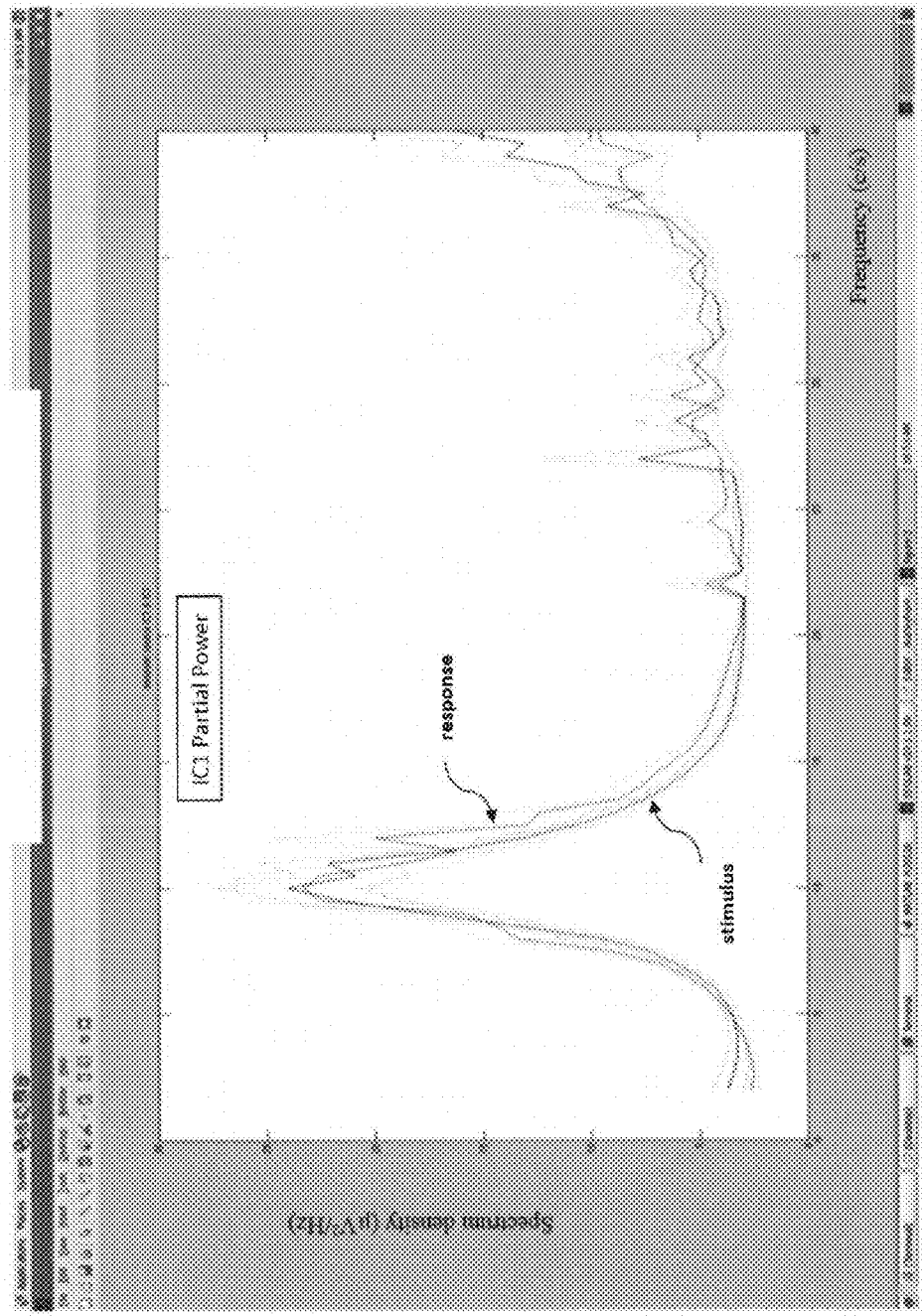
FIG. 24 shows source partial power.
Figure 25:
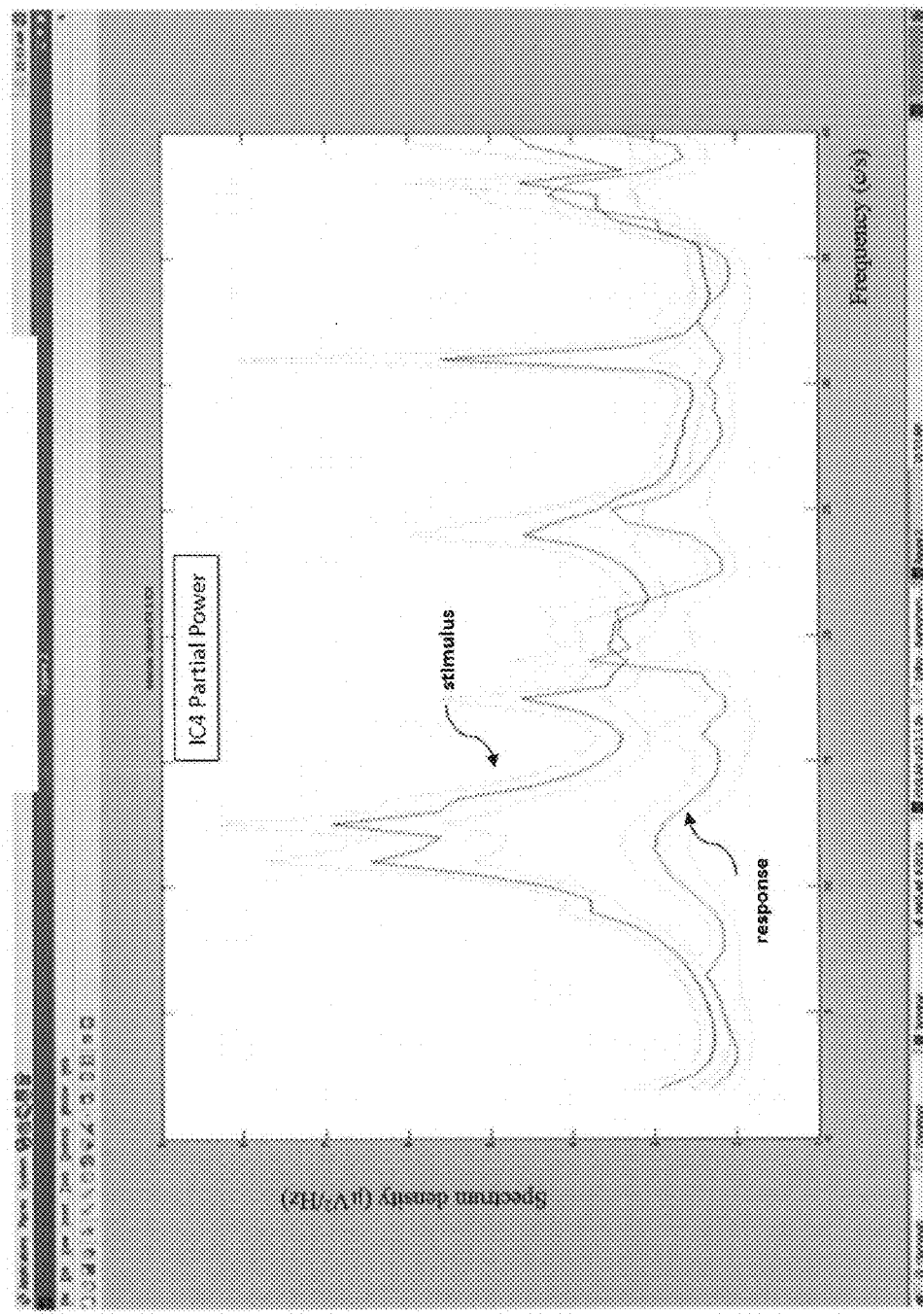
FIG. 25 shows second source partial power.

Looking at the source partial power, the power for the first source is plotted in FIG. 24, while that for the second source is plotted in FIG. 25. The partial power for the first source are practically the same for both the stimulus and response events, peaking at about 10 Hz; while the partial powers for the second source are dissimilar, with that for the stimulus event peaked at about 10 Hz and that for the response flat.

Figure 26:
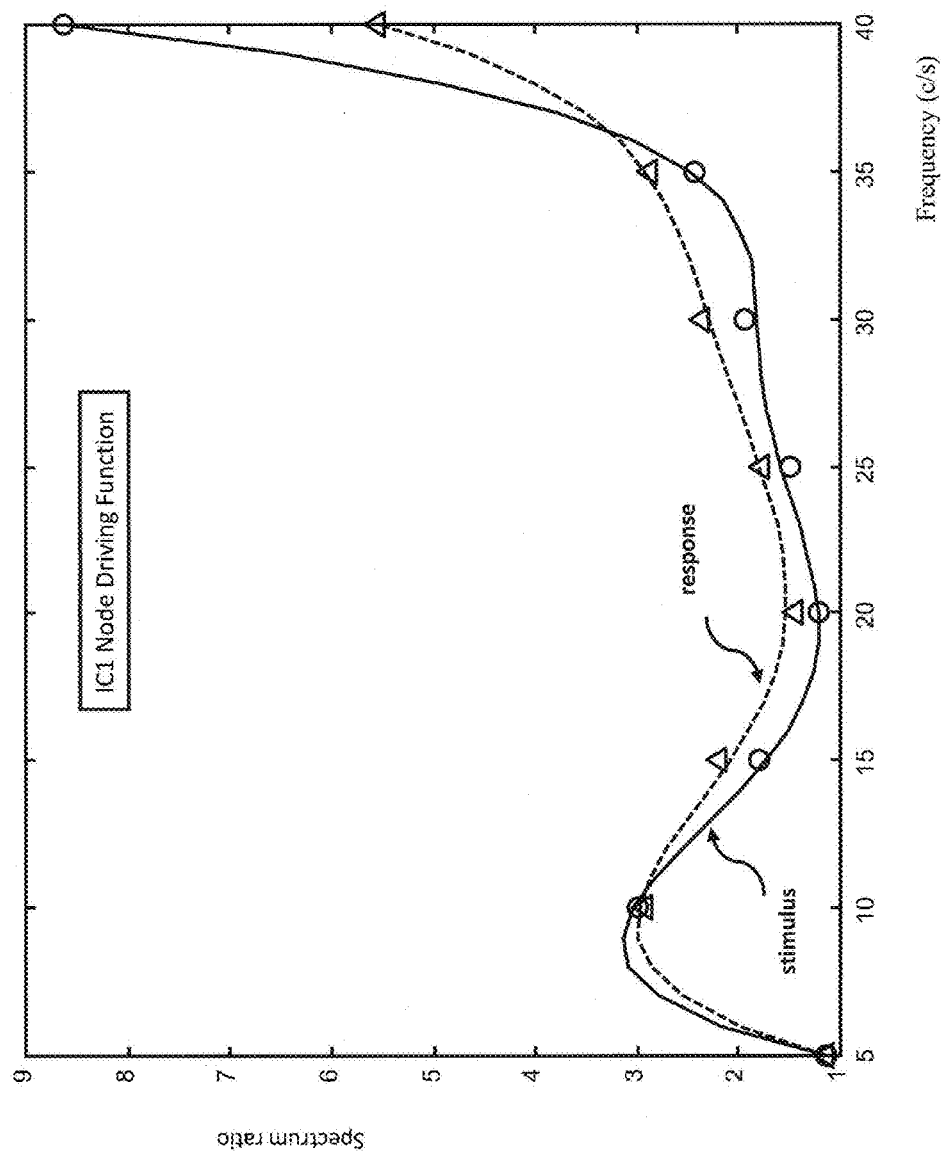
FIG. 26 shows a source node excitation driving function.
Figure 27:
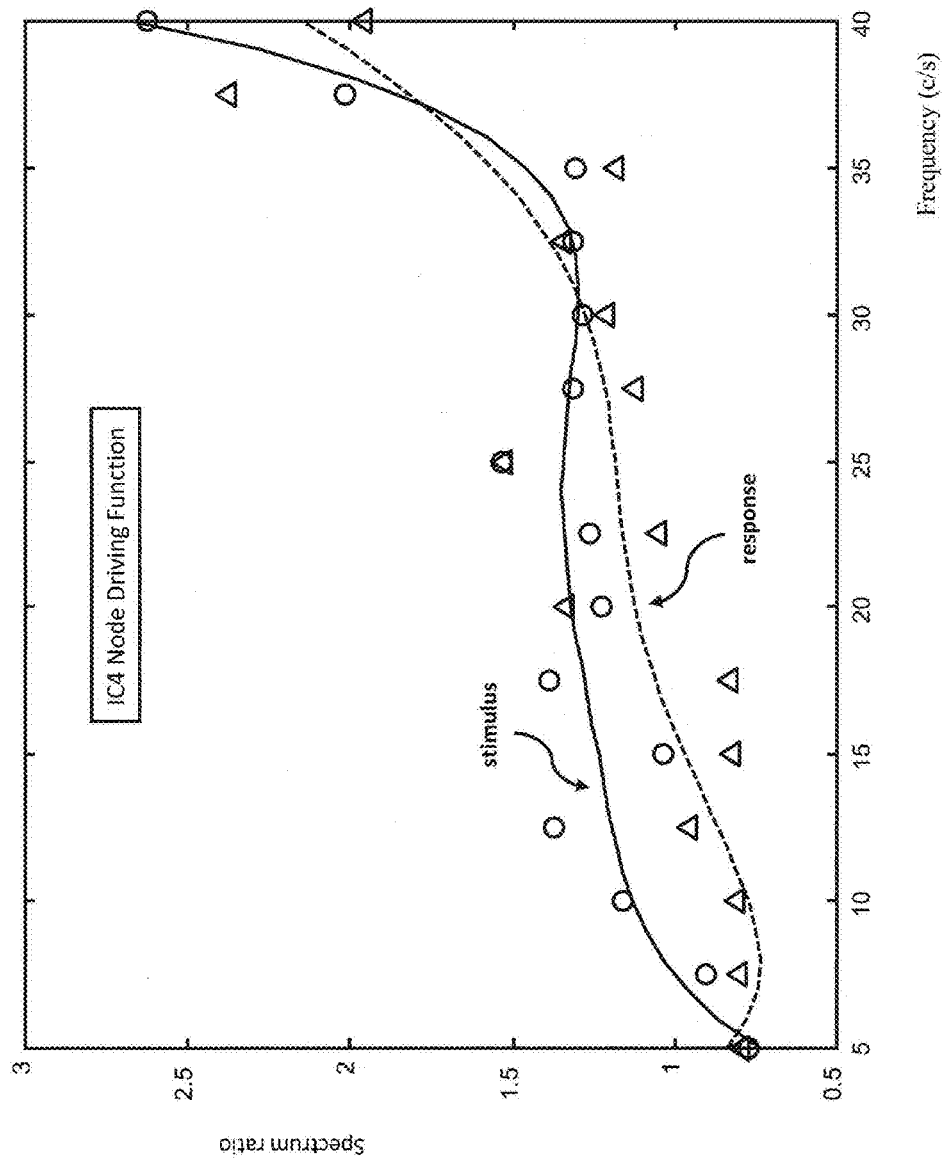
FIG. 27 shows a second source node excitation driving function.

Now considering the source node excitation driving function, the function for the first source is plotted in FIG. 26, while that for the second source is plotted in FIG. 27. The functions are smoothed by a $5^{th}$ order polynomial fit for the stimulus event (solid line) and the response event (dashed line), plotted from 0 to 40 Hz. The driving functions for the first source are practically the same for both events peaking at about 10 Hz and with a valley at about 20 Hz; while the functions for the second source are dissimilar, with that for the stimulus event fairly flat and that for the response with a valley at about 7 Hz. In summary, it appears that the first source is driving the network, while the second source is passive and more so in regard to the response event.

Statistical Results

Reported are the results for the statistical analyses of the modulator source activations, the node driving functions, and the family-wise significance of the tests.

Modulator Activations

Figure 28:
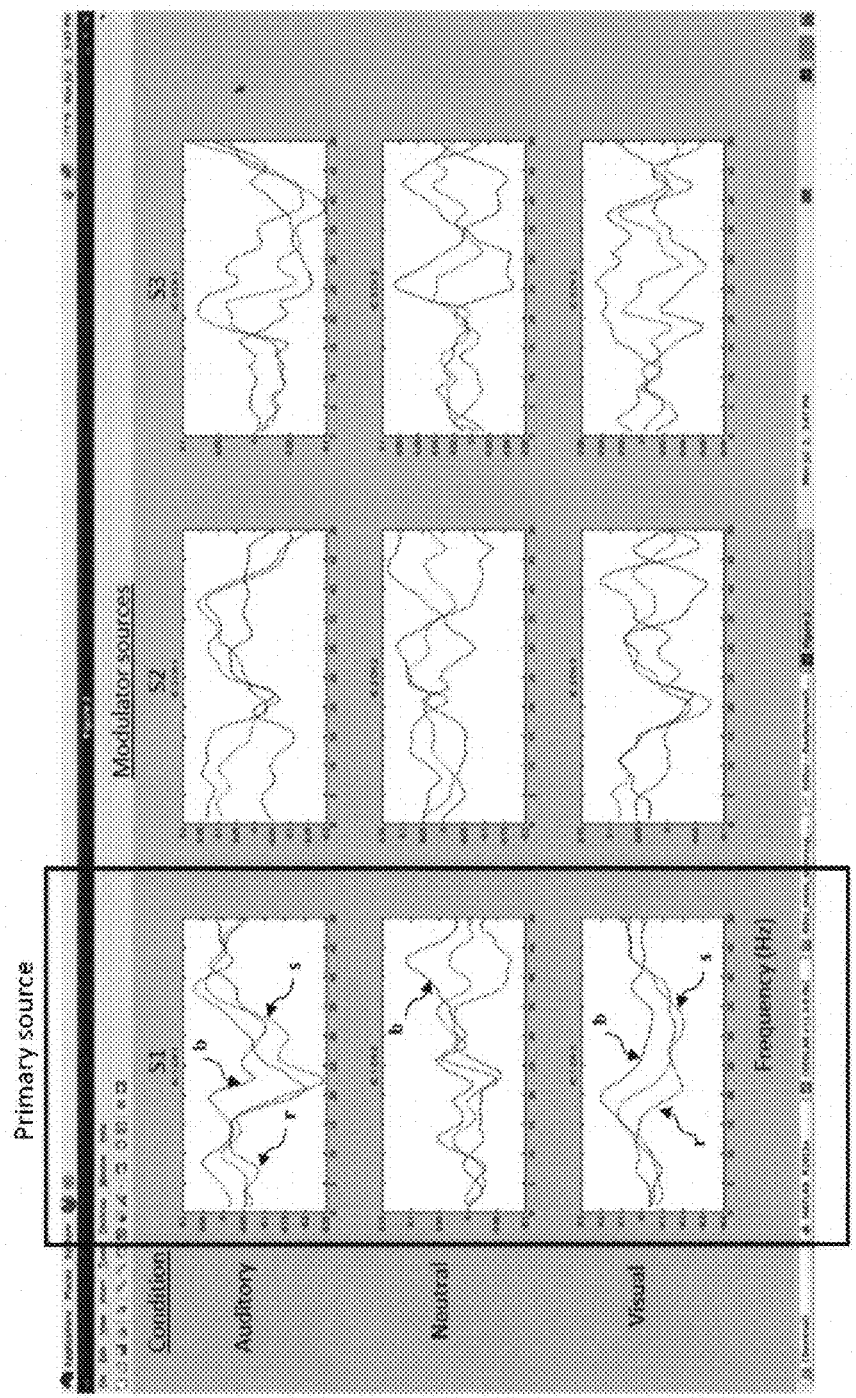
FIG. 28 shows network modulator frequency plots for event types by conditions.
Figure 29:
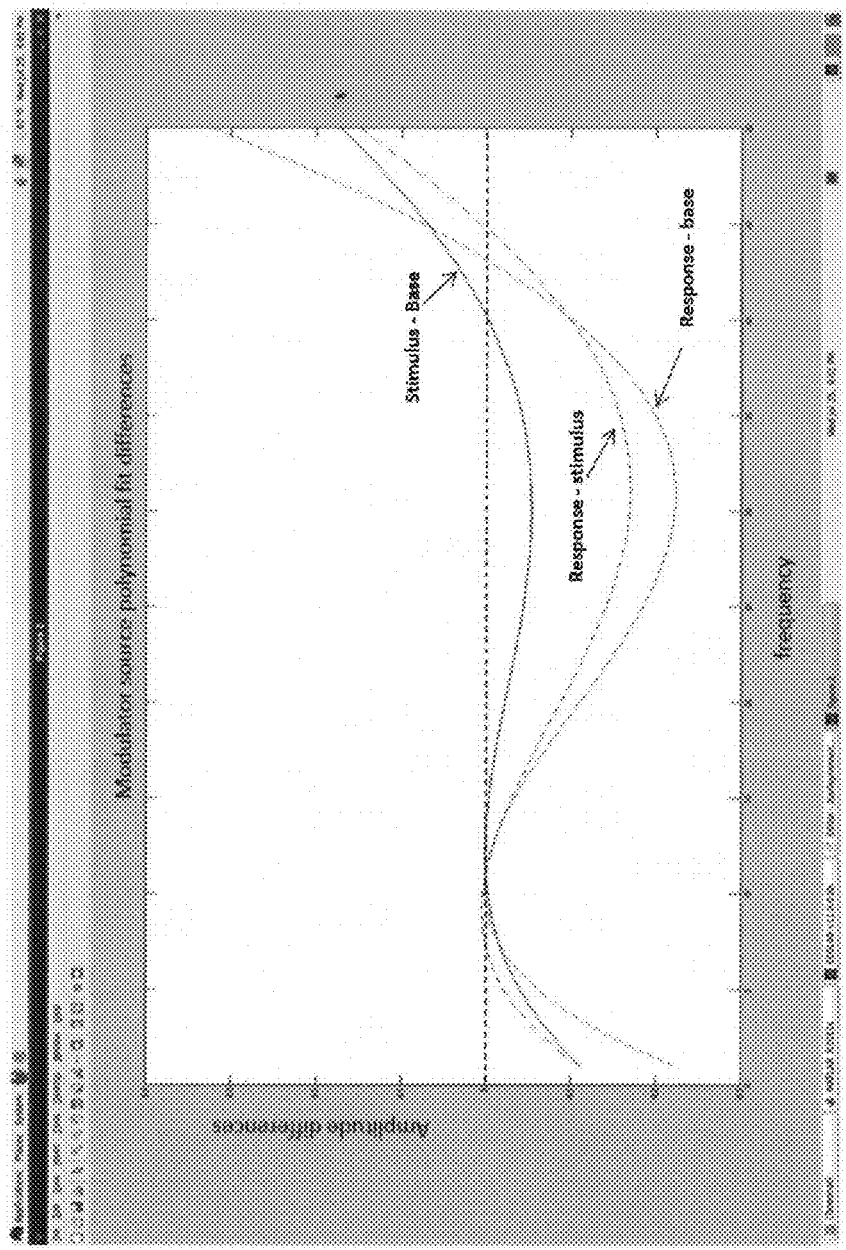
FIG. 29 shows first modulator event type differences.

Frequency plots for three modulators resulting from an independent component analysis of all source driving functions, are shown in FIG. 28, as smoothed curves averaged across test participants for the baseline (['b']), stimulus (['s']), and response (['r']) events of the three test conditions (auditory, neutral, visual), plotted from 0 to 50 Hz. The plots for the stimulus and response events in the auditory and visual conditions are similar in a cyclic pattern of roughly 1 cycle over 40 Hz centered on a spectrum peak about 20 Hz; however, the spectrums are more erratic for the baseline event in the auditory and visual conditions and all events in the neutral condition since no stimulus was presented in this condition as a control. The modulators are ordered by variance as computed in the independent component analysis, with the first modulator having the strongest variance. The plots show that the modulators S1 and S3 exhibits variations between the events for the visual and auditory conditions in the 15-25 Hz range, but not for the neutral condition; and that the remaining source show little variation for all conditions. FIG. 29 shows plots of the activation differences computed as the absolute difference in consecutive event polynomial curve-smoothed activations summed over the spectrum frequency. The plots show valleys in the 30 Hz region for the base to stimulus, base to response, and stimulus to response differences.

Parameterization—

A $4^{th}$ order polynomial curve was fitted to the modulator source excitation spectrums for all subjects; higher orders resulted in ill-condition fits. Application of a Pearson Correlation bivariate test showed that the coefficient poles tend to correlated by source but not necessarily across sources; however poles for a source are significantly correlated at the 0.01 level (2-tailed). Applying a Factor analysis for dimension reduction results in a single component extracted for each source (based on Eigenvalues greater than 1), with at least 95% (95.02, 97.76, 97.48) of the variance explained. The source factors were statistically analyzed separately for the experimental treatments and for the event cases. Since this resulted in one source as significant, the poles of that source were analyzed in turn in the same manner.

Modulator Activation Pole Analyses—

The coefficients poles used in polynomial smoothing of the primary modulator activation were statistically analyzed with a general linear model multivariate statistical test, with subject dummy variables included for the repeated measures.

Experimental Treatments—

The statistical test is significant by treatments for condition (Pillai's trace=0.584, F=25.797, df=10, p=0.000), trial (trace=0.352, F=33.968, df=5, p=0.000), and event (trace=0.470, F=11.652, df=15, p=0.000); a test of effects shows that lower order poles of the first modulator source are significant by condition (p=0.000) and event (p=0.000). Multiple comparisons shows that these poles separate the neutral condition from the others (neutral vs. auditory: p=0.004; neutral vs. visual: p=0.003); and separate the events (baseline vs. stimulus: p=0.001; baseline vs. response: p=0.000; stimulus vs. response: p=0.007).

Events—

Figure 30A:
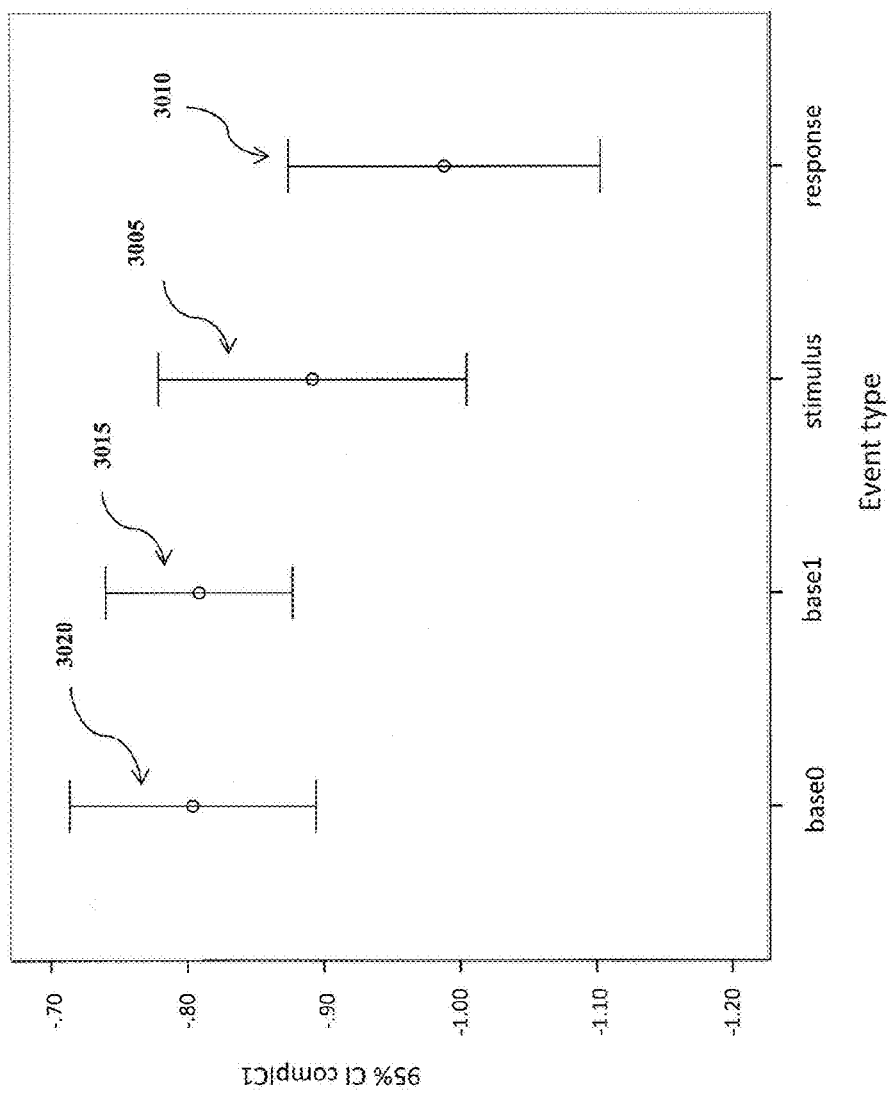
FIG. 30a is an error-bar plot for first modulator average by event types.

The test is significant by event type (Pillai's trace=0.598, F=15.788, df=15, p=0.000); a test of effects shows that the lower order poles of the first modulator source are significant (p=0.000). Multiple comparisons shows these poles separates the types (baseline vs. stimulus: p=0.000; baseline vs.

response: p=0.000; stimulus vs. response: p=0.000). FIG. 30*a* is an Error Bar plot (95% CI) for the first source average by event type. The figure suggests that the measure separates the stimulus (3005) and response (3010) from the event baseline (3015) but not from each other. Further, there is no separation between a pre-baseline (3020) and the event baseline (3015), as would be expected.

Modulator Activation Differences—

The difference measure for the primary modulator was statistically analyzed in a linear model multivariate statistical test on the experimental conditions, with subject dummy variables included for the repeated measures; a similar statistical test was performed on the event types.

Experimental Treatments:

The statistical test is significant by treatments for condition (Pillai's trace=0.160, F=10.448, df=6, p=0.000), and event (trace=0.133, F=5.600, df=9, p=0.000), but not the trials; a test of effects shows that the first source is significant by condition (F=29.075, df=2, p=0.000), and event (F=13.839, df=3, p=0.000). Multiple comparisons show significant separation of conditions (neutral vs. auditory: p=0.000; neutral vs. visual: p=0.000; auditory vs. visual: p=0.000).

Figure 30B:
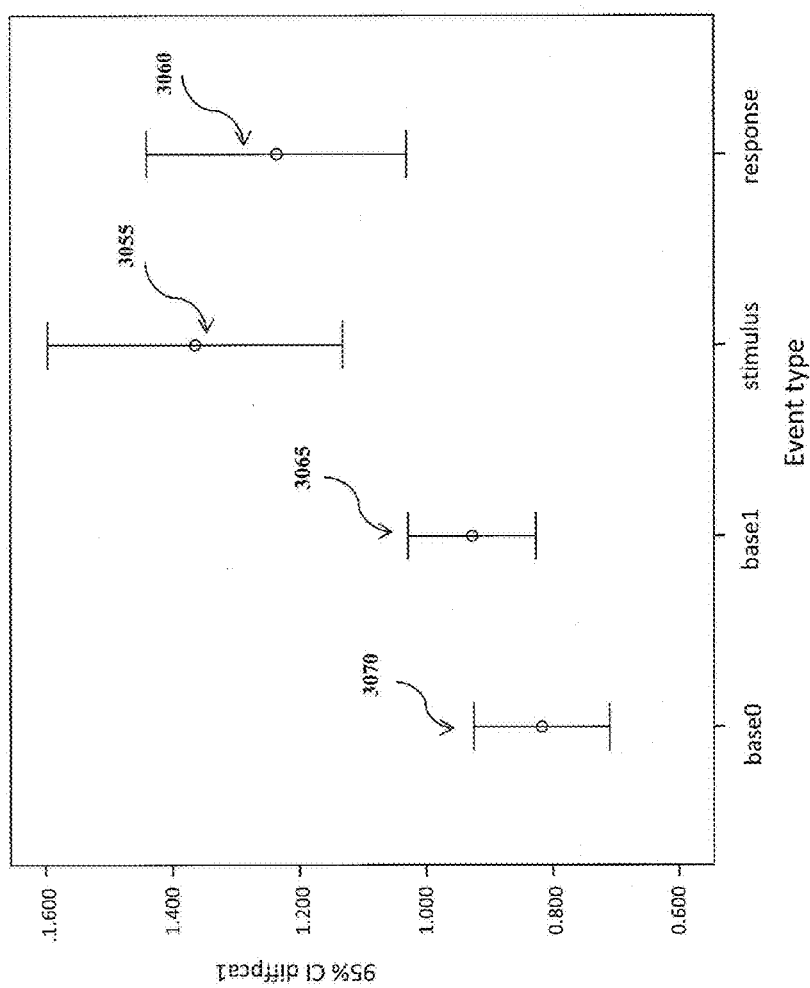
FIG. 30b is an error-bar plot for first modulator difference measure by event types.

Events:

The test is significant by event type (Pillai's trace=0.227, F=9.951, df=9, p=0.000); a test of effects shows the first source is significant (F=31.523, df=3, p=0.000). Multiple comparisons show significant separation of the baseline from the stimulus and response (baseline vs. stimulus: p=0.000; baseline vs. response: p=0.000). FIG. 30*b* is an Error Bar plot (95% CI) for the first source difference measure by event type. The figure suggests that the measure significantly separates the stimulus (3055) and response (3060) from the event baseline (3065) but not from each other. Further, there is no separation between a pre-baseline (3070) and the event baseline (3075), as would be expected.

Node Driving Functions

Similar patterns occur with the node-excitation driving functions for all participants as with the modulator sources. Again, a $4^{th}$ order polynomial fit was applied to the driving function spectrums for all subjects; higher orders resulted in ill-condition fits. And application of a Pearson Correlation bivariate test showed that the poles tend to correlated by driving function source but not necessarily across sources; however poles for a source are significantly correlated at the 0.01 level (2-tailed). Note that the visual and auditory trials commonly contained 50 stimulus events.

Node Driving Function Pole Analyses—

The coefficients poles used in polynomial smoothing of the driving functions were statistically analyzed with a general linear model multivariate statistical test, with subject dummy variables included for the repeated measures.

Experimental Treatments:

The statistical test is significant by treatments for condition (Pillai's trace=0.715, F=2.983, df=100, p=0.000), trial (trace=0.482, F=4.969, df=50, p=0.000), and event type (trace=0.710, F=1.669, df=150, p=0.000); a test of effects shows that lower order poles of most sources are significant by condition and event. Multiple comparisons show that these poles significantly separate the neutral condition from the auditory and visual, and the baseline event from the stimulus and response.

Figure 31A:
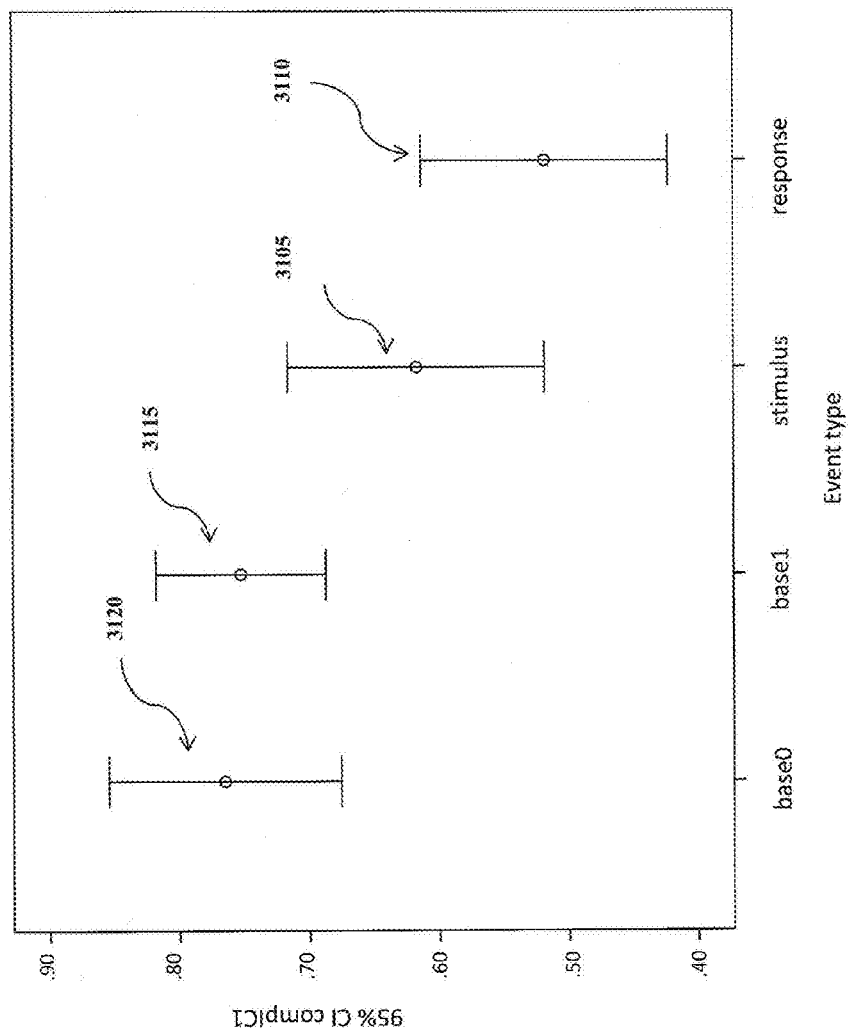
FIG. 31a is an error-bar plot for node driving function average by event types.

Events:

The test is significant by event type (Pillai's trace=0.881, F=2.260, df=150, p=0.000); a test of effects shows that the lower order poles are significant at the p=0.000 level. Multiple comparisons show that these poles separate the baseline from the stimulus and response. FIG. 31*a* is an Error Bar plot (95% CI) for the average measure by event types; the plot shows that the events are well separated. The figure suggests that the measure significantly separates the stimulus (3105) and response (3110) from the event baseline (3115) but marginally separate one baseline from the other (3120).

Node Driving Function Differences:

The difference measure for driving functions was statistically analyzed by a general linear model univariate analysis of variance with subject dummy variables.

Experimental Treatments:

The statistical test is significant by condition (F=50.354, df=2, p=0.000), and event (F=20.209, df=3, dfe=13, p=0.000), but not trial; multiple comparisons shows significant differences among conditions (p=0.000).

Figure 31B:
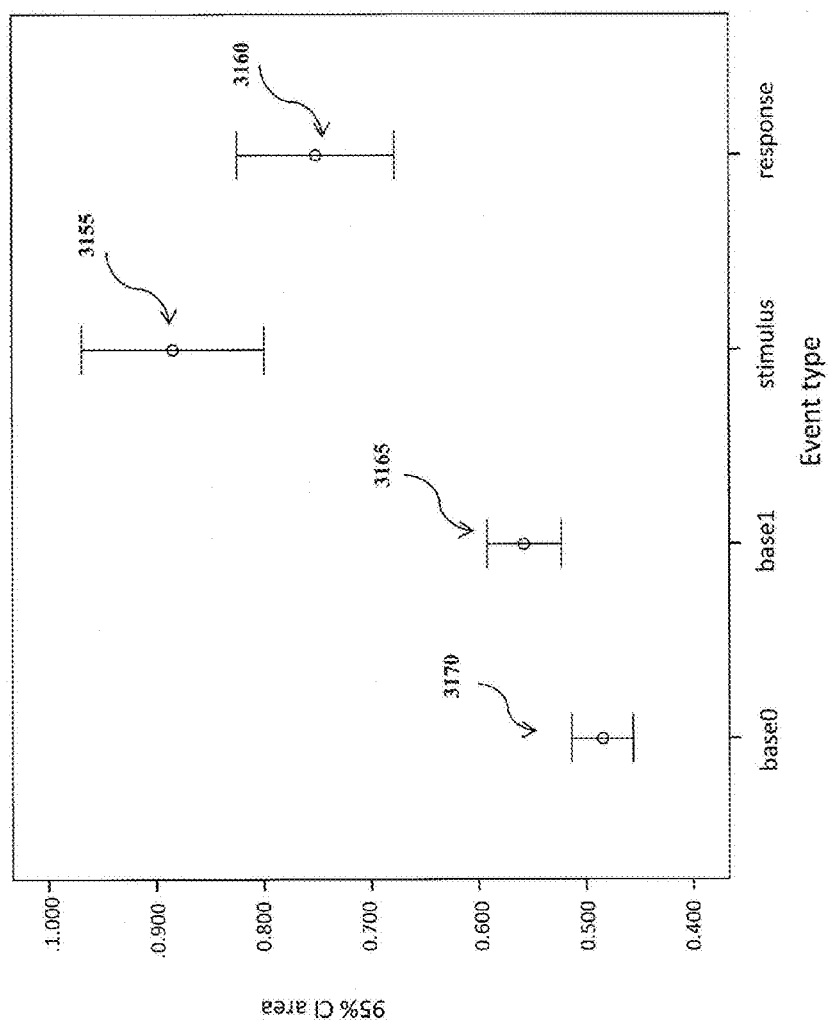
FIG. 31b is an error-bar plot for node driving function difference measure by event types.

Events:

The test is significant by event type (F=46.636, df=3, p=0.000); multiple comparisons show significant differences among types (p=0.000). FIG. 31*b* is an Error Bar plot (95% CI) for the difference measure by event types; the plot shows that the events are well separated. The figure suggests that the measure significantly separates the stimulus (3155) and response (3160) from the event baseline (3165). Further, while there is separation between a pre-baseline (3170) and the event baseline (3165) suggesting an overly sensitive measure, the separation is slight compared to that for the baseline to the stimulus and response events.

Family-Wise Statistics

The Holm-Bonferroni simultaneous test procedure is used to control for the family-wise Type-I error by partitioning the overall alpha level of 0.05 among a family of tests. In this study, all statistical tests by treatments for condition and event, and all tests for event type, are significant at p=0.000, and therefore are family-wise significance.

Cortical Network Analysis Results

Figure 32:
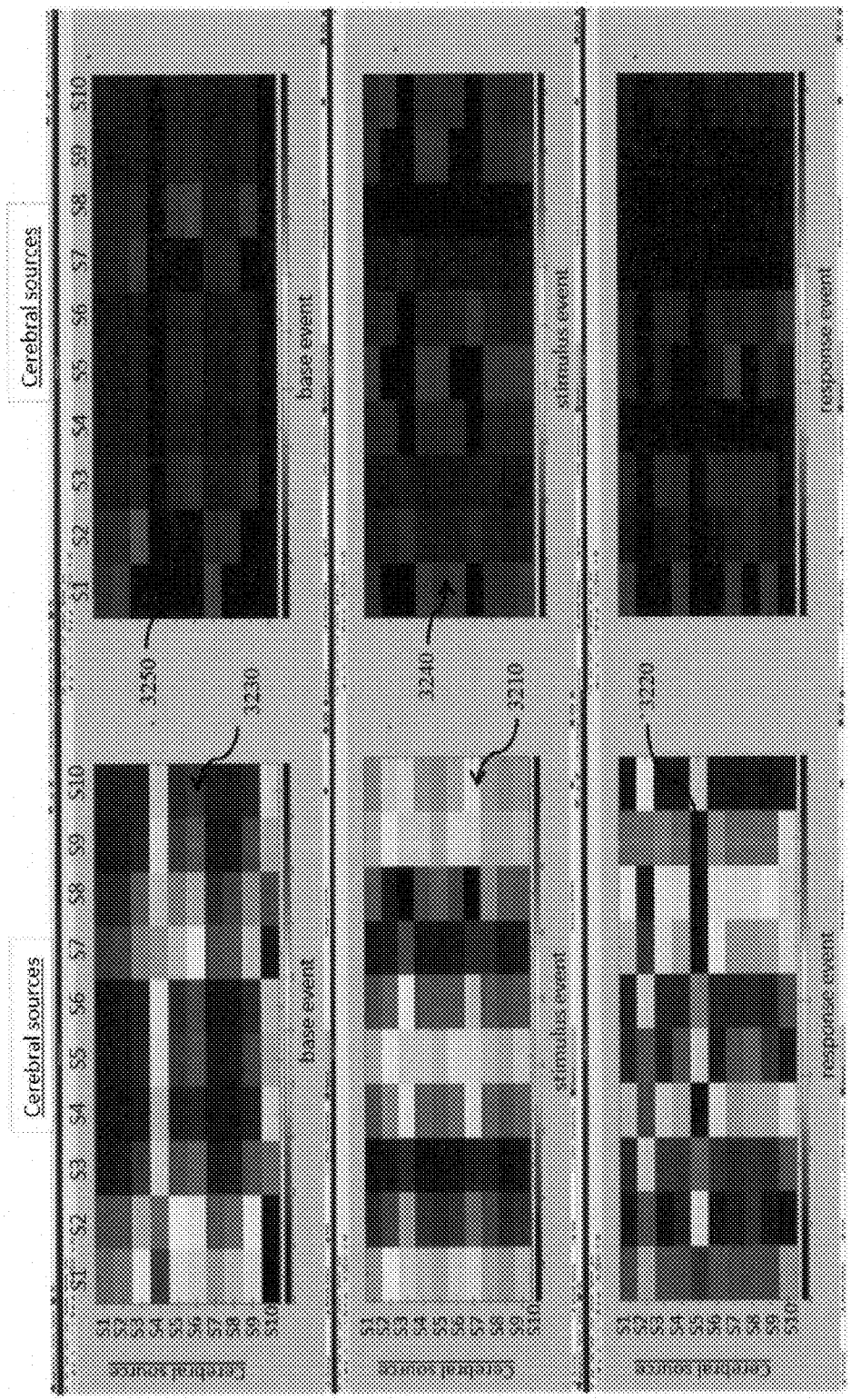
FIG. 32 shows a cross-correlation matrix for cerebral source node excitation driving functions.

The cross-correlation matrix of the node-excitation driving functions may be used to derive network properties as a small world network, such as the node degree and network connectivity. The average cross-correlation matrices of the node driving functions computed from non-normalized sliding inner product by (one-sided) frequency lag are shown as gray-scaling of color-coded figures along with a full scale color-bar for the event classes in FIG. 32 (color bar left end: minimum correlation value, right end: maximum value), along with the matching thresholded matrices. In the original color-coded figures, the higher correlation values were coded in red and the lower values in blue. For the full cross-correlation matrix in grayscale, the intermediate correlation is in the lighter shade 3210, the low correlation in the dark shade 3220, and the high correlation in intermediate shade 3230. For the thresholded matrix in grayscale, the high correlation is in the lighter shade 3240 while the low correlation is in the darker shade 3250. The abscissa of the graph (horizontal axis) corresponds to the function held constant in the correlation; the ordinate to the function indexed (lowest to highest, top to bottom). The diagonal elements correspond to the node autocorrelation which is unity at zero lag; the distribution is not necessarily uniform about the diagonal because of the one-sided correlation process. Threshold values are computed for the thresholded cross-correlation matrixes using the grand mean value and standard deviation for the matrix (threshold=mean+1.96*std), and resulting matrixes are segmented as 'background noise' elements for those values below the threshold and 'object' elements for those values above the threshold.

Network Properties

Cortical networks may be described as small world networks, mathematical graphs in which most nodes are not neighbors of one another, but can be reached from every other by a small number of steps; the typical distance (the number of steps) between two nodes in such scale-free networks is proportionally to the logarithm of the number of network nodes. These graphs may be classified by two independent structural features: the clustering coefficient and the average node-to-node distance (average shortest path length). Cortical networks tend to have a small average shortest path length and a large clustering coefficient since they consists of groups of shortest paths nodes centered on hub nodes with a high degree (i.e., number) of connections. Another measure is the efficiency of the network in the parallel transfer of information. The network properties are computed from the cross-correlation matrices as described below.

Node Degree Distribution:

The degree of a node (vertex) is the number of connections (edges) with other nodes in a network. The degree of the network is the average across all nodes. The connections are determined from a binary cross-correlation matrix computed from the original using a threshold of 0.817 (mean of 0.778+1.96*std dev of 0.019); nodes are connected if the correlation exceeds this value. The result is a set of sub-graph matrices for the direct neighbor nodes of each sub-graph index node. Table 1 of FIG. 33 lists the node degrees by event class. The table shows that the base and stimulus event networks have a high degree of connectivity as compared to the response network, and that the first, seventh, eighth, and ninth have a high degree of connectivity across event classes as opposed to the other nodes; however, there is wide spread of node degree within event classes.

Clustering Coefficient:

The absolute clustering coefficient of a node is the ratio of the number of existing connections to the number of all possible connections; the absolute clustering coefficient of the network is the average of all nodes. The existing connections are computed from the correlation weights for the connections of the binary matrix. The number of all possible connections are computed from the node degree ($d_i$) given in Table 1, as $d_i*(d_i-1)/2$. Table 2 of FIG. 33 lists the clustering coefficients by event class; the table shows higher clustering for the stimulus and response networks than for the base, and that the third node has high clustering across event class compared to the other nodes.

Shortest Path Length (Diameter):

The diameter of the network is related to the length of the shortest path between any two nodes. Here, the path length is computed as the inverse of the correlation weights for the connections of the binary correlation matrix. Table 3 of FIG. 33 listing the path lengths by event class, shows that the response network has the shortest path length as compared to the other networks; and that the first, seventh, eighth, and ninth have a longer path length across event classes as opposed to the other nodes. It is noted that the average path length is on the order of that expected for a cortical network as a scale-free network with uncorrelated power law distribution (average distance diameter of $ln(ln(10))=0.834$).

Efficiency:

The efficiency is a measure of the fault tolerance resulting from parallel transfer in the network and is computed as the inverse of the harmonic mean of the minimum absolute path length between each pair of nodes; the network global efficiency is here computed as the average of local node efficiency. The local efficiency is a measure of the connectivity remaining in a sub-graph when the index node is removed. Table 4 of FIG. 33 listing efficiencies by event type, shows that the base network has lower efficiency as compared to the other networks, and that the third node has higher efficiency across event types as compared to the other nodes.

Network Metrics:

Table 5 of FIG. 33 shows a table of the summary metrics for the event type networks; as presented in Table 6, the results suggest that the base network with less clustering and efficiency and more spread out is a form of 'scale free' default network, the stimulus network is a focused task related network ('scale-free') spread out with high degree and high diameter, and high clustering and high efficiency, and the response network is a task related 'small-world' network that has less degree and diameter, and greater clustering and efficiency. Note that the average diameter for a scale-free network is on the order of $ln(ln(10))\sim0.83$.

Event Type Network Nodes:

Table 7 of FIG. 33 shows the assignment of the source nodes to the event type networks. The assignments are derived from the network metrics using the Matlab clustering routine 'kmeans.m' to minimize the sum over all clusters of the within cluster sums of metric point-to-point distances for a specified number of clusters.

Cortical Network

Figure 34:
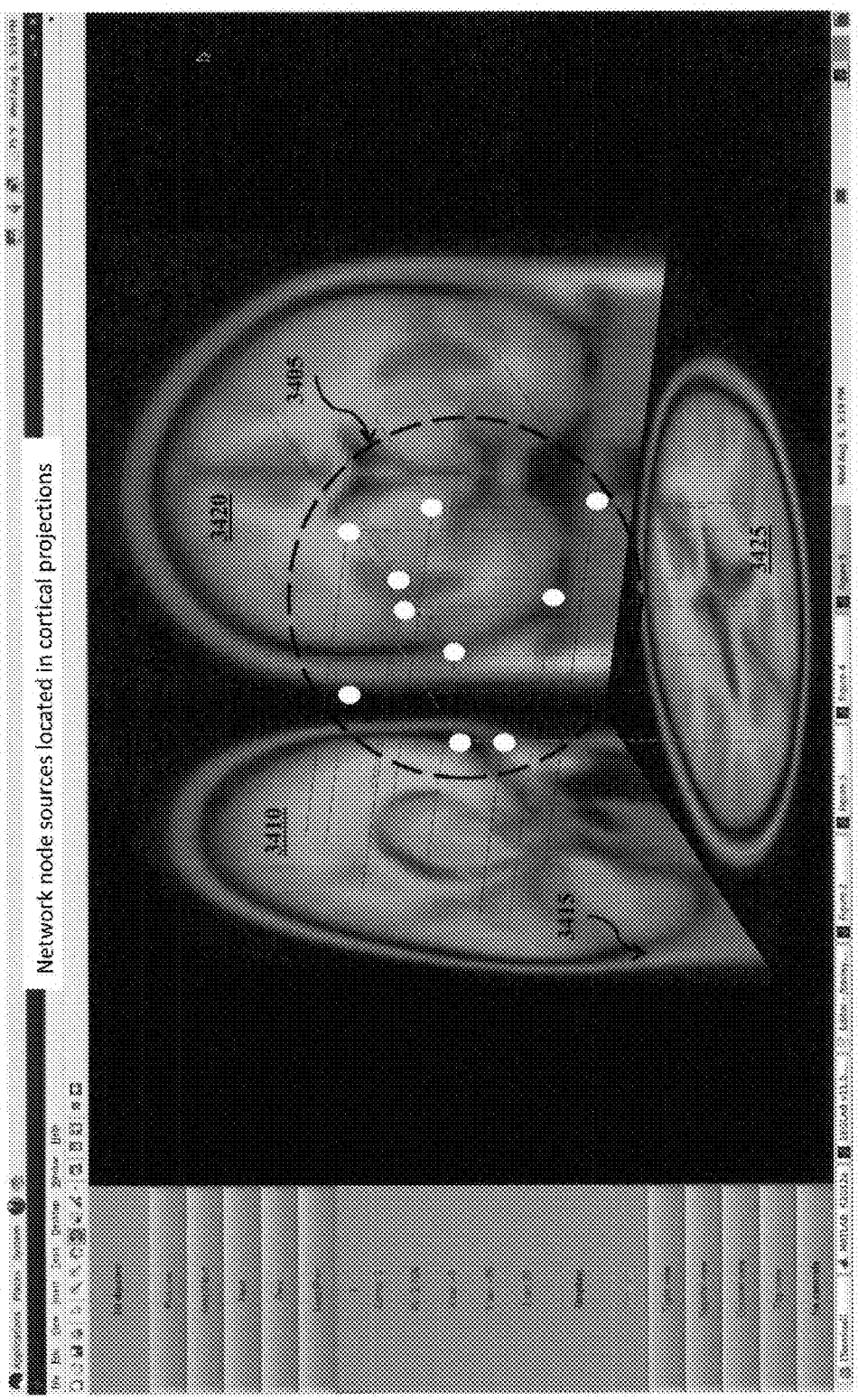
FIG. 34 is network node representative sources located in MRI projection Talairach space.

In this step, the source nodes for an event type network are mapped to the Brodmann Areas of the human brain cortical regions. In this process, the source locations in the spherical head coordinates may be converted into Talairach-space coordinates using standard transformations (see, e.g., http://sccn.ucsd.edu/wiki/A08:_DIPFIT), from which the cortical structure and the corresponding Brodmann Areas may be derived using the 'Talairach Client' brain gray matter mapping software (see, e.g., http://www.talairach.org/client.html). FIG. 34 shows sources located in a three-dimensional MRI projection Talairach head space, as point dipoles grayscale colored white (without orientation indicated) located within the region 3405. The projection shows a lateral mid-sagittal view of the cortex 3410 with the skull at the inion 3425, a frontal coronol view of the cortex 3420, and a transverse view 3425. In further embodiment, the Brodmann Areas for the event networks may be isolated from the network source nodes as determined from Table 7.

Figure 35:
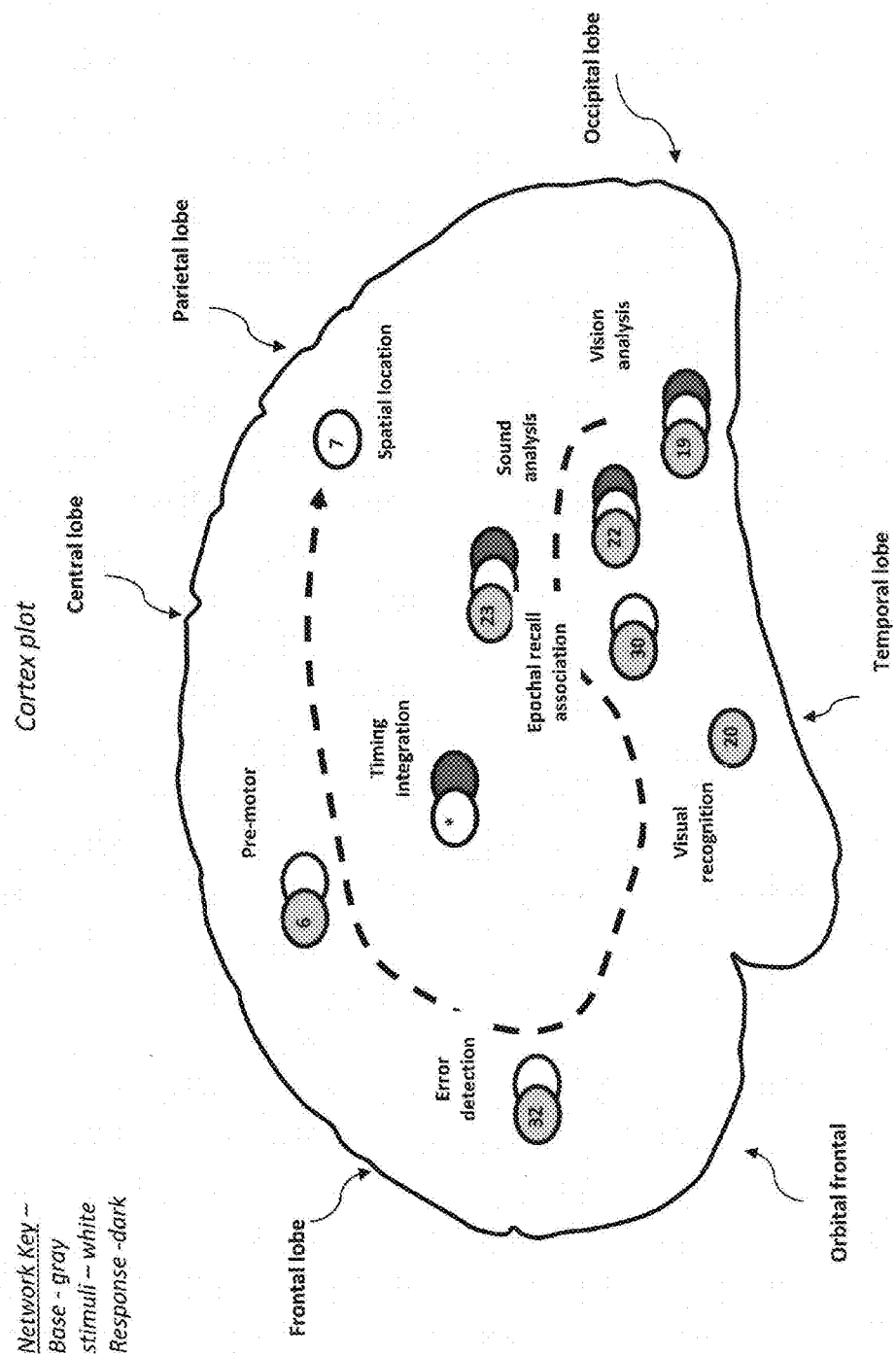
FIG. 35 is a cortical diagram of node sources located by Brodmann Areas for stimulus.

FIG. 35 shows a network for the events with the Brodmann Areas involved superimposed on a side view of the cortex with lobes indicated. Here, the network includes cognitive functions for stimulus analysis (BA 9, BA 22), association (BA 23), recognition (BA 20), error detection (BA 32), pre-motor planning (BA 6), and spatial locating (BA 7) presumably of the choice response button. Note that not all cortical sources map to Broadman Areas in the neocortex region, but some may instead be in the allocortex; here, the network includes a node (*) for the claustrum structure in the sub-lobar lobe for timing in the stimulus and responses events. Sources in the base network are grayscale colored gray, those of the stimulus white, and the response dark gray. Information flow is shown by the directed line.

Figure 36:
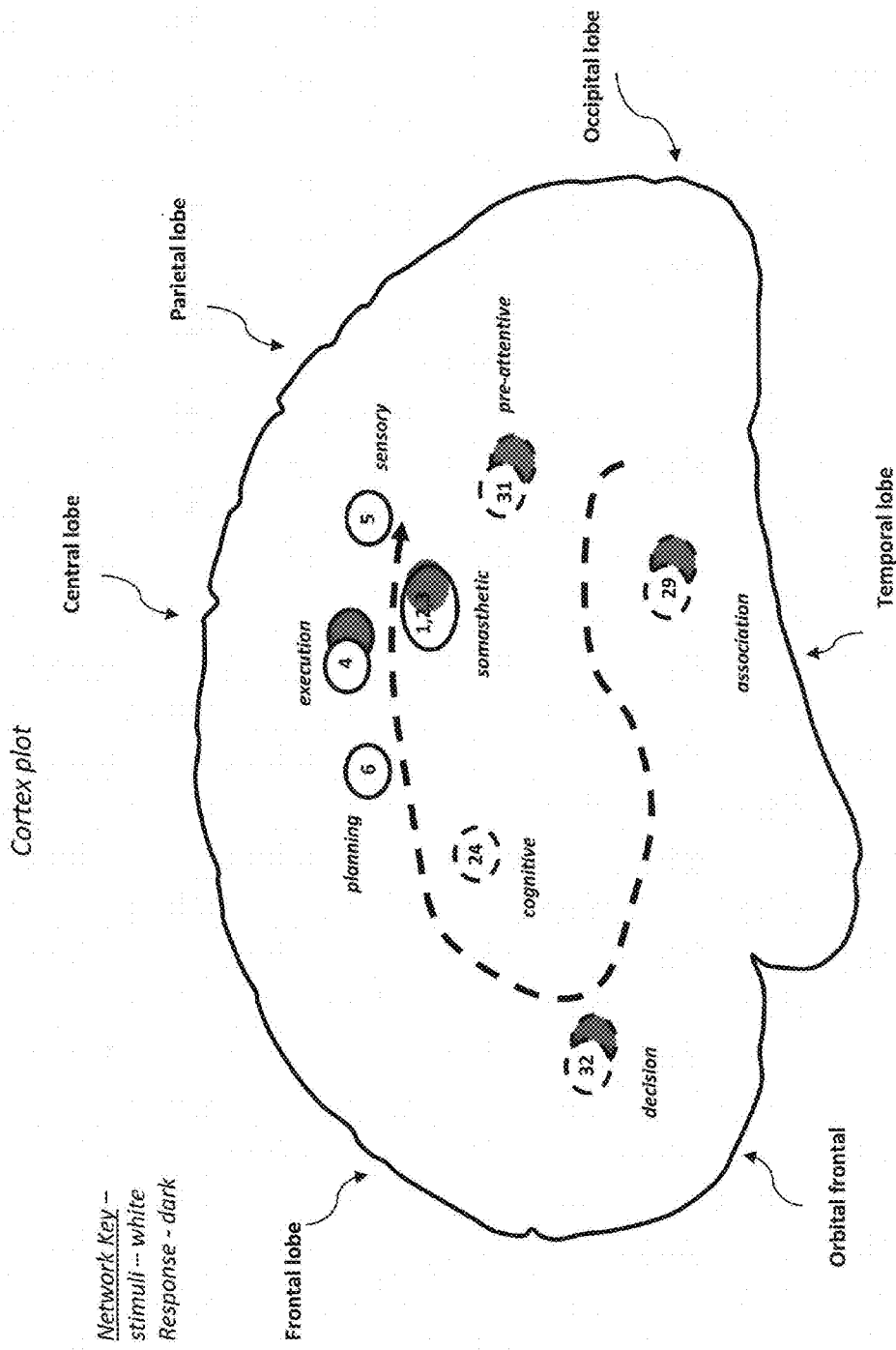
FIG. 36 is a cortical diagram of node sources located by Brodmann Areas for reaction.
Figure 37:
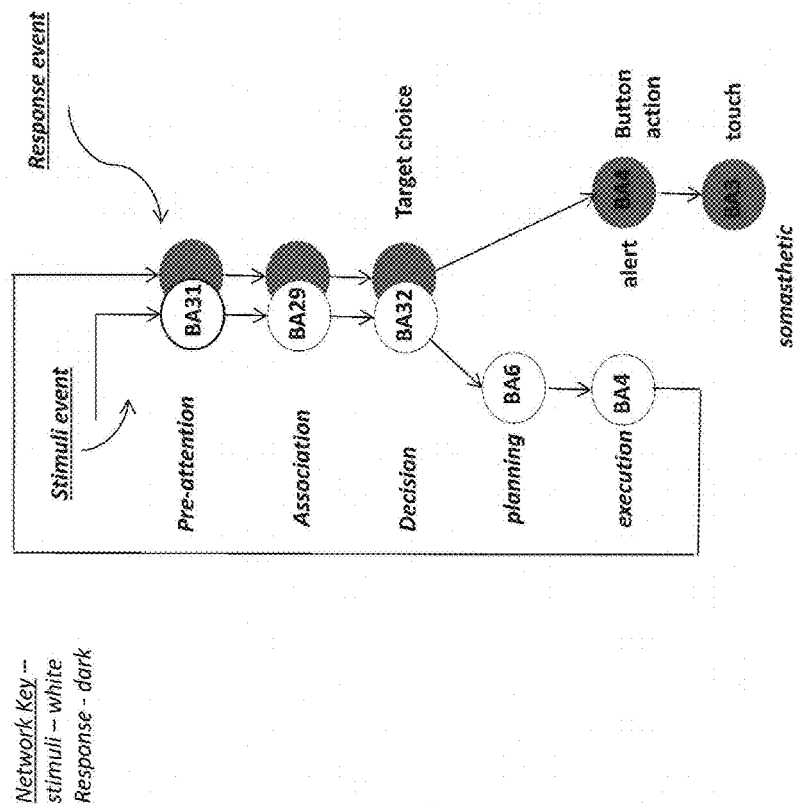
FIG. 37 is a cortical Network flow of node sources by Brodmann Areas for cortical reaction.

FIG. 36 shows a network isolated for the stimulus and response events with cognitive functions for attention (BA 31), association (BA 29), decision (BA 32), planning (BA 6), motor execution (BA 4) and somasthetic processing (BA 1, 2, 3) which involved in the response presumably occurs with the finger execution and consequent touch sensation (BA 5) at the completion of the execution. Sources in the stimulus network are grayscale colored white, and the response dark gray. Information flow is shown by the directed line. Finally, FIG. 37 is a flowchart showing the cognitive functions of FIG. 36 organized by activity and the associated Brodmann Areas for the stimulus and response events. The chart shows the flow of activity from initiation of the stimulus event (grayscaled white) to the response event (grayscaled dark) and task completion.

Results Summary

All tests by treatment condition and event, and by event case of modulator and node measures from polynomial fits and differences are family-wise significant. All measures of the primary modulator source and of the node driving functions are statistically significant by treatment conditions and event, and separate the base event from the others; most measures separate the stimulus from the response, as well.

Considering the effects of the modulator sources, the source with strongest variance (the primary source), is significant by treatment condition and event, and by event case, as measured by the lower order poles of a polynomial fit or by the absolute differences. Considering the effect comparisons for this modulator source, all measures separate the stimulus from the response, and the base event from the others.

With respect to the node-excitation driving functions, most nodes are significant by treatment condition and event, and by case, as measured by the higher order poles of a polynomial fit, and separate the stimulus from the response, and the base event from the others. Considering the node poles, all lower order poles separate the base from the others, and most lower order poles separate the stimulus from the response, as well. The implication is that the function base and trend and less so the quadratic, are most sensitive to the treatments including the event class.

Of the measures derived from the node-excitation driving function, the most sensitive to a change in event case appears to be the node absolute grand difference, since this measure strongly separates the stimulus from the response, as well as both events from the base. This sensitivity increases with sample size by increasing averaging over samples before computing the absolute difference.

Representative modulator source spectrums computed from the average polynomial poles are nearly linear increasing functions of frequency more so for the stimulus than the base and less so for the response. The spectrums are maximally separated about 30 Hz in the high-Beta frequency range. Similarly, the representative node driving functions are linearly increasing functions of frequency peaking about 30 Hz; the spectrums are separated in the Beta range centered about 30 Hz and in the alpha range centered about 10 Hz.

Node network properties computed from thresholded cross-correlation matrices show differences by event case in such parameters as node degree distribution, clustering coefficient, network diameter (shortest path length), and efficiency. The average path length is on the order of that expected for a scale free network with uncorrelated power law distribution, commonly found for cortical networks.

A representative cortical source network is derived for the node network by clustering the sources weighted by the network properties for the event classes; the cortical source set is mapped into Talairach-Space coordinates for which equivalent cortical labels including Brodmann Areas are derived using the "Talairach Client" gray matter mapping; the network source activations derived from the correlation matrices are mapped to cognitive functional areas through the corresponding Brodmann Areas resulting in a network model of cortical functions for the event cases.

In particular, as would be expected, the methodology isolates sources located at BA 31 for pre-attentive processing and at BA 29 for association that are involved in both the stimuli and response events; a source at BA32 for decision involved in both events, while a source at BA6 for motor planning is involved in the stimuli event presumably for planning the response and a source at BA4 for executing the alert orientation. Furthermore, the source at BA 4 (motor execution) and one at BA3 for somasthetic processes are involved in the response event presumably with finger execution to a button and touch sensation at completion of the execution.

Applications of Disclosed Methodology

The invention has various applications. One is as a component of an automated aiding system in the electronic aiding of tasks performed by human operators for crew-served systems including aiding for operators of combat vehicles and robotic control stations, by providing an estimate of brain functions from electroencephalogram measurements. Modern combat systems are increasingly operated autonomously by on-board electronic systems with the operator in a supervisory role; manual intervention may be called for by the electronic system only in critical moments. In such incidents, the electronic aider may constitute a display organizer, which electronically aware of the task priorities, schedules the information needs for the task and arranges such in a display format that is in a manner supportive of the performance by the operator; in particular, such corresponding to a cognitive flow rate in the operator that is compatible with control dynamics that may be needed for a task. Essential to the functioning of the display organizer is the development of a control strategy that comprises specifying a reference course of action to be executed, and a schedule of task events composed of time periods and sub-tasks to be enabled during the time periods for the course, where the sub-tasks are ordered from task initiation to task completion by the operator.

A common design feature of the electronic aider is an embedded model of operator cognitive attention that with knowledge of task demands may be used for scheduling the information display. In some designs, the model may comprise an information processing model with cognitive processors controlled by a model executor, and rules for the activation of the corresponding processors along with associated task times and cost elements based on mapping attributes of cognitive attention. Still further, in some designs the model may be incorporated within a skills-based, rules-based, and knowledge-based model of cognitive processing; where the executor recalls task rules from the knowledge base and in evaluation sets up the rules for activation, the rules base processor activates the rules directing control, and the skills based processor controls the task execution. With this model, a control strategy for scheduling displays is determined by a process that with access to the processor task times and cost-elements, computes associated cost variables for sub-task combinations; and selects the optimal cost schedule to best facilitate task cognitive attention. In this process, cognitive attention is used as a metric for the event sub-tasks, where the attention is an element of an attention state set ranked by the degree of cognitive involvement of such ordered from task initiation to task completion. In further elaboration, the ranking is by the states of orientation, task recall, task focus, option review and decision, activation, and continual control. Here, reference is made to U.S. patent application Ser. No. 13/721,161, filed Dec. 20, 2012, and further to U.S. patent application Ser. No. 13/792,585, filed Mar. 11, 2013, both by the inventor, for further teachings of modeling task attention.

An important step in the scheduling process is knowledge of the attention state of the human operator, since a fully ordered schedule sequence starting from initiation could interrupt the cognitive flow being executed by the operator, who may already be involved in the task. The interruption may disorient the operator resulting in an evaluation of the displays, and consequently poor performance until the operator recovers. For this reason, the scheduling is initialized from the task attention state of the operator as determined by an electronic task attention processor from measurements from the operator, such as eye movements and eye-gaze fixations, measurements of the state of brain cognitive functions, and manual activity in performance of the tasks, as well as the state of the task performance. In this design, the invention as embodied below estimates the states of the cognitive processors of the scheduling model for the task attention processor from the brain cognitive functions as determined from electroencephalogram measurements. Since the skill controlling brain processes are sub-cortical, they cannot be readily determined from electroencephalogram measurements using standard technology, and the state of the model skill processor is estimated by the task attention processor from the skill-based ocular and manual activities. Further, the relation of the operator's attention to the task is determined by the task attention processor from the status of the task. Here, reference is made to U.S. Pat. No. 8,708,884 by the inventor, titled: "Systems and methods for adaptive mitigation of motion sickness," herein incorporated by reference, for further teachings of reducing operator activities to estimates of the cognitive attention state. Having described the role of the invention as a component of the electronic aiding system (via the task attention processor), an embodiment for this application is now elaborated.

In application, an embodiment of the invention is executed in two stages, with a first training stage using an initial set of Electroencephalogram (EEG) scalp recordings data to automatically derive independent sources representative of the cerebral functions and a classifier based on the source driving functions, and a second application stage sequentially estimating the source activations from short term data segments. Parameterization kernels composed as the node driving functions may be derived from the source estimated activations for classifying the associated cortical functionality in real time. The same date reduction is applied to the raw data in both stages to ensure stochastic consistency.

The training stage comprises three steps. In the first step, automatic artifact rejection algorithms are applied to the data set to prune epochs and channels of extreme noisy sets; then following application of blind-source separation analysis, the resulting set of independent sources are automatically pruned of contaminated sources leaving a set of cerebral sites representative of cerebral functions as well as the associated mixing weight matrixes. In the third step, the sources are clustered to form representative networks which are then parameterized, the results of which along with event indices are used to train a state classifier for real-time application.

The application stage comprises a continual sequence of short term scalp recorded data segments to which the un-mixing weight matrixes are applied following automatic artifact adjustments, to estimate the independent source activation datasets for the segment window. Parameterization kernels are applied to the source activations for classifying the associated cortical functionality in real time. In the present design, multivariate autoregressive and spectral analysis is applied to compute the kernel measures composed as the node driving functions from source auto and cross power, and directed transfer functions.

Figure 38:
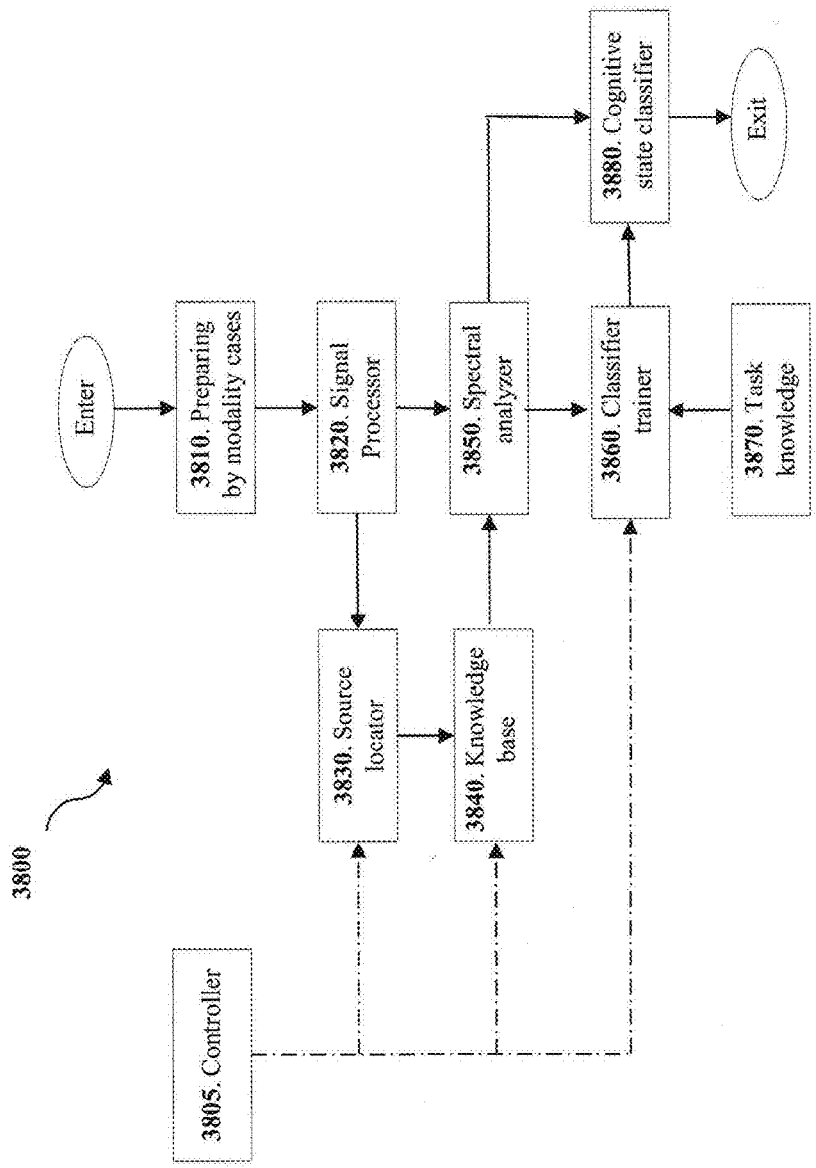
FIG. 38 is a schematic of modular components of invention for use in application to automatic aiding.

An embodiment of the invention is shown in FIG. 38, with the embodiment 3800 including of a set of electronic hardware and/or software modules, with a control module 3805, a module 3810 for preparing collected EEG samples for stimuli modality response cases of interest in application from the base set, a module 3820 for signal processing of the case sample, a module 3830 for locating cortical sources of the case sample as a training set, a module 3840 as a knowledge base containing the case source information, a module 3850 for spectral analyzer of the source activations derived from the case sample, a module 3860 for training a cognitive state classifier from the spectral analysis of the training set and the task knowledge 3870, and a module 3880 for classifying the sample as to cognitive state following classifier training. The modules are activated by the control module 3805 in different combinations depending upon whether the set is for training or a normal application. The modules may be activated for training in the sequence of preparing a set of training samples for case 3810, signal processing 3820, source location 3830, spectral analysis 3850, and classifier training 3860, from the training set spectral analysis and the task knowledge base task knowledge 3870, resulting in un-mixing matrixes for the sources saved in knowledge base 3840 and the classifying parameters in 3860 for reference. In application, the cognitive state is determined by the module 3810 preparing samples by case, signal processor 3820, spectral analysis 3850 of the source activations using the un-mixing matrixes from 3840, and classifying the cognitive state using the parameters from 3860. Applications may be for different stimuli modality response cases with the samples processed at a preferred sampling rate, montage, and reference electrode site maximizing signal contrasts for each case, although reference electrode choice does not affect source localization. The module 3810 prepares a case sample from the original base data set with the sampling rate derived from the base rate by filtering and down sampling, and the montage and reference electrode from adding the base set site voltages for the preferred configuration. An example is that of processing an auditory data set for three dimensional auditory cueing by binaural cues from sub-cortical auditory brain stem frequency-following responses with a base set possibly sampled at 10 kHz, external reference set to bilateral earlobes, and digitally high-passed filtered at 40 Hz and low-passed at 1.5 kHz; and from audio cerebral responses from the auditory cortex with the base set low-pass digital filtered at 40 Hz and down-sampled to 256 Hz, and reference of a common reference electrode (sum of all site voltages). Resetting the sampling frequency for the audio cerebral response reduces the pole order needed for representation as an autoregressive process to a practical level for application of the invention.

Figure 39:
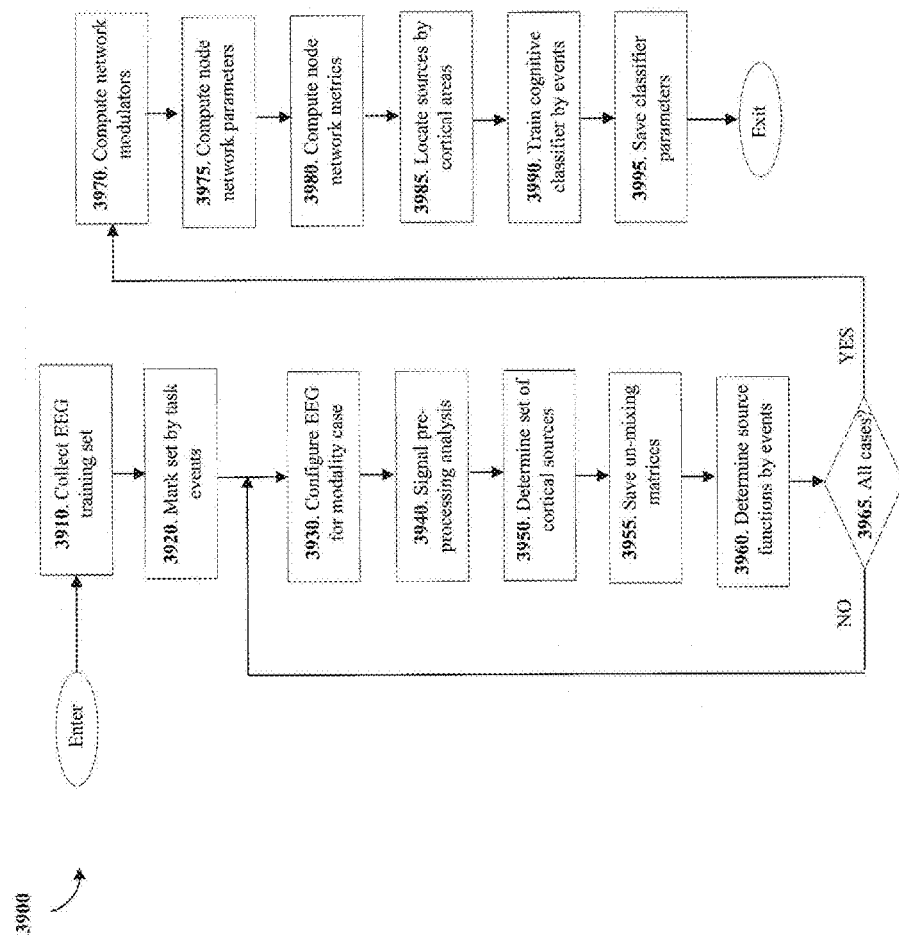
FIG. 39 is a flow chart showing the training sequence method in detail.

FIG. 39 is a flow chart showing the training sequence method 3900 in detail, starting with collecting the scalp site EEG for a training data set in step 3910 and marking the set by task events in step 3920 that occurred during the collection process. Then, for all stimuli modality cases, the data set is configured for analysis for a case in step 3930, pre-processed in step 3940 by obvious artifact corrections for analysis, determining a set of cortical sources of the scalp signals in step 3950 and in the process saving the corresponding un-mixing matrixes of the source activation signals in step 3955 for reference in the application, and determining the node driving functions in step 3960 for the sources. Once completed for all cases in step 3965, the sets of node driving functions may be used to compute network modulators in step 3970 with accompanying un-mixing matrices, compute node network parameters in step 3975, and using these parameters, compute node network metrics in step 3980, and having located the sources in a cortical space, map the sources to the cortical Brodmann Areas in step 3985 for associate functions. These parameters may then be used to train a cognitive classifier by events in step 3990, and those of the classification saved in step 3995 for application. In one embodiment, these functions may be performed with the techniques described in the demonstration section, where for example, the artifact correction is by extreme scalp signal amplitude, trend, spectrum, or kurtosis, following filtering and baseline correction. Determining the cortical sources may be by blind-source temporal separation based on kurtosis, with pruning of sources of artifact from the source set by spectrum and cortical location. The node driving functions may be determined from spectrum analysis based on multivariate autoregressive analysis of the source activation signals. Further, the network modulators may be determined by blind-source separation from the node driving functions following principal component analysis to reduce the function spectrum dimensionality. Techniques have been described above for computing network parameters from the cross-correlation matrix of the node driving functions, the metrics from the parameters, locating the sources from triangulation of the scalp signals, and mapping the source locations in the spherical head coordinates into Talairach-space coordinates for locating the corresponding Brodmann Areas.

Figures 40A, 40B:
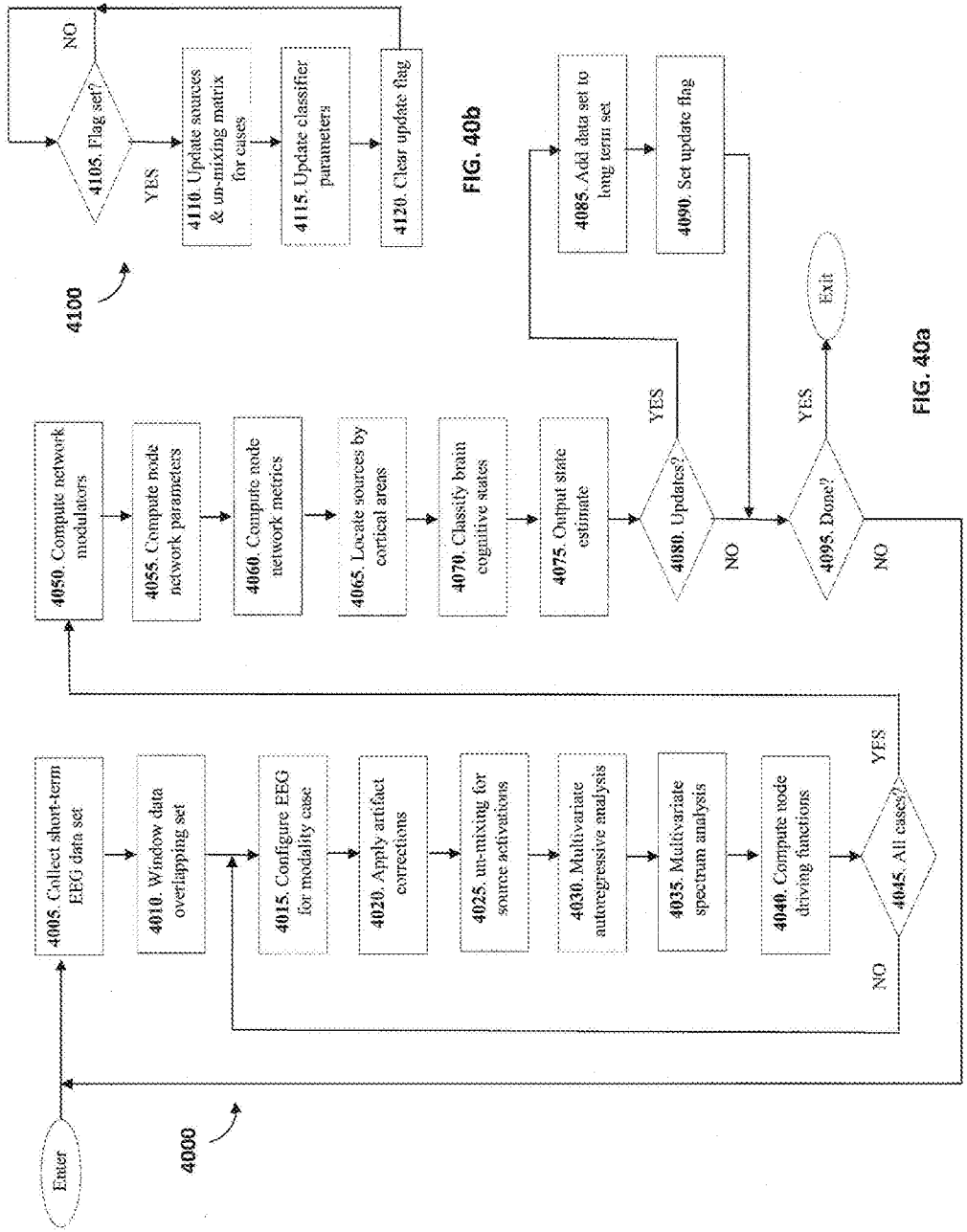
FIG. 40a is a flow chart of training process of invention for use in automatic aiding.
FIG. 40b is a flow chart of application process of invention for use in automatic aiding.

FIG. 40a is a flowchart of the application sequence method 4000, applied continually during application following completion of training. In each application cycle, a short-term scalp site EEG data set is collected in step 4005 in overlapping time windows in step 4010, then for each stimuli modality response case, the windowed data set is treated in the same way as for the training sequence, with the set configured for the case in step 4015 and artifact corrections applied in step 4020, then the source activations are generated from the treated scalp signals with the un-mixing matrix in step 4025, a multivariate autoregressive analysis applied to the activations in step 4030, spectrum measures computed from the autoregressive coefficients and noise covariance in step 4035, and source node driving functions computed from the spectrum measures in step 4040. Once completed for all cases in step 4045, the sets of node driving functions may be used to compute network modulators in step 4050 with the un-mixing matrices from training, compute node network parameters in step 4055, and using these parameters, compute node network metrics in step 4060, and having located the sources in a cortical space, map the sources to the cortical Brodmann Areas in step 4065 for associated cognitive functions. These parameters may then be used with the cognitive classifier to classify the cognitive state using the classification weights from training in step 4070, with the state estimate as output. In one embodiment, these functions may be performed with the techniques applied in the training sequence. The validity of the process depends upon the stochastic stability of the EEG process since the cortical sources from the training are assumed to remain consistent over the application period. For this reason, the application may periodically in step 4080 request an update of the sources and classifier information with the short term raw EEG data added to an extended data file in step 4085 and an update request flag set in step 4090 for a standalone update module. Following the update check, the application cycle is repeated in step 4095, until the application is completed.

FIG. 40b is a flowchart for the standalone update module 4100, which once the update flag is set in step 4105, calls for the update of the sources and un-mixing matrixes by cases in step 4110, and updates the classifier parameters in step 4115 using the extended EEG data base with the routines of the training sequence, then clears the update flag in step 4120 in preparation for the next request.

Figure 41:
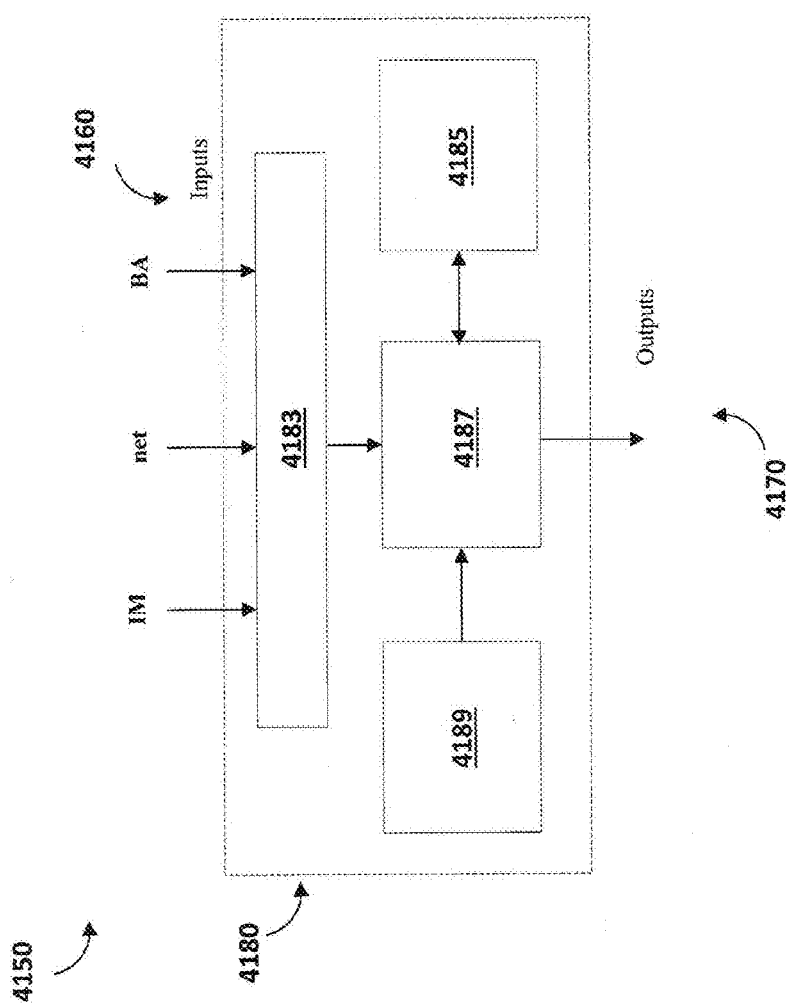
FIG. 41 is a schematic of classifier module of an embodied as an expert system with knowledge base and inference engine.

In one embodiment shown in FIG. 41, the classifier 4150 can be a knowledge base system configured as an expert system 4180, with an input buffer 4183, knowledge base 4185, inference engine 4187, and inference rules 4189, with input 4160, here shown as data on the network modulators (IM), network metrics (net), and source Brodmann Areas (BA), and brain cognitive state output 4170. In further embodiment, the input may include the node-excitation driving functions as well. In this design, the input buffer may store time-wise sequential values. The knowledge base asserts relations among the inputs and the cognitive states depending upon the values, with the network modulators on network control, the network metrics on the type of network, and the Brodmann Areas on the network functions. The inference engine is an automated reasoning system that evaluates the current state of the knowledge-base, applies relevant rules, and then asserts new knowledge into the knowledge base using in one embodiment 'if-then' rules based on parameters set in the training session. In other embodiments, the classifier may be of different designs including those of discriminative models that maximize the output based on a training set, such as a logistic regression model, a support vector machine maximizing the margin between a decision hyperplane and the training set, or a multiple layered perceptron configured as an artificial neural network with nodes in an input, output, and hidden layers, with the nodes between adjacent layers connected with weighted links.

In this design, the cerebral cortical source nodes may be mapped to Brodmann Areas and the corresponding brain functions. As mentioned above, the occipital, somatosensory, and temporal cortical lobes are organized as processors for primary sensory areas (vision: BA17; somatosensory: BA1, 2, 3; temporal: BA41 for auditory, BA43 for gustatory), and secondary sensory areas (vision: BA18; somatosensory: BA5; temporal: BA42 for auditory), association areas (vision: BA19; somatosensory: BA7; temporal: BA22), along with multiple association areas in the parietal and temporal (BA20, 21, 15), which in turn lead to the frontal lobe for evaluation (BA9, 10, 11, 12), with pre-motor frontal eye-fields for directed vision (BA8), and secondary motor (BA6) and primary motor (BA4) for action. Specialized temporal and frontal areas process language understanding (BA39, 40) and generation (BA44, 45). These functions may be specialized further by cortical hemisphere. In addition, the anterior cingulate is believed involved in error detection (BA24, 32) and the posterior cingulate in emotion (BA23, 31). Further involved are the limbic system regions of entorhinal cortex (BA34), perirhinal cortex (BA35), and the ectorhinal area (BA36) of the perirhinal cortex, among others for spatial memory and orientation.

Further, the cortical brain functions of the source node network may be mapped to the cognitive processing network for classification of attention to a task. In this process, the modulator sources are a measure of the strength of attention, while the network topology corresponds to the attention involvement. As has been mentioned above, a default network corresponding to self-referral has less clustering and efficiency and is more spread out in a form of 'scale free' network; a task focused network would be spread out but with high degree and high diameter, as well as high clustering and high efficiency; and a task response network would perhaps be a 'small-world' network that has less degree and diameter, and greater clustering and efficiency.

In some embodiments, the classifier outputs of the brain cognitive state may be mapped through the knowledge base of the expert system to the state of information processing as expressed by a cognitive processing model for the human operator, and in particular, to the states of the separate processors making up the model from the corresponding cortical networks. In this process, the cortical structure as located by the Brodmann Areas of the network may be mapped to a model of information processing, where in some designs, these models comprise cognitive processors controlled by a model executor, and rules for the activation of the corresponding processors as components of an information processing network. As has been mentioned, the model may be incorporated within a skills-based, rules-based, and knowledge-based model of cognitive processing; where the executor recalls task rules from the knowledge base and in evaluation sets up the rules for activation, the rules base processor activates the rules directing control, and the skills based processor controls the task execution. In this model, the levels of involvement of the processors depend upon the attention state of the network as determined by the executor.

There is a neurological basis for the validity of such a model within the human cerebral cortex with presumably the executor mapped to the orbitofrontal cortex believed involved in planning, the knowledge base to the temporal lobes, the rules processor to the anterior parietal and the pre-motor cortex with control setting to the motor cortex. The skills processor may be mapped to the cerebellum with a reference setting from the motor cortex and visual offset from the pontine nuclei via the posterior parietal for foveal vision or even directly from the visual cortex for peripheral vision. Further, the reference may be set by the parietal cortex in visual-egocentric coordinates for comparison to delayed visual returns. The cerebellum is believed essential to coordinating motor limb and digit movements. Each of these centers taken together may comprise cortical attention networks for eye-movements, working memory, spatial distribution, and temporal expectation, within the frontal, temporal and parietal brain regions. Again, reference is made to U.S. patent application Ser. Nos. 13/721,161, 13/792,585, both by the inventor, for further teachings of modeling task attention.

FIG. 42 is a schematic showing an embodiment of the invention which is configured as a component of an automated aiding system 4200 for an operator including activity behavior and physiological measurements, with the invention providing an estimate of the brain functions from electroencephalogram measurements. Here, the operator 4202 is attending to a task aid 4207 presented on a display 4205. In some embodiments, an operator's electroencephalogram (EEG) measurements are made with scalp skin-surface electrodes for EEG 4242, the signals of which are input to a brain function assessor 4240. In some embodiments, the EEG recording may be made from a scalp cap of multiple electrodes judiciously distributed about the scalp (for example, in a standard 10-20 International System electrode configuration, or the like), all with amplifiers having output to the assessor 4240. Limb activity may be measured with an actimeter with embedded accelerometers attached to the wrist and output 4222 to motor activity estimator 4220. The video output from the video camera 4215 goes to an eye tracker 4250 with eye-movement processor 4255, and output of eye-movements and fixation patterns 4257. The output 4245 from the brain function assessor 4240, the output 4224 from the motor activity estimator 4220, and the output 4252 from the eye-movement processor 4257, are inputs to a task attention state assessor 4260. The output 4262 of task attention state assessor and the task needs 4274 from the autonomous operating system are inputs to the electronic aider 4270, with output 4272 to the display driver 4280, scheduling the updating of the aid display cue. In this aiding system, the invention estimates the states of the cognitive processors of the scheduling model for the electronic task attention processor from the brain cognitive functions as determined from electroencephalogram measurements.

Various embodiments, implementations, and application of the present invention may be embodied as a plurality of electronic modules, for example. The electronic modules may be implemented as hardware, software or a combination thereof. The modules may be implemented with a computer of computing device having one or more processors (or micro-processors) as known in the art that are specifically configured to execute coding necessary to implement embodiments of the present invention. Processor-executable instructions can be stored in a memory device and execute by the processors when needed. In some implementations, software code (instructions), firmware, or the like, may be stored on a computer or machine-readable storage media having computer or machine-executable instructions executable by the processor(s). The processor(s) may be a programmable processor, such as, for example, a field-programmable gate array (FGPA) or an application-specific integrated circuit (ASIC) processor. The methodology disclosed herein may be implemented and executed by an application may be created using any number of programming routines, such as MAT-LAB. Of course, any number of hardware implementations, programming languages, and operating platforms may be used without departing from the spirit or scope of the invention. As such, the description or recitation of any specific hardware implementation, programming language, and operating platform herein is exemplary only and should not be viewed as limiting.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present disclosure and its practical applications, to thereby enable others skilled in the art to best utilize the invention and various embodiments with various modifications as may be suited to the particular use contemplated.

Various elements, devices, modules and circuits are described above in associated with their respective functions. These elements, devices, modules and circuits are considered means for performing their respective functions as described herein. While the foregoing is directed to embodiments of the present invention, other and further embodiments of the invention may be devised without departing from the basic scope thereof, and the scope thereof is determined by the claims that follow.

All patents, patent applications, articles and other references mentioned herein are hereby incorporated by reference in their entireties.

I claim:

1. A method for estimating brain activity of a human subject from electrical voltage potentials from scalp site measurements of electroencephalograms (EEG) that is executed by an electronic processor comprising electronic modules, the method comprising:

receiving measurement signals for actual scalp site voltage potentials which originate from an EEG collection system worn by the subject;

specifying, by an electronic module, a plurality of cortical neural sources of electrical potentials in the cerebral cortex of the brain of the subject;

using a model of the human brain which treats the cortical neural sources as nodes connected together in a cortical source network topologically distributed in the cerebral cortex, estimating, by an electronic module, cortical source activations from actual scalp site voltage potentials measured by electrodes of the EEG collection system worn by the subject for each of the cortical neural sources in the network for the subject;

determining, by an electronic module, source network modulation electrical control signals for the subject from the cortical source activations which are assumed to correspond to neural control modulators in the human brain; and computing, by an electronic module, a network activity classification from determined modulation electrical control signals as an estimation of brain activity of the subject, wherein, estimating the cortical source activations comprises computing a node-excitation driving function for each of the cortical source nodes of the network, where each node is assumed to constitute an activation function formed from weighted inputs, a node-excitation driving function, and an emitter function formed from weighted outputs, and where inputs to each node comprise signal power spectrums from nodes of the network and the weights are measures of the directed causality of the spectral power transfer between nodes.

2. The method of claim 1, wherein the node-excitation driving function is computed from a multivariate spectral analysis of the network node excitations which determines autoregressive coefficients and a noise covariance resulting in node power spectrums and inter-node transfer functions.

3. The method of claim 2, wherein the signal power spectrums constitute cross-power spectrums for connections between the different nodes of the network and auto-spectrums for recursive feedback by the nodes, the directed causality weights are determined as inter-node directed transfer functions, and partial spectrum powers are computed for the nodes from the signal power spectrums.

4. The method of claim 3, wherein the node-excitation driving function for each node is computed from a node signal partial power spectrum and a node activation function, where the node activation function is computed as the sum of the signal power spectrums inputs weighted by corresponding normalized transfer functions computed from the inter-node directed transfer functions.

5. The method of claim 1, wherein the modulation electrical control signals of the network control modulation nodes are determined from the node-excitation driving functions for the nodes of the network.

6. The method of claim 1, wherein the network activity classification is determined from the modulation electrical control signals of the network control modulation nodes, as derived from the node-excitation driving functions of the nodes of the network.

7. The method of claim 1, wherein the network activity classification is used to estimate activities of tasks performed by the subject during operation of a machine, from a cortical topological organization of the node network as derived from the node-excitation driving functions for the source activations of the nodes of the network.

8. The method of claim 7, wherein the network is a cortical attention network including attention to task activities of task default, task focus, task involvement, or any combination thereof.

9. The method of claim 7, wherein the network activity classification is determined for a task activity by mapping the network cortical sources to the cortical structure of the brain as cortical network nodes related to cognitive functions, including at least to the structural level of the Brodmann Area regions of the cortex with associated cognitive functions.

10. The method of claim 9, wherein the network activity classification is used to determine a task activity level from the cortical structures of the cortical network as derived from the network source node excitation driving functions for the corresponding source activations of the nodes of the network.

11. An apparatus for estimating brain activity of a human subject from electrical voltage potentials from scalp site measurements of electroencephalograms (EEG), the apparatus comprising an electronic processor which comprises:

an electronic module configured to receive measurement signals for actual scalp site voltage potentials which originate from an EEG collection system worn by the subject;

an electronic module configured to specify a plurality of cortical neural sources of electrical potentials in the cerebral cortex of the brain of the subject;

an electronic module configured to use a model of the human brain which treats the cortical neural sources as nodes connected together in a cortical source network topologically distributed in the cerebral cortex, in order to estimate cortical source activations from actual scalp site voltage potentials measured by electrodes of the EEG collection system worn by the subject for each of the cortical neural sources in the network for the subject;

an electronic module configured to determine source network modulation electrical control signals for the subject from the cortical source activations which are assumed to correspond to neural control modulators in the human brain; and an electronic module configured to compute a network activity classification from determined modulation electrical control signals as an estimation of brain activity of the subject, wherein, estimating the cortical source activations comprises computing a node-excitation driving function for each of the cortical source nodes of the network, where each node is assumed to constitute an activation function formed from weighted inputs, a node-excitation driving function, and an emitter function formed from weighted outputs, and where inputs to each node comprise signal power spectrums from nodes of the network and the weights are measures of the directed causality of the spectral power transfer between nodes.

12. The apparatus of claim 11, wherein the node-excitation driving function is computed from a multivariate spectral analysis of the network node excitations which determines autoregressive coefficients and a noise covariance resulting in node power spectrums and inter-node transfer functions.

13. The apparatus of claim 12, wherein the signal power spectrums constitute cross-power spectrums for connections between the different nodes of the network and auto-spectrums for recursive feedback by the nodes, the directed causality weights are determined as inter-node directed transfer functions, and partial spectrum powers are computed for the nodes from the signal power spectrums.

14. The apparatus of claim 13, wherein the node-excitation driving function for each node is computed from a node signal partial power spectrum and a node activation function, where the node activation function is computed as the sum of the signal power spectrums inputs weighted by corresponding normalized transfer functions computed from the inter-node directed transfer functions.

15. The apparatus of claim 11, wherein the modulation electrical control signals of the network control modulation nodes are determined from the node-excitation driving functions of the nodes of the network.

16. The apparatus of claim 11, wherein the network activity classification is determined from the modulation electrical control signals of the network control modulation nodes, as derived from the node-excitation driving functions of the nodes of the network.

17. The apparatus of claim 11, wherein the network activity classification is used to estimate activities of tasks performed by the subject during operation of a machine, from a cortical topological organization of the node network as derived from the node excitation driving functions for the source activations of the nodes of the network.

18. The apparatus of claim 17, wherein the network is a cortical attention network including attention to task activities of task default, task focus, task involvement, or any combination thereof.

19. The apparatus of claim 17, wherein the network activity classification is determined for a task activity by mapping the network cortical sources to the cortical structure of the brain as cortical network nodes related to cognitive functions, including at least to the structural level of the Brodmann Area regions of the cortex with associated cognitive functions.

* * * * *